(12) United States Patent
Fathi et al.

(10) Patent No.: US 10,748,868 B2
(45) Date of Patent: *Aug. 18, 2020

(54) ADHESIVE BONDING COMPOSITION AND ELECTRONIC COMPONENTS PREPARED FROM THE SAME

(71) Applicant: IMMUNOLIGHT, LLC, Detroit, MI (US)

(72) Inventors: Zakaryae Fathi, Detroit, MI (US);
James Clayton, Detroit, MI (US);
Harold Walder, Detroit, MI (US);
Frederic A. Bourke, Jr., Detroit, MI (US)

(73) Assignee: IMMUNOLIGHT, LLC, Detroit, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/103,355

(22) Filed: Aug. 14, 2018

(65) Prior Publication Data

US 2018/0358327 A1 Dec. 13, 2018

Related U.S. Application Data

(60) Continuation of application No. 15/455,573, filed on Mar. 10, 2017, now Pat. No. 10,074,627, which is a
(Continued)

(51) Int. Cl.
*H01L 23/00* (2006.01)
*C08K 3/00* (2018.01)
(Continued)

(52) U.S. Cl.
CPC .......... *H01L 24/83* (2013.01); *A61B 17/0057* (2013.01); *A61L 24/06* (2013.01);
(Continued)

(58) Field of Classification Search
CPC ........ B32B 2037/1253; B32B 2457/14; B32B 37/1284; C09J 133/08; C09K 11/776;
(Continued)

(56) References Cited

U.S. PATENT DOCUMENTS 6,444,305 B2 9/2002 Banovetz
6,750,266 B2 6/2004 Bentsen et al.
(Continued)

FOREIGN PATENT DOCUMENTS

JP 10011822 A 1/1998
JP 2004-177771 A 6/2004

OTHER PUBLICATIONS

International Search Report and Written Opinion dated Oct. 11, 2011 in corresponding International Application No. PCT/US11/35565 filed on May 6, 2011.
(Continued)

*Primary Examiner* — Sanza L. McClendon
(74) *Attorney, Agent, or Firm* — Oblon, McClelland, Maier & Neustadt, L.L.P.

(57) ABSTRACT

A polymerizable composition includes at least one monomer, a photoinitiator capable of initiating polymerization of the monomer when exposed to light, and a phosphor capable of producing light when exposed to radiation (typically X-rays). The material is particularly suitable for bonding components at ambient temperature in situations where the bond joint is not accessible to an external light source. An associated method includes: placing a polymerizable adhesive composition, including a photoinitiator and energy converting material, such as a down-converting phosphor, in contact with at least two components to be bonded to form an assembly; and, irradiating the assembly with radiation at a first wavelength, capable of conversion (down-conversion by the phosphor) to a second wavelength capable of acti-
(Continued)

vating the photoinitiator, to prepare items such as inkjet cartridges, wafer-to-wafer assemblies, semiconductors, integrated circuits, and the like.

55 Claims, 64 Drawing Sheets

Related U.S. Application Data continuation of application No. 15/382,835, filed on Dec. 19, 2016, now Pat. No. 10,026,711, which is a division of application No. 14/593,049, filed on Jan. 9, 2015, now Pat. No. 9,649,832, which is a division of application No. 13/102,277, filed on May 6, 2011, now Pat. No. 9,023,249.

(60) Provisional application No. 61/331,990, filed on May 6, 2010, provisional application No. 61/443,019, filed on Feb. 15, 2011.

(51) Int. Cl.

| | | |
|---|---|---|
| *B41J 2/175* | (2006.01) | |
| *C09J 4/00* | (2006.01) | |
| *A61B 17/00* | (2006.01) | |
| *A61L 24/06* | (2006.01) | |
| *B32B 37/12* | (2006.01) | |
| *B32B 37/18* | (2006.01) | |
| *B32B 38/00* | (2006.01) | |
| *C09J 133/08* | (2006.01) | |
| *C09K 11/02* | (2006.01) | |
| *C09K 11/77* | (2006.01) | |
| *H01L 25/065* | (2006.01) | |
| *H01L 25/00* | (2006.01) | |
| *B32B 3/26* | (2006.01) | |
| *B32B 7/14* | (2006.01) | |
| *B32B 9/04* | (2006.01) | |
| *C09J 9/02* | (2006.01) | |
| *C09J 11/04* | (2006.01) | |
| *C09J 11/06* | (2006.01) | |
| *H01L 23/522* | (2006.01) | |

(52) U.S. Cl.
CPC ............. *B32B 3/266* (2013.01); *B32B 7/14* (2013.01); *B32B 9/04* (2013.01); *B32B 37/1284* (2013.01); *B32B 37/18* (2013.01); *B32B 38/0008* (2013.01); *B41J 2/17559* (2013.01); *C08K 3/00* (2013.01); *C09J 4/00* (2013.01); *C09J 9/02* (2013.01); *C09J 11/04* (2013.01); *C09J 11/06* (2013.01); *C09J 133/08* (2013.01); *C09K 11/02* (2013.01); *C09K 11/777* (2013.01); *C09K 11/7769* (2013.01); *H01L 23/5226* (2013.01); *H01L 24/32* (2013.01); *H01L 25/0657* (2013.01); *H01L 25/50* (2013.01); *B32B 2037/1253* (2013.01); *B32B 2457/00* (2013.01); *B32B 2457/08* (2013.01); *B32B 2457/14* (2013.01); *H01L 2224/16225* (2013.01); *H01L 2224/32225* (2013.01); *H01L 2224/48091* (2013.01); *H01L 2224/48227* (2013.01); *H01L 2224/73204* (2013.01); *H01L 2224/73253* (2013.01); *H01L 2224/73265* (2013.01); *H01L 2224/83192* (2013.01); *H01L 2224/83855* (2013.01); *H01L 2224/92125* (2013.01); *H01L 2225/06524* (2013.01); *H01L 2225/06589* (2013.01); *H01L 2924/07811* (2013.01); *H01L 2924/1461* (2013.01); *H01L 2924/15311* (2013.01); *Y10T 428/2852* (2015.01)

(58) Field of Classification Search
CPC ... C09K 11/777; C09K 11/02; C09K 11/7769; H01L 2225/06524; H01L 24/83; H01L 25/0657; H01L 25/50
See application file for complete search history.

(56) References Cited

U.S. PATENT DOCUMENTS

| | | |
|---|---|---|
| 8,376,013 B2 | 2/2013 | Bourke, Jr. |
| 10,074,627 B2 * | 9/2018 | Fathi ................. C09J 11/06 |
| 2003/0096928 A1 | 5/2003 | Chawla et al. |
| 2005/0106907 A1 | 5/2005 | Yamada et al. |
| 2006/0014309 A1 | 1/2006 | Sachdev et al. |
| 2007/0217996 A1 | 9/2007 | Levy et al. |
| 2009/0294692 A1 | 12/2009 | Bourke, Jr. et al. |
| 2012/0089180 A1 | 4/2012 | Fathi et al. |

OTHER PUBLICATIONS

Extended European Search Report dated Jun. 8, 2015 in Patent Application No. 11778432.2.
Office Action dated Jun. 25, 2015 in European Patent Application No. 11778432.2.
Office Action dated Nov. 29, 2018 in European Patent Application No. 11778432.2.
European Office Action dated Aug. 30, 2019, in Patent Application No. 11 778 432.2, 5 pages.

\* cited by examiner

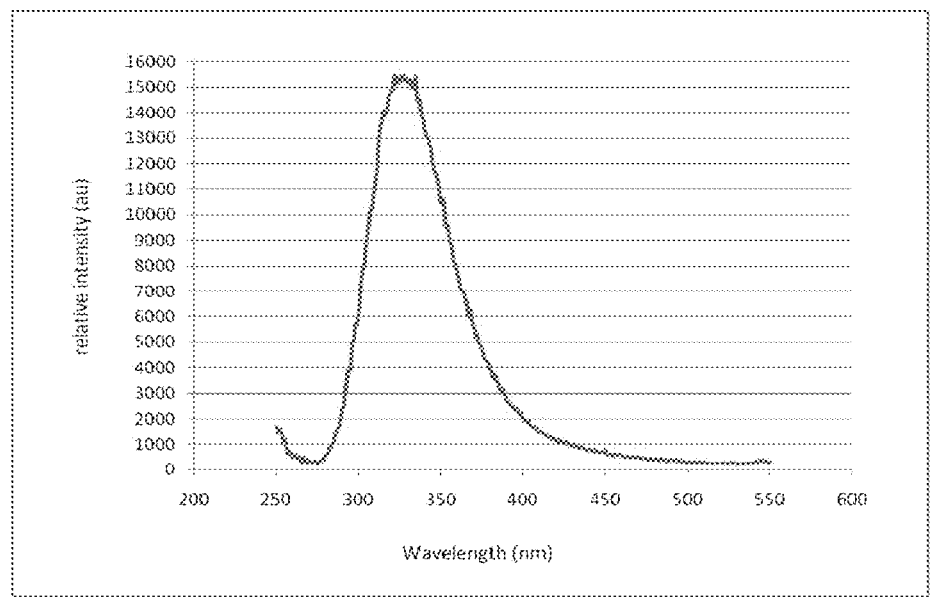
FIG. 1. YTaO₄ was reported to have a peak emission at 337nm under X-ray and was measured during the course of the present invention to emit at 327nm.

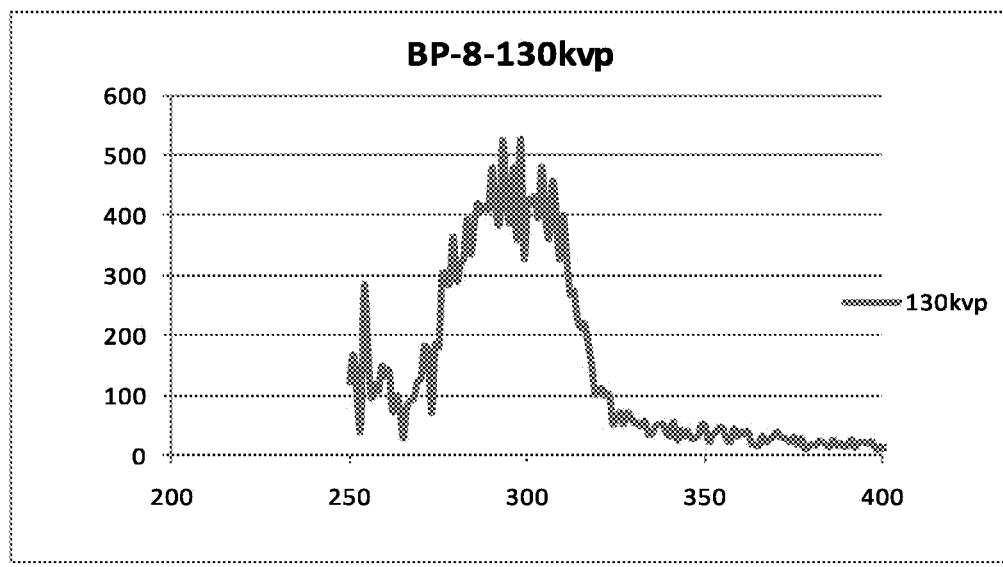
FIG. 2. LaF$_3$:Ce was reported to emit at 280nm under X-ray and was measured during the course of the present invention to emit at 300nm.

FIG. 3. LaOBr:Tm$_3$+ coated with Silica was measured during the course of the present invention to emit in the UVB, UVA and the Visible.

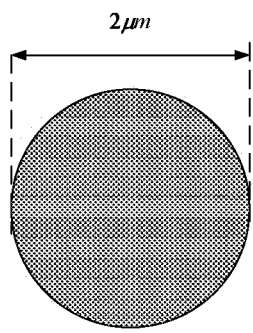
FIG. 11A The silica carrier particle of 2 microns in size
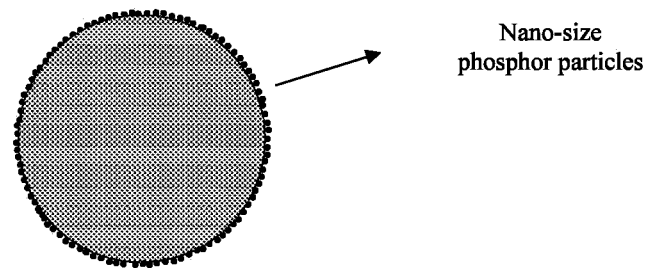
FIG. 11B The silica carrier particle decorated with nano-size particles Figs. 26A-C. A- adhesive dispense. B- UV flashing.
C- top and bottom substrates positioned around the adhesive bondline

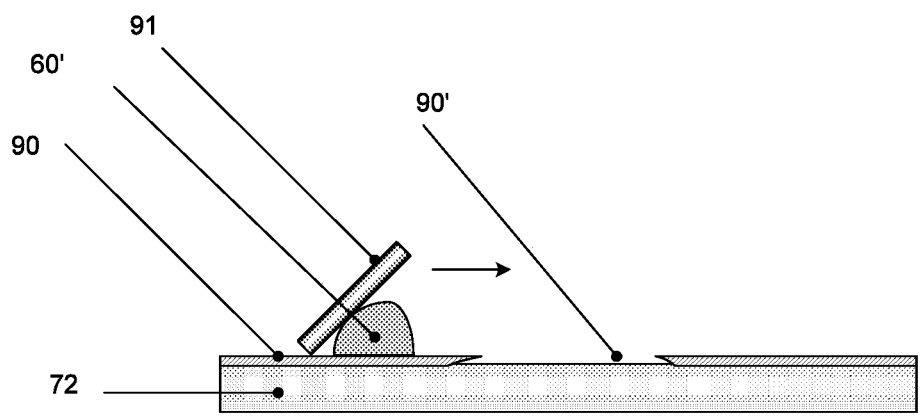
FIG. 30A - Alignment prior to screen printing
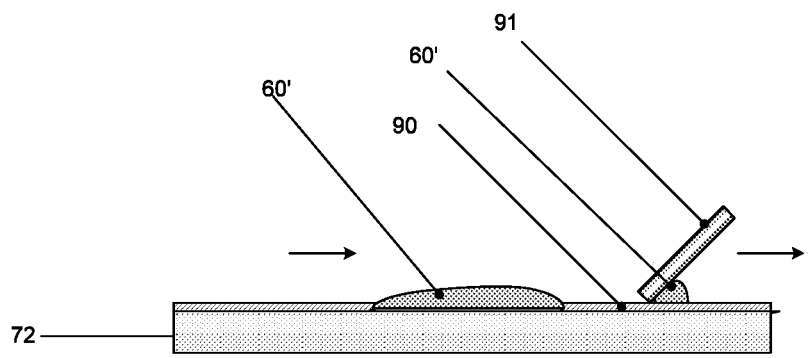
FIG. 30B- Position of the blade post screen printing

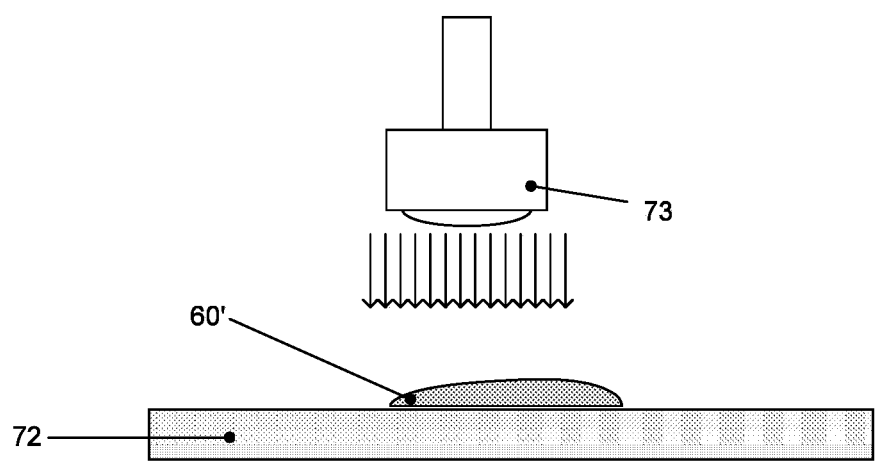
FIG. 30C - adhesive bead after screen printing and being treated under a UV lamp prior to X-ray
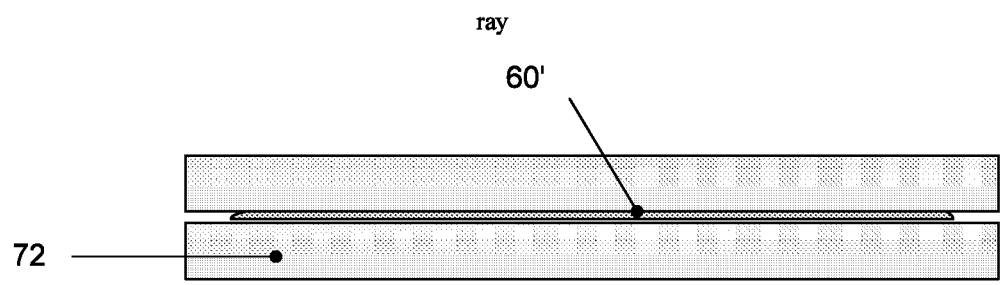
FIG. 30D - Adhesive bead

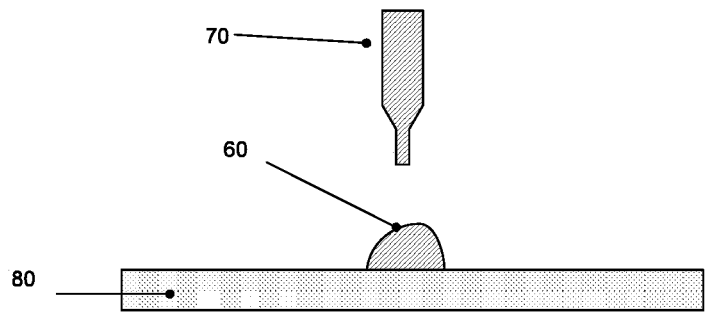
FIG. 31A - Adhesive dispense on composite substrate
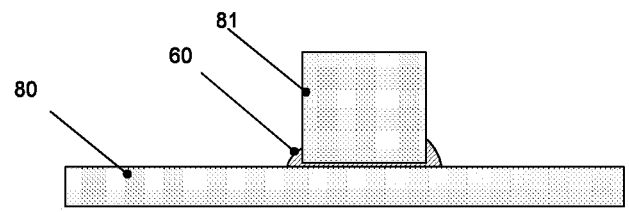
FIG. 31B PET component was place on the adhesive bead
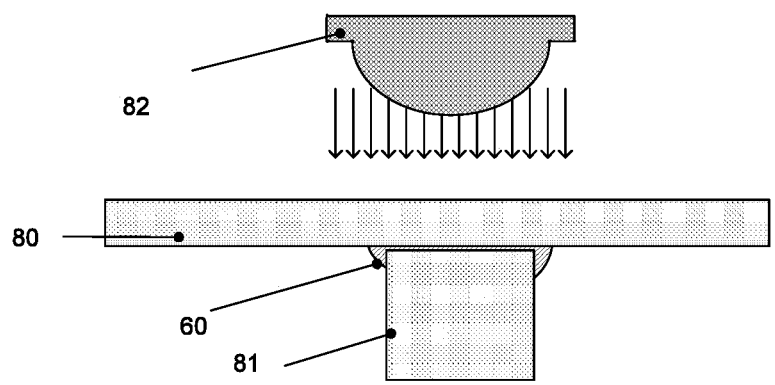
FIG. 31C - The assembly was turned upside down and cure under X-ray at 32-Kvp and 20mA. The X-ray target was Tungsten.

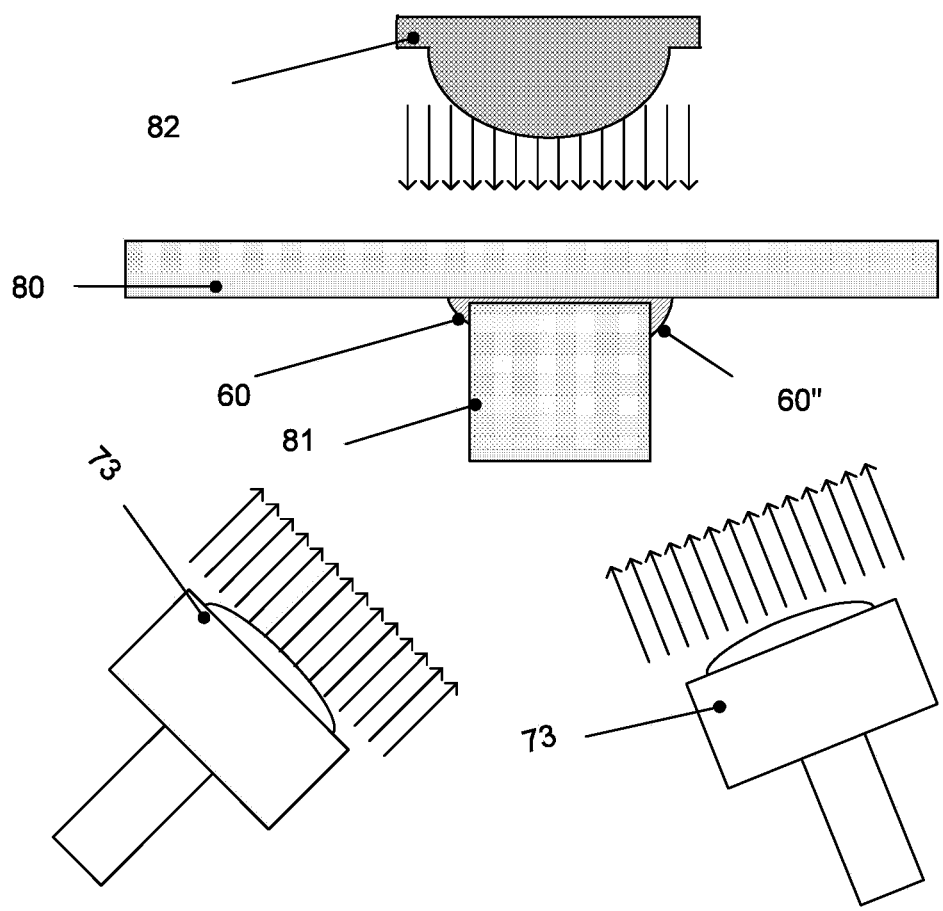
FIG. 32. Additional UV energy added to cure fillets

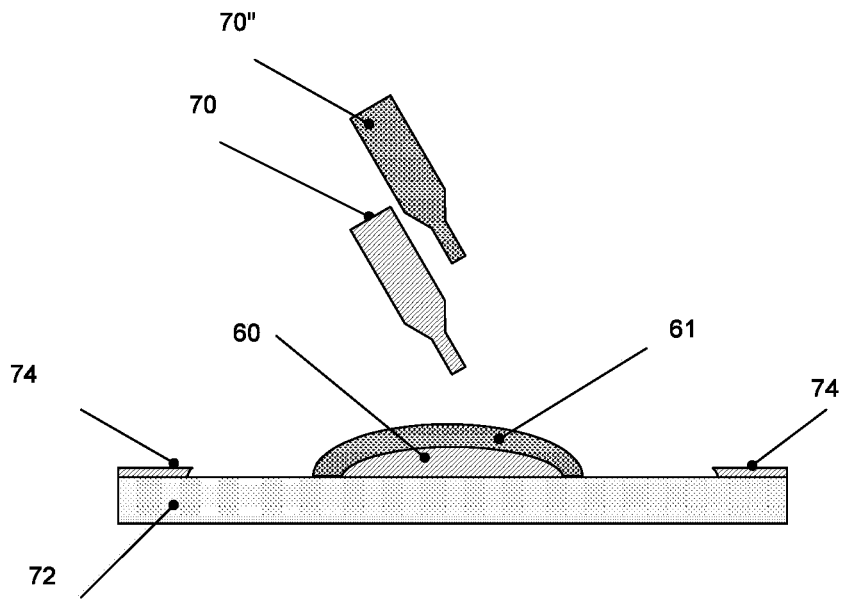
FIG. 33A - Dispensing of 2 adhesive beads
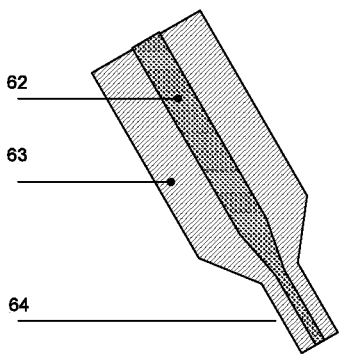
FIG. 33B - Special Dispensing syringe with 2 coaxial containers
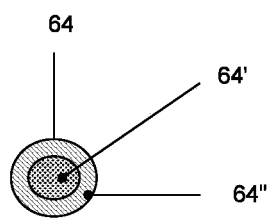
FIG. 33C - Dispensing of 2 adhesive beads through a coaxial needle

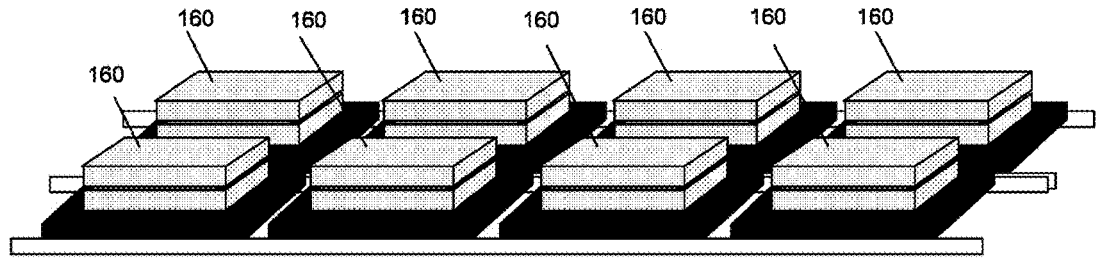
FIG. 35A. Two conveyors are placed side by side to increase the number of parts inside the X-ray system (increased within plane loading)
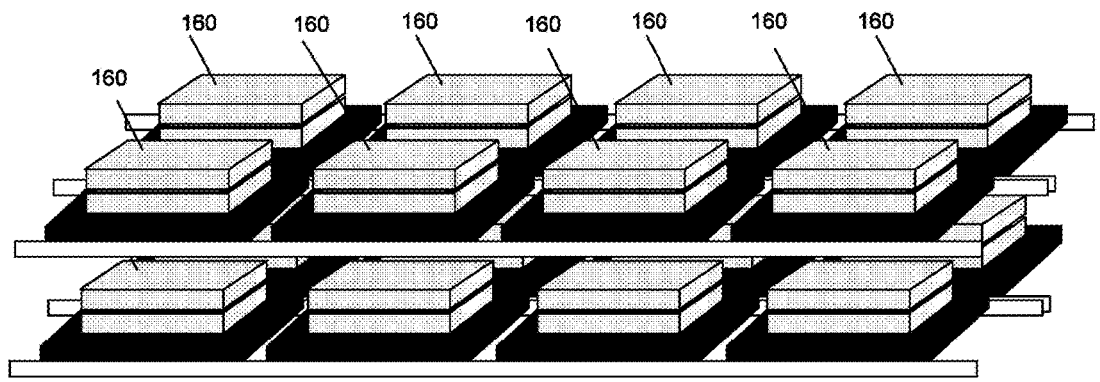
FIG. 35B. Two additional conveyors are placed side by side to increase the number of parts inside the X-ray system (increased cross planes loading)

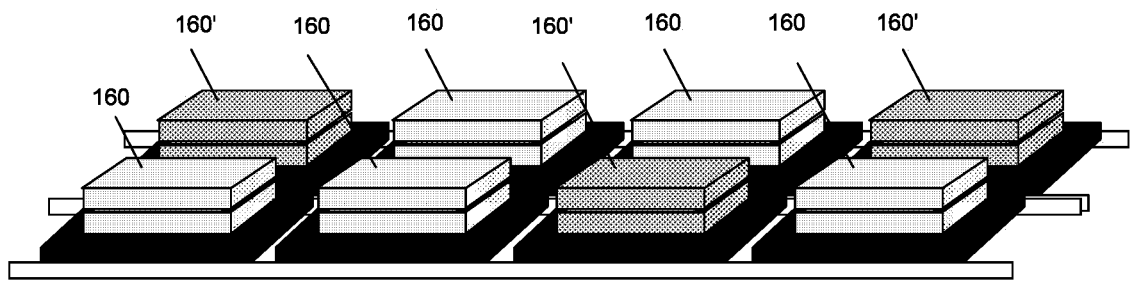
FIG. 36. Alternatively, the X-ray machine can have more than one source.

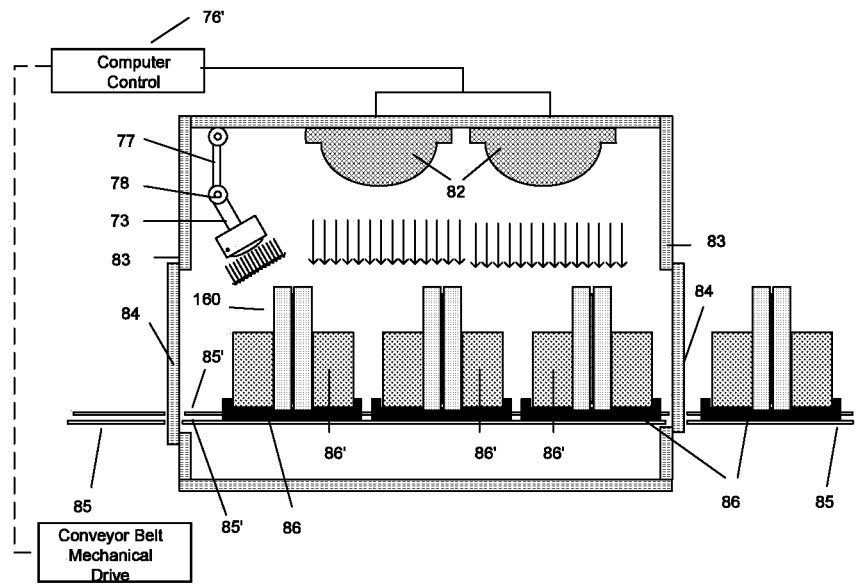
FIG. 37A The assemblies 160 are oriented in the same direction as the X-ray propagation in the vertical plane)
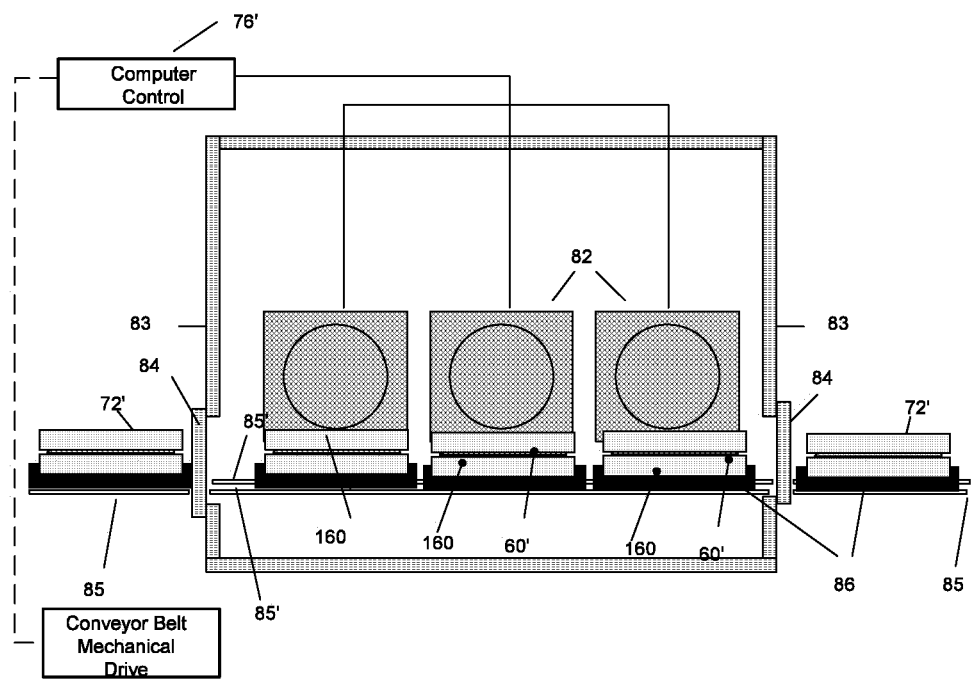
FIG. 37B The assemblies 160 are oriented in the same direction as the X-ray propagation (in the horizontal plane)

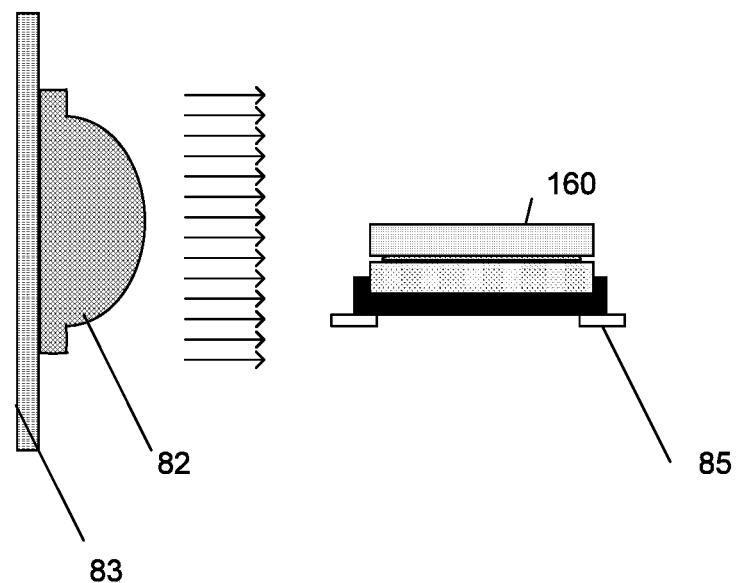
FIG. 37C The assemblies 160 are oriented in the same direction as the X-ray propagation (in the horizontal plane). Perspective along the direction of the conveyor system.

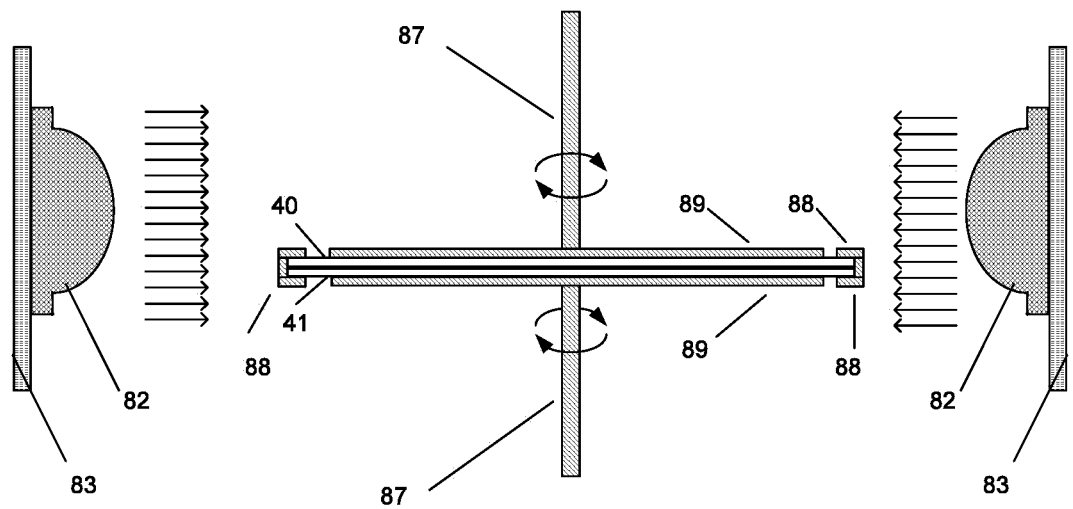
FIG. 38A. Cross section view of the Wafer Bonding Tool
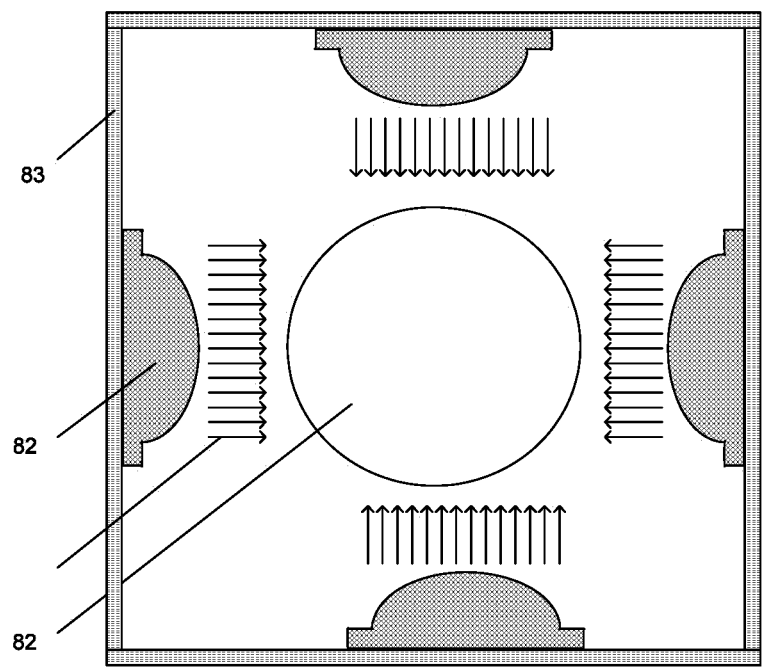
FIG. 38B. Top view of the Wafer Bonding Tool

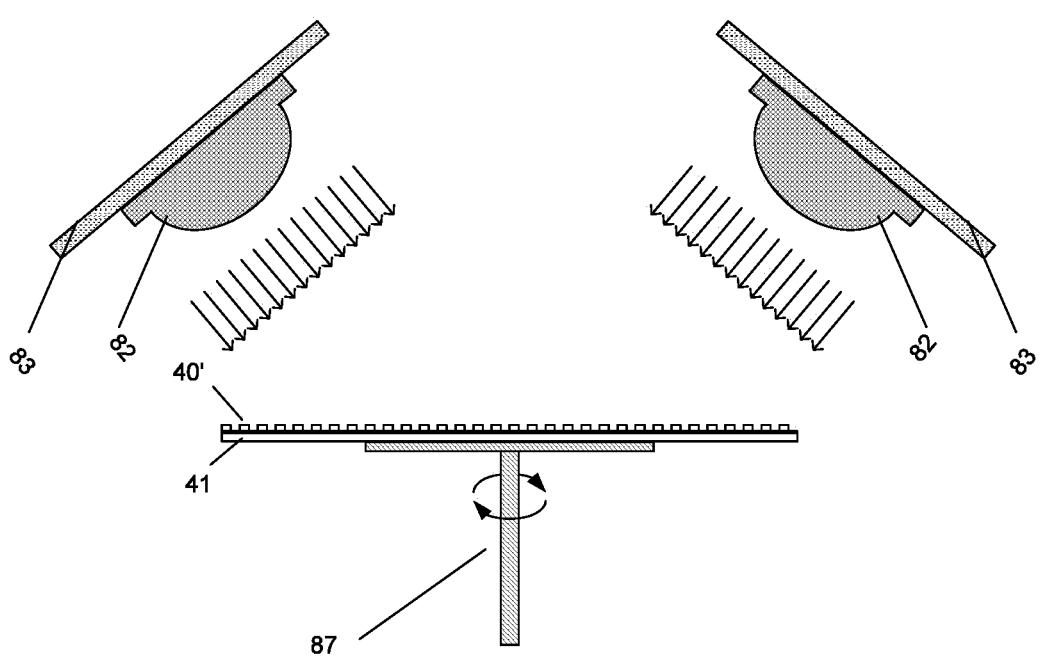
FIG. 39 - Die to wafer bonding tool.

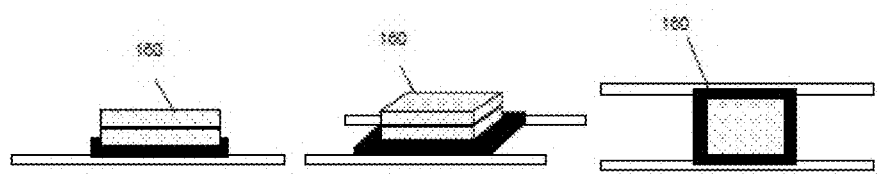
FIG. 40A - Different Perspective of the assemblies 160 interfacing with the conveyor.
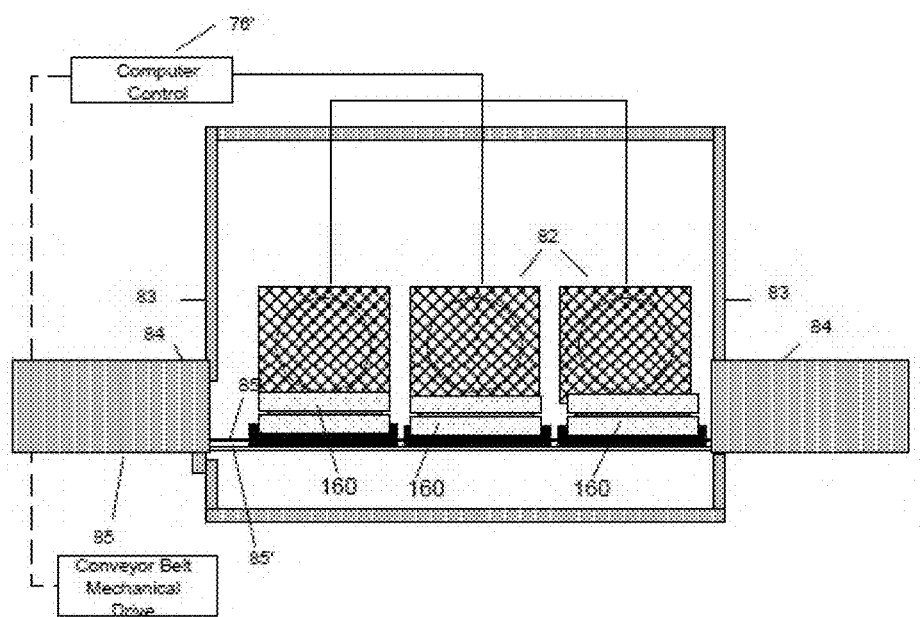
FIG. 40B - assemblies 160 interfacing with the conveyor going through a tunnel that stops leakage of X-ray radiation.

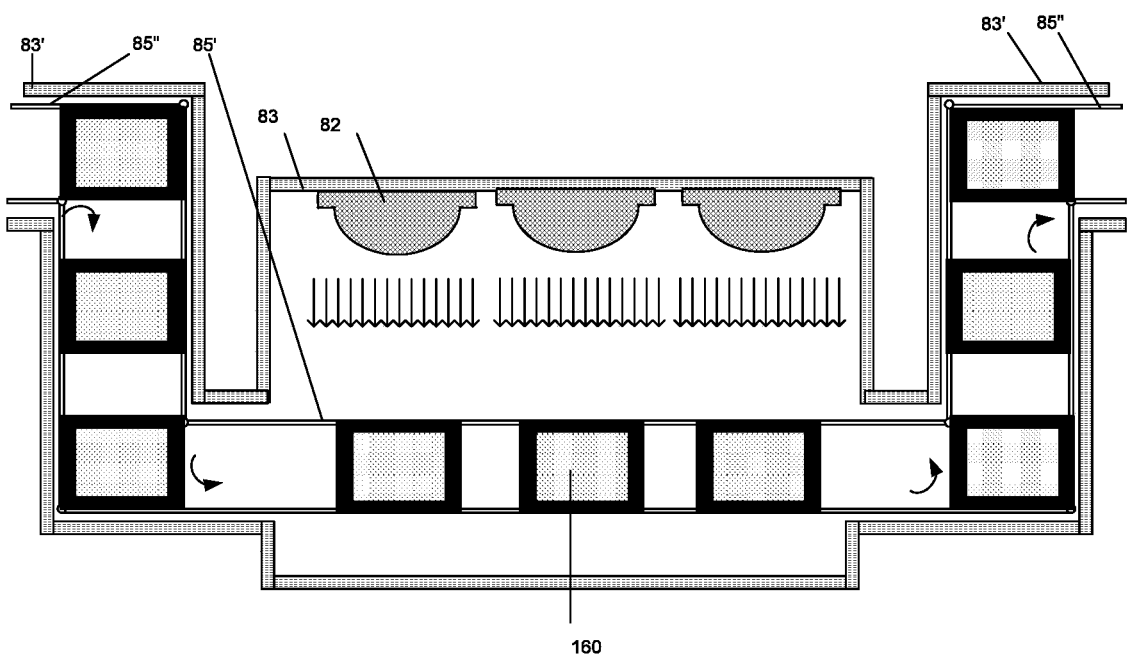
FIG. 40C - assemblies 160 interfacing with the conveyor going through a tunnel that stops leakage of X-ray radiation

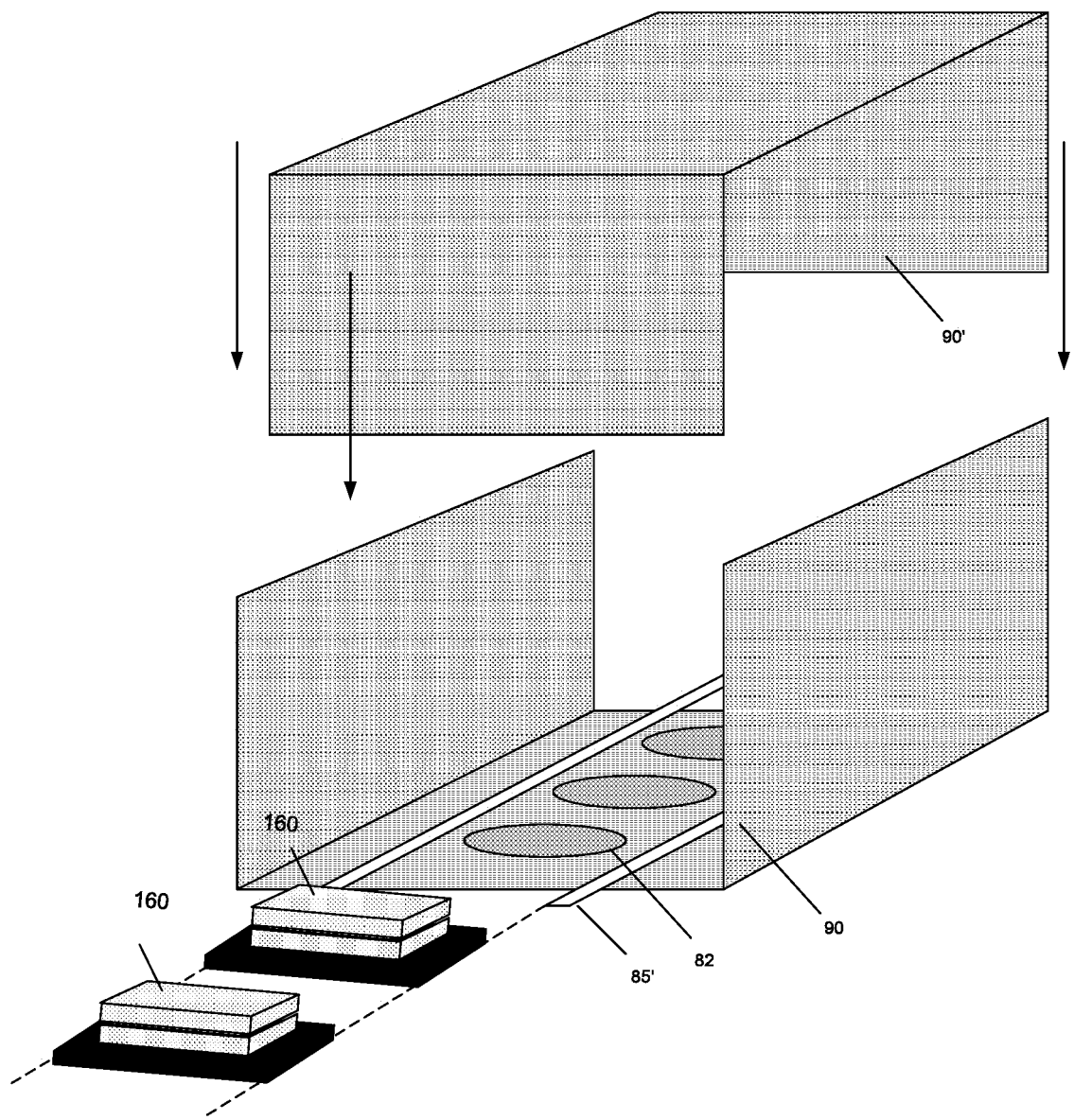
FIG. 41. Contactless chamber design that stops X-ray radiation leakage.

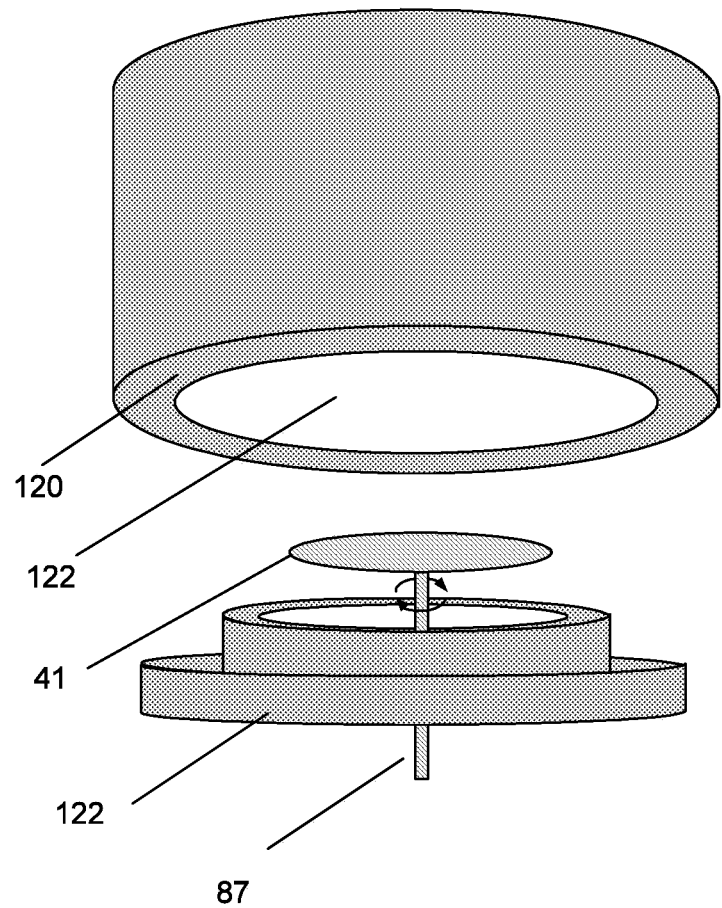
FIG. 42. Contactless chambers that stops X-ray radiation leakage to enable wafer processing in a clean room.

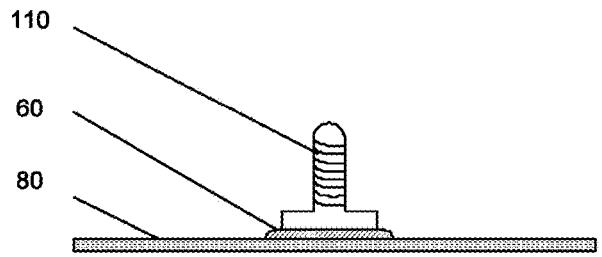
FIG. 43A. An adhesively bonded metallic fasteners to a composite panel
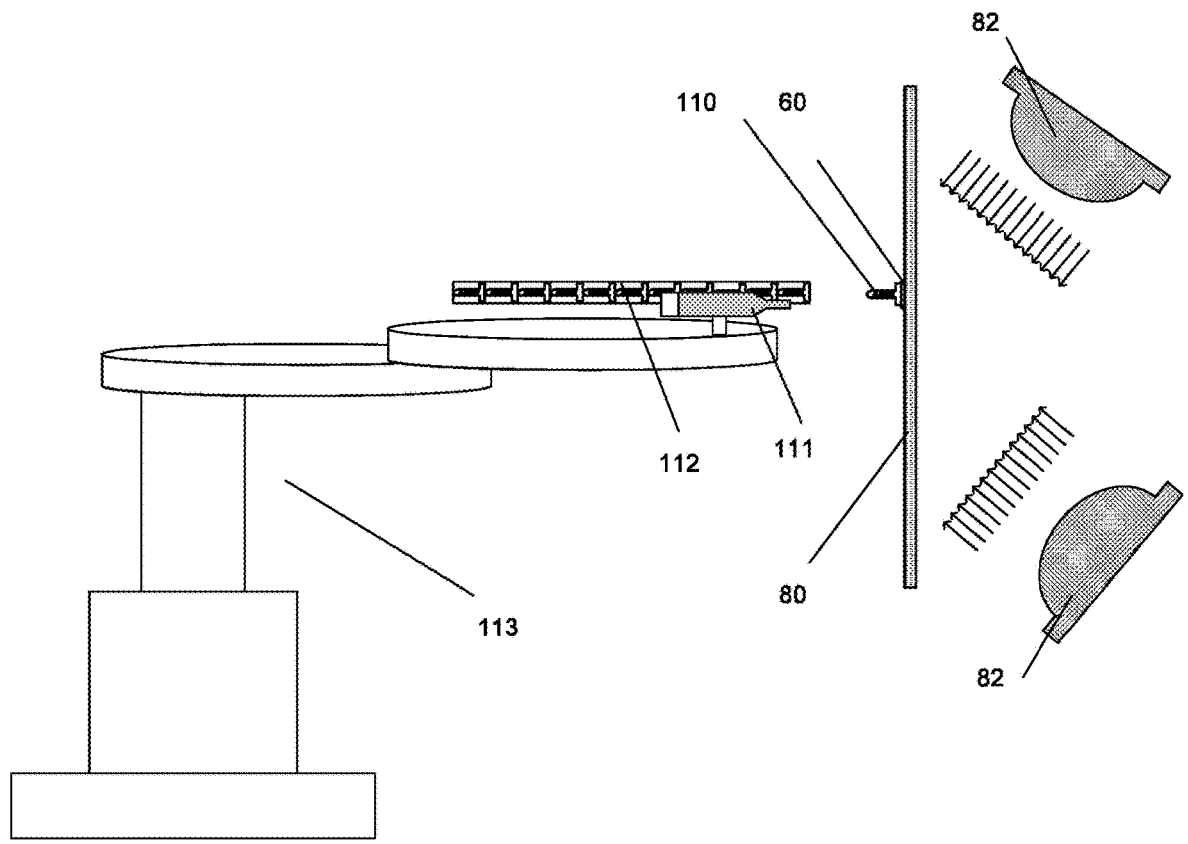
FIG. 43B. A robotic arm can dispense and place metallic components on composite panel 80.

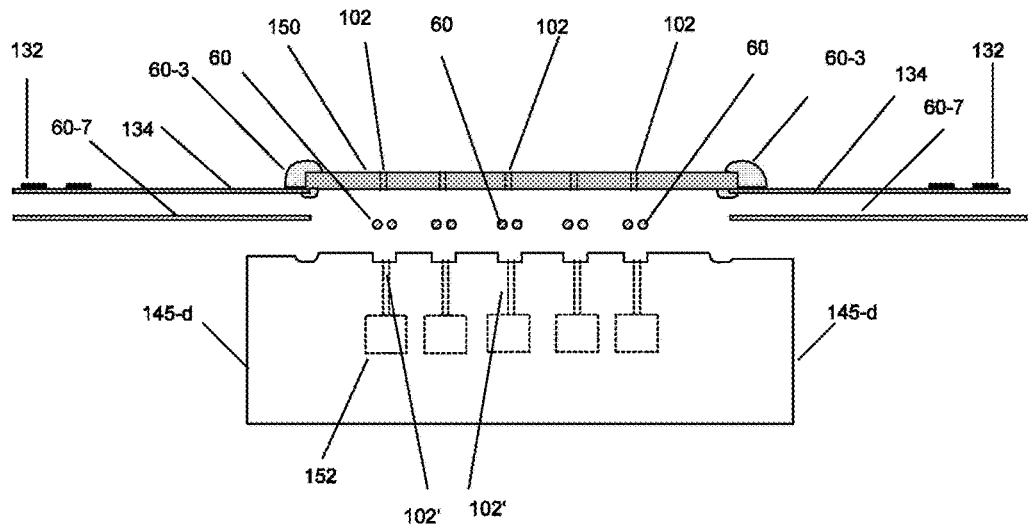
FIG. 55A
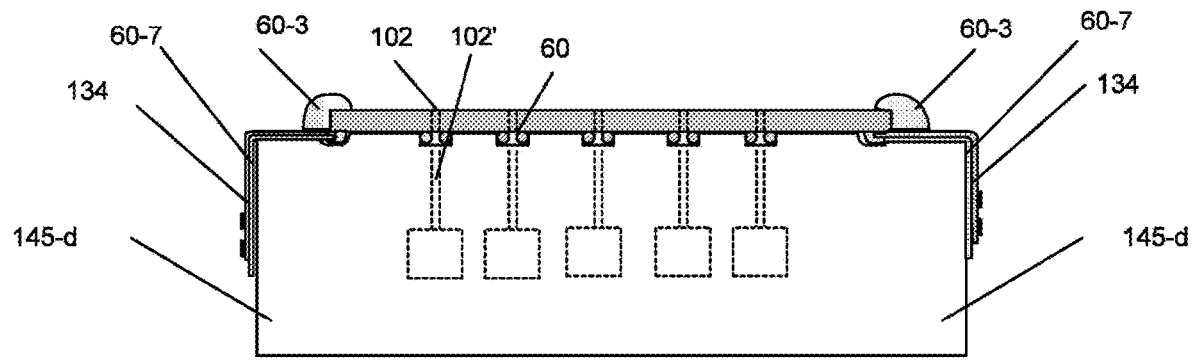
FIG. 55B The flex is adhered to the external walls of the fluidic reservoirs.

ADHESIVE BONDING COMPOSITION AND ELECTRONIC COMPONENTS PREPARED FROM THE SAME

REFERENCE TO RELATED APPLICATIONS

The present application is a Continuation of U.S. application Ser. No. 15/455,573, filed Mar. 10, 2017, now allowed, which is a Continuation of U.S. application Ser. No. 15/382,835, filed Dec. 19, 2016, now U.S. Pat. No. 10,026,711, which is a Divisional of U.S. application Ser. No. 14/593,049, filed Jan. 9, 2015, now U.S. Pat. No. 9,649,832, which is a Divisional of U.S. application Ser. No. 13/102,277, filed May 6, 2011, now U.S. Pat. No. 9,023,249, and also claims priority from U.S. Provisional application Ser. No. 61/331,990, filed May 6, 2010, and U.S. Provisional application Ser. No. 61/443,019, filed Feb. 15, 2011, the entire contents of each of which are hereby incorporated by reference. The present application is also related to U.S. provisional patent application 61/161,328, filed Mar. 18, 2009; U.S. provisional patent application 61/259,940, filed Nov. 10, 2009; U.S. Provisional Application Ser. No. 60/954,263, filed Aug. 6, 2007, and 61/030,437, filed Feb. 21, 2008; U.S. application Ser. No. 12/059,484, filed Mar. 31, 2008; U.S. application Ser. No. 11/935,655, filed Nov. 6, 2007; U.S. Provisional Application Ser. No. 61/042,561, filed Apr. 4, 2008; 61/035,559, filed Mar. 11, 2008; and 61/080,140, filed Jul. 11, 2008; U.S. patent application Ser. No. 12/401,478 filed Mar. 10, 2009; U.S. patent application Ser. No. 11/935,655, filed Nov. 6, 2007; U.S. patent application Ser. No. 12/059,484, filed Mar. 31, 2008; U.S. patent application Ser. No. 12/389,946, filed Feb. 20, 2009; and U.S. patent application Ser. No. 12/417,779, filed Apr. 3, 2009, the entire contents of each of which is hereby incorporated by reference.

BACKGROUND OF THE INVENTION

Field of Invention

The invention pertains to materials and methods for polymer curing, particularly adhesive curing and bonding, and more particularly to methods for using energy conversion and photoinitiator chemistries in applications where access to an external light source is not available and/or where bonding without a coefficient of thermal expansion mismatch is desirable.

Discussion of the Background

Thermosetting polymers and adhesives are well known and are used for a wide variety of applications. One particularly important application domain is in the field of microelectronics assembly, where thermoset adhesives are used to bond bare die to substrate, establish conductive contacts, and perform various roles in packaging and sealing structures such as glob-top and die-underfill structures. Commercially available materials are formulated to meet various requirements, and in addition to the monomer(s) may contain particulate fillers such as metal, oxides, or dielectric powders, as well as various additives to control thermal conductivity, viscosity and other properties. The materials are typically dispensed as a thixotropic fluid in precise locations, and after all the parts are placed, the entire assembly is heated to a temperature necessary to polymerize the monomers or crosslink resins.

As modern electronic components evolve to smaller sizes, and integrated circuits include ever-smaller features such as ultra-shallow junctions, the permissible thermal budget during assembly continues to decrease. New memory device technologies, for example, incorporate phase-change materials that are temperature sensitive and may need to be assembled using low-temperature processing. Similarly, polymer composites used for dental restorations must be cured without subjecting the patient to high curing temperatures. To address these issues, many photo-curing polymer systems have been developed. In general, these systems employ at least one photoinitiator, which, when exposed to UV light, releases chemical energy to form free radicals or cations to initiate the reaction of the monomers at substantially ambient temperatures.

The clear limitation of conventional photoinitiators is the need to have direct line-of-sight access to a suitable light source. This prevents the use of conventional materials for advanced processes such as multilayer stacks of individual silicon dies, because there is no way to get the UV light into the interior of the stack.

Furthermore, the conventional UV curable adhesives cure from the outside surface of an adhesive bead to the inside of the adhesive bead; and, in most cases curing is accompanied by the formation of a skin. In the present invention curing is more controllable and can proceed across the entire volume of the adhesive bead.

SUMMARY OF THE INVENTION

One object of the present invention is to provide polymer formulations (i.e. monomers, photoinitiators, and energy converters) that can be cured by indirect photoinitiation, i.e. in the absence of line-of-sight access to the external energy source.

A further object of the present invention is to provide an adhesive composition that may be cured at ambient temperature.

Another object of the present invention is to provide a flowable adhesive composition containing a photoinitiator and an energy converter, preferably a downconverter such as a phosphor or scintillator material (or a combination of a phosphor and a scintillator material).

Another object of the present invention is to provide a flexible sheet adhesive material capable of being polymerized by selected ionizing radiation.

Another object of the present invention is to provide a method for adhesive bonding at ambient temperature, as well as a method of adhesive bonding suitable for bonding silicon dies or wafers in a stack at ambient temperature, along with a wide variety of other end uses.

These and other objects and advantages of the invention, either alone or in combinations thereof, have been satisfied by the discovery of a curable adhesive composition comprising:

a polymerizable or crosslinkable organic vehicle comprising at least one polymerizable monomer or a plurality of crosslinkable polymer chains;

at least one photo-initiator responsive to a selected wavelength of light; and, at least one energy converting material selected to emit said wavelength of light when exposed to a selected imparted radiation;

and its use in preparation of various assemblies and constructions.

BRIEF DESCRIPTION OF THE FIGURES

Various other objects, features and attendant advantages of the present invention will be more fully appreciated as the same becomes better understood from the following detailed description when considered in connection with the accompanying drawings in which like reference characters designate like or corresponding parts throughout the several views and wherein:

FIG. 1 provides an emission spectrum of a material that emits in the UVA regime, upon irradiation with X-rays.

FIG. 2 provides an emission spectrum of a material that emits in the UVB regime, upon irradiation with X-rays.

FIG. 3 provides an emission spectrum of a material that emits in the UVA, UVB, and visible regimes, upon irradiation with X-rays.

FIGS. 11A and 11B show a representation of a bare silica carrier particle and a silica carrier particle decorated with nano-size phosphor particles, respectively.

FIGS. 30A-D provide representations of an embodiment of the present invention whereby a screen printer is used for application of the adhesive composition and UV flashing is used to effect a partial cure prior to application of the second substrate and irradiation with X-rays.

FIGS. 31A-C provide representations of an embodiment of the present invention bonding a PET component to a cross-ply carbon composite component.

FIG. 32 provides a representation of an embodiment of the present invention whereby fillets having direct line-of-sight are further cured by direct application of UV energy.

FIGS. 33A-C provide representations of an embodiment of the present invention whereby the 2 adhesives are administered either through separate dispensers (FIG. 33A) or through 2 coaxial dispensers (FIGS. 33B-C).

FIGS. 35A and 35B provide representations of embodiments of conveyor systems for use in the present invention.

FIG. 36 provides a representation of an embodiment of the present invention using more than one X-ray source for curing of different assemblies at the same time.

FIGS. 37A-C provide representations of different embodiments of the method of the present invention whereby the workpiece being irradiated is oriented in different ways with respect to the radiation source.

FIGS. 38A and 38B provide representations of an embodiment of the present invention of a wafer bonding tool having a rotating table and rotating arm.

FIG. 39 provides a representation of an embodiment of a die to wafer bonding tool that can be used in the present invention.

FIGS. 40A-C provide representations of different embodiments of X-ray systems and conveyor systems useful in the present invention.

FIG. 41 provides a representation of an embodiment of a contactless chamber design useful in the present invention.

FIG. 42 provides a representation of a further embodiment of a contactless chamber design useful in the present invention.

FIGS. 43A-B provide representations of embodiments of the present invention for bonding fasteners to a composite panel.

FIGS. 55A and 55B provide representations of use of an embodiment of the present invention in connecting an active device to a fluidic reservoir.

DETAILED DESCRIPTION OF THE INVENTION

Figure 4:
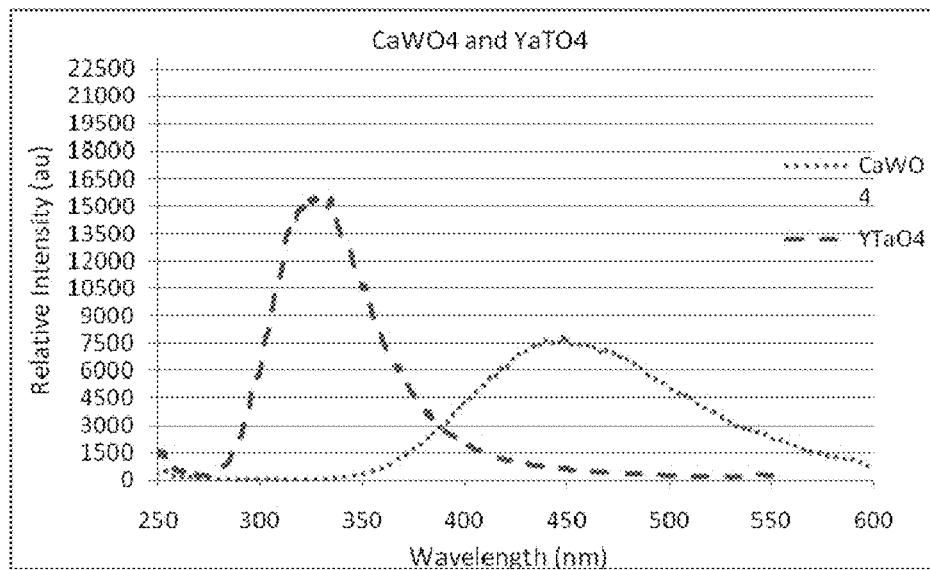
FIG. 4 provides emission spectra of two separate materials, $CaWO_4$ and $YaTO_4$, upon irradiation with X-rays.

A new class of curable adhesives is provided by the present invention. This new class of adhesives has one or more of the following desirable attributes:

a—Cure without line of sight (bond line where the adhesion takes place is internal to structures to be bonded)

b—Cure without depth of penetration limitation (Bond line can be deep inside materials without compromising the cure kinetics)

c—Cure without thermal expansion mismatch (ability to bond at room temp and to avoid compressive and tensile stresses at the bond line)

d—Cure adhesive selectively (only where the adhesive has an energy converting particle does the adhesive form a network; this can be used to generate selective curing geometries)

e—The adhesives have suitable Properties (electrical—including dielectric non-conductive to anisotropically semiconductive to conductive, mechanical—rigidity or compliancy (use of a second phase flexibilizer), optical—from transparent to opaque, Acid vs. Base Control—ability to withstand a variety of environments from Inks to aqueous solutions, Adhesive Bond strength of a desirable range)

These attributes make it possible to achieve certain adhesive curing applications which were not previously attainable, as well as improve on already existing adhesive curing applications. The present invention adhesive curing leads to novel assemblies and processing methods that are advantageous compared to the state of the art.

In one embodiment, the present invention provides a way to bond materials at ambient temperature using photoinitiator chemistries that convert absorbed light energy (typically UV light) to chemical energy in the form of initiating species such as free radicals or cations and thereby initiate a polymerization reaction in a monomer-containing adhesive. In another aspect, the invention provides a way to perform photo-initiation in situations where the area to be bonded is not accessible to an external light source.

According to one embodiment of the invention, the adhesive composition comprises: an organic vehicle comprising at least one polymerizable monomer; at least one photoinitiator responsive to a selected wavelength of light; and, at least one energy converting material selected to emit the selected wavelength of light when exposed to a selected imparted radiation.

According to another aspect of the invention, the method of adhesive bonding comprises the steps of: a) placing a polymerizable adhesive composition, including at least one photoinitiator and at least one energy converting material, in contact with two or more components to be bonded to form an assembly; and, b) irradiating the assembly with radiation at a first wavelength, capable of conversion by the at least one energy converting material, preferably a down converting material such as a phosphor, to a second wavelength capable of activating the at least one photoinitiator.

According to yet another aspect of the invention, the method of adhesive bonding comprises the steps of: a) attaching the at least one photoinitiator and at least one energy converting material with one another using such methods as adsorption or chemical bonding through a tether and then mixing the chemistry hence formed into the mix with a resin.

According to a further embodiment of the invention, a method for creating joints and establishing adhesion between 2 different substrates comprises using an adhesive system that in turn contains a plurality of synthetic polymeric chains and at least one photoinitiator that is a photo-active cross-linking agent. In this case the role of the at least one photoinitiator as a photo-active cross-linking agent is to link one polymer chain to another by forming bonds that can be covalent or ionic in nature. In this case the initial viscous material is transformed to a solid material through the formation of a 3D network structure achieved by creating links between pre-existing chains in a resin system. Such cross-linking can be applicable to both synthetic polymers (for adhesives) and to natural polymers (such as protein or DNA).

The inventive material of one embodiment of the present invention comprises two primary components: first, a monomer composition including at least one photoinitiator; and second, at least one energy converting material capable of absorbing an imparted energy and converting the energy to produce photons in a spectral range that can be absorbed by the at least one photoinitiator, and thus initiate polymerization of the monomer composition. Preferably, the energy converting material is a downconverting material capable of absorbing higher-energy photons (typically X-rays) and down-converting to produce lower-energy photons (typically UV, but also visible light) in a spectral range that can be absorbed effectively by the photoinitiator. Optional components include, without limitation: organic and inorganic fillers such as oxides, dielectrics, conductors, fibers, etc.; plasticizers; pore-formers; and other physical additives.

In an alternative embodiment, the curable adhesive composition comprises a plurality of cross-linkable polymer chains rather than the polymerizable monomer. In this embodiment, the photoinitiator is one that is capable, upon activation, of creating crosslinks between the cross-linkable polymer chains to form a 3D polymer network, thus curing the adhesive composition by crosslinking. While many of the embodiments below are described based upon the embodiment using a curable adhesive composition comprising polymerizable monomer, this description is merely for convenience and use of the curable adhesive composition comprising the plurality of cross-linkable polymer chains can be equally substituted in the described embodiments.

In the present invention, the energy converting material can be any material that can convert the imparted energy either into higher energy photons ("upconverting material") or into lower energy photons ("downconverting material"). Suitable upconverting materials and downconverting materials are described in U.S. provisional patent application 61/161,328, filed Mar. 18, 2009; U.S. provisional patent application 61/259,940, filed Nov. 10, 2009; U.S. Provisional Application Ser. No. 60/954,263, filed Aug. 6, 2007, and 61/030,437, filed Feb. 21, 2008; U.S. application Ser. No. 12/059,484, filed Mar. 31, 2008; U.S. application Ser. No. 11/935,655, filed Nov. 6, 2007; U.S. Provisional Application Ser. No. 61/042,561, filed Apr. 4, 2008; 61/035,559, filed Mar. 11, 2008; and 61/080,140, filed Jul. 11, 2008; U.S. patent application Ser. No. 12/401,478 filed Mar. 10, 2009; U.S. patent application Ser. No. 11/935,655, filed Nov. 6, 2007; U.S. patent application Ser. No. 12/059,484, filed Mar. 31, 2008; U.S. patent application Ser. No. 12/389,946, filed Feb. 20, 2009; and U.S. patent application Ser. No. 12/417,779, filed Apr. 3, 2009, the entire disclosures of each of which are hereby incorporated by reference. The imparted energy can be any desired energy as needed to penetrate the material between the imparted energy source and the adhesive composition itself. For example, the imparted energy can be near-infrared (NIR), with an upconverting material to convert the imparted energy into UV photons that can be absorbed by the photoinitiator used. Preferably, the imparted energy is X-ray energy, with the energy converting material being a downconverting material, such as a phosphor or scintillator. For convenience, the following discussion will refer to downconverting materials and the use of X-rays as the imparted energy. However, this is not intended to be limiting of the present invention and any desired combination of imparted energy and energy converting material can be used, so long as the photons generated by the energy converting material are capable of being absorbed by the photoinitiator.

The associated method comprises two essential steps: a) placing a polymerizable adhesive composition, including a photoinitiator and down-converting material, in contact with two or more components to be bonded to form an assembly; and, b) irradiating the assembly with radiation at a first wavelength, capable of down-conversion by the phosphor to a second wavelength capable of activating the photoinitiator. Optional steps include, without limitation: dispensing the adhesive in a selected pattern through a needle or screen printing the adhesive through a mask having a selected pattern; photo-patterning the adhesive; pre-forming the adhesive into a sheet having isotropic or anisotropic conductivity; and applying pressure to the adhesive bond during the curing process.

The dispensing of the adhesive and the adhesive properties can preferably be adjusted to meet the following:

The dispensing can be performed using any conventional dispensing system, including, but not limited to, dispensing using piston or auger pumps, spin coating, spray coating, or screen printing.

The adhesive can contain a tracer element for inspection, if desired.

The adhesive can contain a pigment for optical inspection, if desired.

The adhesive can be made to change color after curing, if desired.

For reference purposes, listed below are generally accepted approximate wavelength, frequency, and energy limits of the various regions of the electromagnetic spectrum:

|  | Wavelength (m) | Frequency (Hz) | Energy (J) |
| --- | --- | --- | --- |
| Radio | $>1 \times 10^{-1}$ | $<3 \times 10^9$ | $<2 \times 10^{-24}$ |
| Microwave | $1 \times 10^{-3}\text{-}1 \times 10^{-1}$ | $3 \times 10^9\text{-}3 \times 10^{11}$ | $2 \times 10^{-24}\text{-}2 \times 10^{-22}$ |
| Infrared | $7 \times 10^{-7}\text{-}1 \times 10^{-3}$ | $3 \times 10^{11}\text{-}4 \times 10^{14}$ | $2 \times 10^{-22}\text{-}3 \times 10^{-19}$ |
| Optical | $4 \times 10^{-7}\text{-}7 \times 10^{-7}$ | $4 \times 10^{14}\text{-}7.5 \times 10^{14}$ | $3 \times 10^{-19}\text{-}5 \times 10^{-19}$ |
| UV | $1 \times 10^{-8}\text{-}4 \times 10^{-7}$ | $7.5 \times 10^{14}\text{-}3 \times 10^{16}$ | $5 \times 10^{-19}\text{-}2 \times 10^{-17}$ |

-continued

| | Wavelength (m) | Frequency (Hz) | Energy (J) |
|---|---|---|---|
| X-ray | $1 \times 10^{-11}$-$1 \times 10^{-8}$ | $3 \times 10^{16}$-$3 \times 10^{19}$ | $2 \times 10^{-17}$-$2 \times 10^{-14}$ |
| Gamma-ray | $<1 \times 10^{-11}$ | $>3 \times 10^{19}$ | $>2 \times 10^{-14}$ |

Several application domains can benefit from this new class of adhesive and methods used to cure such new class of adhesives and these include:

Bonding Of Semiconductors such as wafer bonding, die to wafer bonding, die on die bonding, package on package assembly at room temperature, etc. This is a particularly useful area for anisotropically conductive adhesives.

Encapsulation Of Semiconductors: Such as glob top, dam and fill, molding (PMC), insertion molding and flip chip underfill.

Semiconductor lithography: the present invention adhesive compositions and corresponding constituent material chemistries can be used in front end semiconductors to pattern gate structures. The photolithography applications include the use of photoresist materials that have negative or positive tones and development. The exposure of X-rays can be gated by adjustable apertures (particularly those made from lead), with programmable distances to allow X-rays to interact with specific areas of the dispensed adhesive. Furthermore, patterning using X-rays can be performed by masks containing heavy metals that attenuate X-ray in some areas and not others.

Other methods of patterning can bypass all mask work by using imprint lithography. In this case, dip transfer methods and stamping methods can be used to deposit a pattern that contains the adhesive composition with features containing energy converting particles. In this case X-ray would cure the adhesive areas with the conversion particles contained within.

The present invention also provides the ability to prepare novel composites. A novel ply (the fundamental Building Block for composites) contains fibers coated with polymer resins, energy converting particles and suitable catalyst/photoinitiator systems. This novel prepreg material is used for the build up process (Cross-ply, unidirectional ply) used in composites to yield light weight structures and shapes ranging from simple shapes to complex 3D shapes and structures (such as a round vessel). The stack up or build up is then exposed to X-ray for curing and solidification.

Bonding Of Composites: Bonding of composites to other composites, to metals and metal alloys, to rubbers, to leather and to inorganic materials (such as ceramics), particularly useful in bonding of non-like materials to one another.

Attaching mechanical fasteners to composites: Bonding of small metallic components to large composite panels such as rivets can be useful to fasten 2 separate structures. Conventionally, this requires the use of metal on metal contact to accomplish a welded connection. The present invention adhesives enable much wider manufacturing freedom of operation. For aerospace and automotive applications, for example, a KUKA robot (sold by KUKA Aktiengesellschaft of Augsburg, Germany) can be equipped with an adhesive applicator (such as a dispenser) and an X-ray source as well as a pick and place machine to: dispense the adhesive, perform optical inspection, place a rivet and hold it in place, and cure with X-ray, all within a record time compared to any other known methods. Furthermore, the advantage of room temperature bonding minimizes warpage.

Natural composites: The fabrication of large wood beams, or other natural composite materials, is conventionally accomplished, for example, from small wood pieces by resin coating the wood pieces and bonding the assembly under high pressure and heat to cure the adhesive. The present invention adhesives allow room temperature bonding and no moisture needs to be volatized during cure. This is far better than the conventional methods of making such composites which typically use microwaves for heat generation, but creates enormous amounts of heat in the process, sometimes even resulting in the workpiece catching fire!

Bonding Of Metals: bonding metallic chassis and doors in automotives (to replace conventional induction heating). Metal sheets are bent in special shapes and then adhesively bonded together by first dispensing a bead around the chassis and mating the metallic pieces, fixing their position, followed by curing using the present invention method and composition.

Fluidic Channels: Creation of fluidic channels in plastics, metals and inorganic substrates by bonding patterned substrates together to form said fluidic channels. The joining of dissimilar plastics, the joining of semiconductors to plastic can be done without the mismatch induced by thermal expansion.

Multichip Modules: Die on KOVAR substrate, as well as lid sealing on multi-chip-modules.

MEMS: Sealing MEMS with glass wafers at room temperature (without head shift).

Optoelectronics: Alignment for maximizing light intensity yield (DWDM) and apply adhesive and cure at room temperature (maintain maximum light intensity passage). Align fiber in V-groove and cure and align multi-channels fibers and cure while maintaining light intensity passage.

Attaching deformable substrates, particularly dissimilar substrates: Attaching rubber to foam, leather to rubber, leather to leather, or fabric to fabric, or any combination of deformable substrates.

Other preferred applications of the present invention adhesives technology include, but are not limited to:
  Adhesive bonding of living tissue, not only at the surface but internally. This eliminates the need for sutures or staples. Currently, cyanoacrylate ("SuperGlue") type adhesives are used for these applications. However, cyanoacrylates generally generate heat as they cure, which can lead to cell ablation.
  Activation of a coagulant to treat bleeding—most valuable in a trauma or extensive surgery. The present invention adhesives could be used as temporary "stopgap" measures in trauma patients, giving the caregiver more time to address injuries without the patient bleeding out.
  Remote curing of construction materials, best suited for local repair with a uniform cure throughout the articles to be cured.
  Bonding of fabrics such as foul weather gear, without heat, eliminating melting created at a heat bond, and the need for putting (stitch) holes into impervious materials.

One particularly preferred application domain is in the field of microelectronics assembly, where thermoset adhesives are used to bond bare die to substrate, establish conductive contacts, and perform various roles in packaging and sealing structures such as glob-top and die-underfill structures. Commercially available materials are formulated to meet various requirements, and in addition to the monomer(s) may contain particulate fillers such as metal or dielectric powders, as well as various additives to control viscosity and other properties. The materials are typically dispensed as a thixotropic fluid in precise locations, and after all the parts are placed, the entire assembly is heated to a temperature necessary to polymerize the monomers. The present invention avoids the need to use such heating and can generate curing of the adhesive without risking warpage or other heat damage to the microelectronics.

As modern electronic components evolve to smaller sizes, and integrated circuits include ever-smaller features such as ultra-shallow junctions, the permissible thermal budget during assembly continues to decrease. Similarly, polymer composites used for dental restorations must be cured without subjecting the patient to high curing temperatures. To address these issues, many photo-curing polymer systems have been developed. In general, these systems employ a photoinitiator, which, when exposed to UV light, releases chemical energy in the form of free radicals or cations to initiate the reaction of the monomers at substantially ambient temperatures.

The clear conventional limitation of photoinitiators is the need to have direct access to a suitable light source. This prevents the use of conventional materials for advanced processes such as multilayer stacks of individual silicon dies, because there is no way to get the UV light into the interior of the stack. These limitations are not present with the present invention adhesives, since the present invention adhesives can be readily cured by application of ionizing radiation, such as X-rays to cure the adhesive in place with minimal heat generated.

In the description that follows, various aspects of the invention will be described in greater detail so that the skilled artisan may gain a fuller understanding of how the invention may be made and used. Although the present description discusses the use of X-ray as the triggering radiation for the curing process, other types of ionizing radiation can be used as the triggering radiation, using similar down-converting agents, including, but not limited to, gamma rays or particle beams, such as proton beams or electron beams.

CTE—Mismatch

The mismatch between the coefficients of thermal expansion of different materials can be illustrated through the following table. The present invention enables joining materials without heat and hence circumvents the stresses that are typically trapped during thermal heating necessitated by thermal curing adhesives. The current invention enables curing between materials of drastically different CTEs.

| Material | Coefficient OF Thermal Expansion/ppm/C. |
|---|---|
| Silica Glass | 0.6 |
| E-Glass | 4.8 |
| Alumina | 8.7 |
| Steel | 14 |
| Aluminum | 23-24 |
| Polyimide | 38-54 |
| Epoxy | 45-65 |
| Polyester | 55-100 |
| Polystyrene | 60-80 |
| Polypropylene | 85-200 |
| Silicone resin | 160-180 |

Photoinitiators

The first essential component of the inventive material is a monomer system including a photoinitiator. The radical polymerization of formulations based on acrylate or styrene has been widely developed. It typically relies on radiation curing using near UV (300-400 nm range), although photoinitiators are now available in the visible up to the IR range as well as into the deep UV range. Cationic photoinitiators, which produce either a Lewis or Bronsted acid, may be used as initiators for cationically polymerizing materials (e.g., epoxies) and for resins that are capable of crosslinking via polycondensation reactions.

Photoinitiators are typically divided into two classes: Type I photoinitiators which undergo a unimolecular bond cleavage when irradiated, yielding free radicals, and Type II photoinitiators which undergo a bimolecular reaction, in which the excited state of the photoinitiator interacts with a second molecule (called a coinitiator) to generate free radicals. UV photoinitiators may be of either Type I or Type II, whereas visible light photoinitiators are almost exclusively Type II.

Type I UV photoinitiators include, but are not limited to, the following classes of compounds: benzoin ethers, benzil ketals, α-dialkoxyacetophenones, α-aminoalkylphenones, and acylphosphine oxides. Type II UV photoinitiators include, but are not limited to, benzophenones/amines and thioxanthones/amines. Visible photoinitiators include, but are not limited to, titanocenes.

It will be appreciated that the most efficient system will be one in which the particular photoinitiator is selected based on two considerations, viz., the type of monomer system and the type of light available.

A large number of useful photoinitiator compounds are known in the art. The following compounds [available from Sigma-Aldrich Corp., St. Louis, Mo.] have been characterized and their UV absorbance spectra are available: Acetophenone, 99%; Anisoin, 95%; Anthraquinone, 97%; Anthraquinone-2-sulfonic acid, sodium saltmonohydrate, 97%; (Benzene) tricarbonylchromium, 98%; Benzil, 98%; Benzoin, sublimed, 99.5+%; Benzoin ethyl ether, 99%; Benzoin isobutyl ether, tech., 90%; Benzoin methyl ether, 96%; Benzophenone, 99%; Benzophenone/1-Hydroxycyclohexyl phenyl ketone, 50/50 blend; 3,3',4,4'-Benzophenonetetracarboxylic dianhydride, sublimed, 98%; 4-Benzoylbiphenyl, 99%; 2-Benzyl-2-(dimethylamino)-4'-morpholinobutyrophenone, 97%; 4,4'-Bis(diethylamino)benzophenone, 99+%; 4,4'-Bis(dimethylamino)benzophenone, 98%; Camphorquinone, 98%; 2-Chlorothioxanthen-9-one, 98%; (Cumene)cyclopentadienyliron(II) hexafluorophosphate, 98%; Dibenzosuberenone, 97%; 2,2-Diethoxyacetophenone, 95%; 4,4'-Dihydroxybenzophenone, 99%; 2,2-Dimethoxy-2-phenylacetophenone, 99%; 4-(Dimethylamino)benzophenone, 98%; 4,4'-Dimethylbenzil, 97%; 2,5-Dimethylbenzophenone, tech., 95%; 3,4-Dimethylbenzophenone, 99%; Diphenyl(2,4,6-trimethylbenzoyl)phosphine oxide/2-Hydroxy-2-methylpropiophenone, 50/50 blend;

4'-Ethoxyacetophenone, 98%; 2-Ethylanthraquinone, 97+%; Ferrocene, 98%; 3'-Hydroxyacetophenone, 99+%; 4'-Hydroxyacetophenone, 99%; 3-Hydroxybenzophenone, 99%; 4-Hydroxybenzophenone, 98%; 1-Hydroxycyclohexyl phenyl ketone, 99%; 2-Hydroxy-2-methylpropiophenone, 97%; 2-Methylbenzophenone, 98%; 3-Methylbenzophenone, 99%; Methybenzoylformate, 98%; 2-Methyl-4'-(methylthio)-2-morpholinopropiophenone, 98%; Phenanthrenequinone, 99+%; 4'-Phenoxyacetophenone, 98%; Thioxanthen-9-one, 98%; Triarylsulfonium hexafluoroantimonate salts, mixed, 50% in propylene carbonate; and Triarylsulfonium hexafluorophosphate salts, mixed, 50% in propylene carbonate.

Other suitable photoinitiators include the various IRGACURE products commercially available from BASF Corporation. The Key Products Selection Guide 2003 for Photoinitiators for UV Curing is hereby incorporated by reference in its entirety. A representative chemical class of photoinitiators is provided as examples. It would be appreciated that derivatives of such chemistries is also included. The representative list includes alpha_-Hydroxyketone and derivatives based on (1-Hydroxy-cyclohexyl-phenyl-ketone; 2-Hydroxy-2-methyl-1-phenyl-1-propanone; 2-Hydroxy-1-[4-(2-hydroxyethoxy) phenyl]-2-methyl-1-propanone). Phenylglyoxylate and derivatives based on (Methylbenzoylformate; oxy-phenyl-acetic acid 2-[2 oxo-2 oxy-phenyl-acetic acid 2-[2 oxo-2 phenyl-acetoxy-ethoxy]-ethyl ester and oxy-phenyl-acetic 2-[2-hydroxy-ethoxy]-ethyl ester). Benzyldimethyl-ketal and derivatives based on (Alpha, alpha-dimethoxy-alpha-phenylacetophenone). Alpha-Aminoketone and derivatives based on (2-Benzyl-2-(dimethylamino)-1-[4-(4-morpholinyl) phenyl]-1-butanone; 2-Methyl-1-[4-(methylthio)phenyl]-2-(4-morpholinyl)-1-propanone/IRGACURE 369 (30 wt %)+IRGACURE 651 (70 wt %). Mono Acyl Phosphine (MAPO) and derivatives based on (Diphenyl (2,4,6-trimethylbenzoyl)-phosphine oxide. MAPO alpah-Hydroxyketone and derivatives based on DAROCUR TPO (50 wt %)+DAROCUR 1173 (50 wt %). Bis Acyl Phosphine (BAPO) and derivatives based on Phosphine oxide, phenyl bis (2,4,6-trimethyl benzoyl). BAPO Dispersion based on (IRGACURE 819 (45% active) dispersed in water). BAPO/alpha_-Hydroxyketone (IRGACURE 819 (20 wt %)+DAROCUR 1173 (80 wt %). Metallocene (Bis(eta 5-2,4-cyclopentadien-1-yl), Bis [2,6-difluoro-3-(1H-pyrrol-1-yl), phenyl]titanium). Iodonium salt and derivatives based on Iodonium, (4-methylphenyl)[4-(2-methylpropyl)phenyl]-, hexafluorophosphate(1-).

The organic vehicle of the present invention can comprise a polymerizable composition or a crosslinkable composition. The term organic vehicle is used herein to indicate the portion of the curable adhesive composition that ultimately forms the resin upon curing, whether by polymerization or crosslinking. Thus, a polymerizable organic vehicle comprises at least one polymerizable monomer. A crosslinkable organic vehicle thus comprises a plurality of crosslinkable polymer chains. Ideally, the organic vehicle is of a suitable viscosity for dispensing/applying to the desired substrate.

The monomer system may be selected based upon overall requirements such as strength, flexibility or compliance, matching with substrate properties, and the type of bonding involved, such as electrically conductive bonding versus a strictly structural adhesive bond.

Some suitable monomer systems that may be used for various applications of the invention include, without limitation: epoxies, phenolics, urethanes, acrylics, cyanoacrylates, silicones, polysulfides, polyimides, polyphenylquinoxalines, and styrenes. A source for suitable monomer chemistries is "Engineered Materials Handbook: Adhesives and Sealants, Volume III (v. 3)" CRC Press, 1990, by Cyril A. Dostal, the contents of which are hereby incorporated by reference. In one particularly interesting embodiment of the present invention, the adhesive can be used to bond living tissue to living tissue, such as in adhesive suturing of wounds or surgical openings. Any monomer system resulting in a polymer that is biocompatible can be used in such applications, with preference given to the cyanoacrylates commonly already used in wound care, but with an X-ray initiated cure by down converting the X-ray into an energy sufficient to promote the curing of monomer based adhesive. The X-ray based curing described herein further includes adhesives based on crosslinking polymeric chains through activation of appropriate cross-linking agents.

Energy Converting Materials

The second essential component of the inventive material is a material capable of converting the imparted energy and converting it to photons in a spectral range that can be absorbed effectively by the photoinitiator. Preferably, the energy converting material is a downconverting material capable of absorbing higher-energy photons (typically from ionizing radiation such as X-rays) and down-converting to produce lower-energy photons (typically UV) in a spectral range that can be absorbed effectively by the photoinitiator. These materials are broadly classified in two classes: scintillators and phosphors. Many down-converter materials are known, including, without limitation: metal oxides; metal sulfides; doped metal oxides; or mixed metal chalcogenides. Also included in this category are organic-inorganic hybrid scintillators such as disclosed by Kishimoto et al. (Appl. Pys Lett. 2008, 93, 261901), the contents of which are incorporated herein by reference.

Many other downconverting particles, upconverting particles, plasmonics active particles and combinations of these are disclosed in U.S. provisional patent application 61/161,328, filed Mar. 18, 2009; U.S. provisional patent application 61/259,940, filed Nov. 10, 2009; U.S. Provisional Application Ser. No. 60/954,263, filed Aug. 6, 2007, and 61/030,437, filed Feb. 21, 2008; U.S. application Ser. No. 12/059,484, filed Mar. 31, 2008; U.S. application Ser. No. 11/935,655, filed Nov. 6, 2007; U.S. Provisional Application Ser. No. 61/042,561, filed Apr. 4, 2008; 61/035,559, filed Mar. 11, 2008; and 61/080,140, filed Jul. 11, 2008; U.S. patent application Ser. No. 12/401,478 filed Mar. 10, 2009; U.S. patent application Ser. No. 11/935,655, filed Nov. 6, 2007; U.S. patent application Ser. No. 12/059,484, filed Mar. 31, 2008; U.S. patent application Ser. No. 12/389,946, filed Feb. 20, 2009; and U.S. patent application Ser. No. 12/417,779, filed Apr. 3, 2009, the entire disclosures of each of which are hereby incorporated by reference.

Phosphor selection criteria were based on peak intensity of the emission, peak position with UV of the emission, the need to have a workable phosphor with minimal storage requirements, handling and packaging, the ability of the phosphor to couple to X-ray energy, the control over its particle size and particle size distribution; and, finally their surface chemistry.

Figure 6:
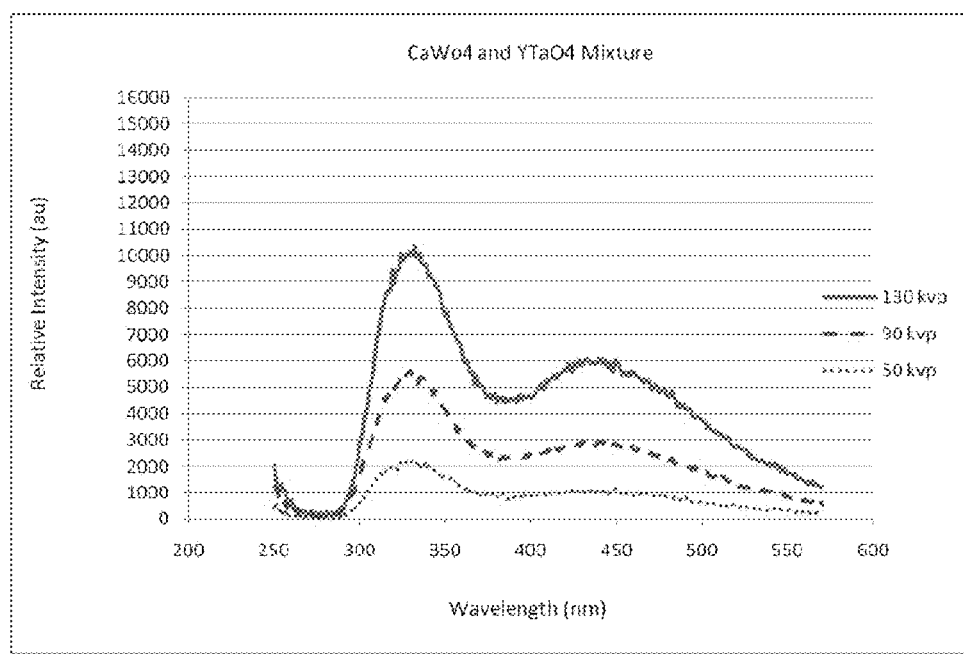
FIG. 6 provides emission spectra of a mixture of $CaWO_4$ and $YaTO_4$, upon irradiation with X-rays at intensities of 50, 90, and 130 kvp.

The peak emission target is between 310 nm and 400 nm or simply the UVA spectrum. It is desirable to have the maximum conversion of X-ray intensity into UVA intensity. This conversion described in various interrelated terms. Sometimes it is referred to as the quantum yield or probability of interaction between X-ray and phosphors. These interrelated terms include the coupling efficiency, emission effectiveness or the Effective-Z between the X-ray and the phosphor. A list of some of the best X-ray phosphors is reported in Table 1.

surements, it is clear that the higher X-ray intensity the higher the relative intensity of the emitted wavelength. (See FIG. 6)

TABLE 1

| # | Phosphor | Emission Spectrum Peak Emission (nm) | X-ray Absorption | | | Microstructure | | Hygro-scopic |
|---|---|---|---|---|---|---|---|---|
| | | | Emiss Eff (%) | Eff (Z) | K-edge (keV) | Specific Gravity | Crystal Structure | |
| 1 | BaFCl:Eu$^{2+}$ | 380 | 13 | 49.3 | 37.38 | 4.7 | Tetragonal | N |
| 2 | BaSO$_4$:Eu$^{2+}$ | 390 | 6 | 45.5 | 37.38 | 4.5 | Rhombic | N |
| 3 | LaOBr:Tm$^{3+}$ | 360, 460 | 14 | 49.3 | 38.92 | 6.3 | Tetragonal | N |
| 4 | YTaO$_4$ | 337 | | 59.8 | 67.42 | 7.5 | Monolithic | N |
| 5 | YTaO$_4$:Nb (*) | 410 | 11 | 59.8 | 67.42 | 7.5 | Monolithic | N |
| 6 | CaWO$_4$ | 420 | 5 | 61.8 | 69.48 | 6.1 | Tetragonal | N |
| 7 | LaOBr:Tb$^{3+}$ | 420 | 20 | 49.3 | 38.92 | 6.3 | Tetragonal | N |
| 8 | Y$_2$O$_2$S:Tb$^{3+}$ | 420 | 18 | 34.9 | 17.04 | 4.9 | Hexgonal | N |
| 9 | ZnS:Ag | 450 | 17 | 26.7 | 9.66 | 3.9 | Hexgonal | N |
| 10 | (Zn, Cd)S:Ag | 530 | 19 | 38.4 | 9.66/26.7 | 4.8 | Hexgonal | N |
| 11 | Gd$_2$O$_2$S:Tb$^{3+}$ | 545 | 13 | 59.5 | 50.22 | 7.3 | Hexgonal | N |
| 12 | La$_2$O$_2$S:Tb$^{3+}$ | 545 | 12.5 | 52.6 | 38.92 | 6.5 | Hexgonal | N |

UVA/UVB Emissions

In some applications the desirable incident or initiation energy is different than X-ray (such as EUV) while the desirable down-converted output intensity remains in the UVA. In other applications the desirable incident or initiation energy is X-ray but the desirable down-converted energy output of the phosphor is in the UVB. Yet in other cases the desirable incident or initiation energy is X-ray but the desirable down-converted energy output of the phosphor is in the UVA and the UVB. The selected phosphors were selected to work with excitation sources including X-ray, extreme UV and e-beam. Within the X-ray regime, the selected phosphors can couple to a flux of X-ray photons emanating from commercially available equipment sources used for therapeutic tumor treatments, medical imaging and semiconductor inspection.

An example of a material that emits in the UVA regime is provided in FIG. 1. The X-ray system used to carry out the experiment was the Faxitron X-ray System. An example of a material having an output in the UVB is provided in FIG. 2. An example of a material having an output in the UVA, UVB and the visible is provided in FIG. 3.

Mixed or Alloyed Phosphors

Figure 5:
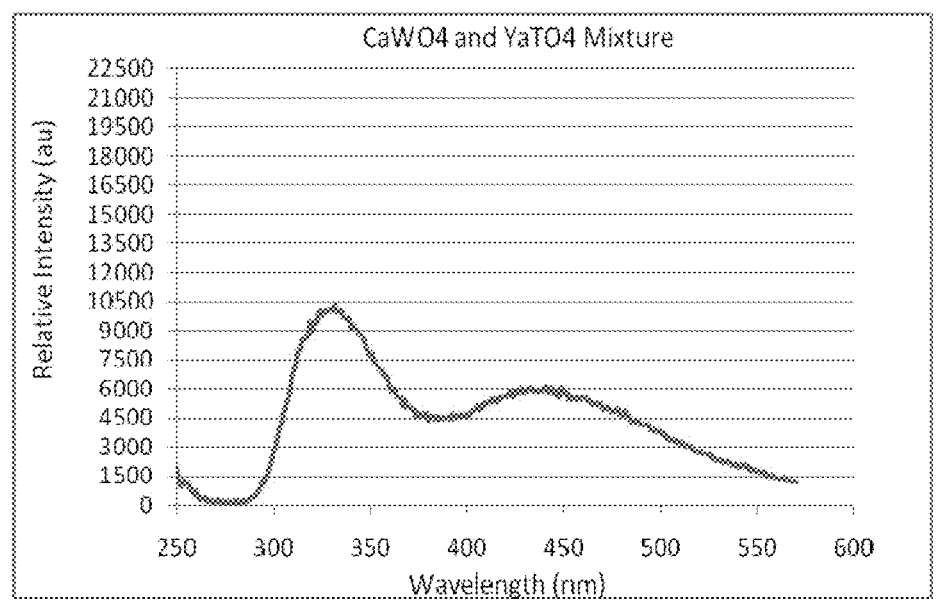
FIG. 5 provides an emission spectrum of a mixture of $CaWO_4$ and $YaTO_4$, upon irradiation with X-rays.

Another possibility of interest is the ability to mix at least 2 phosphors to broaden the output of the mixture compared with the starting phosphors. In this example 2 phosphors each emitting in a distinct region were mixed together and the output spectral output was measured to demonstrate the ability to influence the output intensity of the mixture compared to the starting materials. (See FIGS. 4 and 5)

The intensity of the initiation energy (X-ray in this case) influences the UV output of the phosphor. The following examples are provided to illustrate how modifying the intensity of photonic energy of X-ray can modulate the light output of the X-ray. The relative intensity output of a phosphor (CaOW$_4$) was measured as a function of the energy of the X-ray photons. The X-ray energy was modified by modifying the peak voltages that exist between the filament and the target. The target in this case was tungsten. The measurements were carried out using the same mass of phosphor under 50 kvp, 90 kvp and 130 kvp. The relative intensity of the emission in arbitrary units is indicative but not conclusive in terms of comparing different materials. However, within the same conditions used to conduct mea- The phosphors can be synthesized from different chemicals and using different processes to control their morphology, influence their properties and light intensity output but more importantly their stability in ambient air environments. It is preferred to have phosphors that are not hygroscopic. Phosphors are easier to handle and to work with when they are stable in water and do not contain dopants that are toxic; however, even when phosphors are not stable in water and do contain dopants that are toxic, the particles of the phosphors can be coated using chemistry synthesis methods that leads to the build-up of a protective coating which shields the phosphor from the environment (water for example) and shields the environment from the toxic dopant in the phosphor (bromide for example). The protective coating can be silica or can be diamond or diamond-like carbon. Silica can be formed using sol-gel derived techniques. Diamond and diamond-like carbon can be derived from chemical vapor deposition (CVD) based on hydrogen-methane gas mixtures. Handling and packaging of phosphors can be achieved through dispersion in solution or in powder form. It was found that silica coated phosphors make a good powder that does not agglomerate.

In addition to high intensity, emission at the correct wavelengths, another desirable attribute of phosphors is to have low specific gravity (if possible). A low specific gravity may help avoid sedimentation and settling when the phosphors are mixed into another media such as a resin or a resin blend containing photo-initiators.

Rheology Adjustment

The particle size of the phosphor is a relevant factor. The smaller the particle size the higher the surface area. The small particles were found to alter the rheology of resins containing photo-catalysts more effectively than larger phosphor particles. The larger the particles size the higher the intensity output. The phosphors were found to perform well in terms of conversion of X-ray into UVA and activating photo-catalysts inside resin systems when they contain a particle size distribution (not a mono-modal particle size distribution). The phosphors having small particles (i.e. having a high surface area) were successfully used to increase the viscosity of the resin without the use of active silica (or AEROSIL). In fact, a new method was developed in that enough phosphor nano-particles are added to adjust viscosity in-lieu of active silica. The best photo-activation and viscosity adjustment was found when nano-particles were used with a phosphor having particles up to the 5 microns particle size. In essence bimodal distribution of particles helps the packing factor (or loading content of phosphors into the resin) as well as helps in terms of rheological control and UVA light intensity generation for the formulation of adhesives having controllable viscosity, good curing under X-ray. A tri-modal or large distribution of particle sizes are effective in balancing rheology of the adhesive and cure response of the adhesive under X-ray.

Organic Materials

In addition to the inorganic compounds (or phosphors) described in the current invention, organic compounds can be used to achieve the same purpose described in the current invention. Anthracene and anthracene based compounds can be used to achieve the objective of the invention (curing with no line of sight and thermal energy). Anthracene exhibits a blue (400-500 nm peak) fluorescence under ultraviolet light. Furthermore, it was found that antharacene exhibits fluorescence under X-Ray energy. Anthracene light output was measured to be 40% to 50% of NaI(Tl).

Various plastic scintillators, plastic scintillator fibers and related materials are made of polyvinyltoluene or styrene and fluors. These and other formulations are commercially available, such as from Saint Gobain Crystals, as BC-414, BC-420, BC-422, or BCF-10.

| Phosphor | Product Reference | Peak Emission (nm) |
|---|---|---|
| Organic | BC-414 | 392 |
| Organic | BC-420 | 391 |
| Organic | BC-422 | 370 |

Other polymers are able to emit in the visible range and these include:

| Phosphor (Fiber Forms) | Product Reference | Peak Emission (nm) | # of Photons Per MeV |
|---|---|---|---|
| Organic | BCF-10 | 432 | 8000 |
| Organic | BC-420 | 435 | 8000 |
| Organic | BC-422 | 492 | 8000 |

Furthermore, the organic compounds that can convert X-ray to UV energy can be interwoven into synthetic polymer chains. These chains can be used as the base resin system for a cross-linking adhesive; hence leading to the formation of a new set of X-ray activatable resin systems.

A listing of downconverting phosphors in ascending peak emission wavelengths is provided in the Table 2. Interestingly, phosphors from this table can be selected to provide selective emissions at peak emission wavelengths from 310-550 nm, thus providing a wide array of potential materials for activation of a wide array of photoinitiators.

UV receptive chemistries can be made more reactive by adding photo-sensitizers. This process is referred to as photo-sensitization. Certain photosensitive chemical compounds can be added to supplement photonic energy to the reactant and the reactant site to promote or enhance curing.

For UV curing applications, it is of interest to have chemistries that upon exposure to the UV radiation would form an intermediate in an excited state that in turn emits light of the correct wavelength for further curing to take place. In other words, a sensitizer plays a role in energy transfer.

Many light sensitizing chemistries are known and widely used in the industry and these include to name but a few, acenaphthene quinone, aceanthrene quinone, or a mixture thereof with anthrone and/or naphthaquinone, violanthrone, isoviolanthrone, fluoresceine, rubrene, 9,10-diphenylanthracene, tetracene, 13,13'-dibenzantronile, levulinic acid.

TABLE 2

| Phosphor Color | Emission Spectrum Peak Emission (nm) | Emiss Eff (%) | Eff (z) | X-Ray Absorption K-edge (keV) | Specific Gravity | Crystal Structure | Hygroscopic |
|---|---|---|---|---|---|---|---|
| Zn3(PO4)2:Tl+ | 310 | | | | | | N |
| BaF2 | 310 | | | | | | Slightly |
| CsI | 315 | | | | | | N |
| Ca3(PO4)2:Tl+ | 330 | | | | | | N |
| YTaO4 | 337 | 59.8 | | 67.42 | 7.5 | Monolithic | N |
| CsI:Na | 338 | | | | | | Y |
| BaSi2O5:Pb2+ | 350 | | | | | | N |
| Borosilicate | 350 | | | | | | N |
| LaCl3(Ce) | 350 | | | | | | Y |
| SrB4O7F:Eu2+ | 360 | | | | | | N |
| RbBr:Tl+ | 360 | | | | | | ? |
| (Ba, Sr, Mg,)3Si2O7:Pb2+ | 370 | | | | | | N |
| YAlO3:Ce3+ | 370 | | | | | | N |
| BC-422 | 370 | | | | | Organic | ? |
| BaFCl:Eu2+ | 380 | 13 | 49.3 | 37.38 | 4.7 | Tetragonal | N |
| BaSO4–:Eu2+ | 390 | 6 | 45.5 | 37.38 | 4.5 | Rhombic | N |
| BaFBr:Eu2+ | 390 | | | | | | ? |
| BC-420 | 391 | | | | | Organic | ? |
| BC-414 | 392 | | | | | Organic | ? |
| SrMgP2O7:Eu2+ | 394 | | | | | | N |
| BaBr2:Eu2+ | 400 | | | | | | N |
| (Sr, Ba)Al2Si2O8:Eu2+ | 400 | | | | | | N |
| YTaO4:Nb(*) | 410 | 11 | 59.8 | 67.42 | 7.5 | Monolithic | N |
| Y2SiO5:Ce3+ | 410 | | | | | | N |

TABLE 2-continued

| Phosphor | Emission Spectrum Peak Emission (nm) | Emiss Eff (%) | Eff (z) | X-Ray Absorption K-edge (keV) | Specific Gravity | Crystal Structure | Hygroscopic |
|---|---|---|---|---|---|---|---|
| CaWO4 | 420 | 5 | 61.8 | 69.48 | 6.1 | Tetragonal | N |
| LaOBr:Tb3+ | 420 | 20 | 49.3 | 38.92 | 6.3 | Tetragonal | N |
| Y2O2S:Tb3+ | 420 | 18 | 34.9 | 17.04 | 4.9 | Hexgonal | N |
| Lu2SiO5:Ce3+ | 420 | | | | | | N |
| Lu1.8 Y0.2SiO5:Ce | 420 | | | | | | N |
| ZnS:Ag | 450 | 17 | 26.7 | 9.66 | 3.9 | Hexgonal | N |
| CdWO4 | 475 | | | | | | Slightly |
| Bi4Ge3O12 (BGO) | 480 | | | | | | N |
| (Zn, Cd)S:Ag | 530 | 19 | 38.4 | 9.66/26.7 | 4.8 | Hexgonal | N |
| Gd2O2S:Tb3+ | 545 | 13 | 59.5 | 50.22 | 7.3 | Hexgonal | N |
| La2O2S:Tb3+ | 545 | 12.5 | 52.6 | 38.92 | 6.5 | Hexgonal | N |
| Y3Al5O12 (Ce) | 550 | | | | | | N |
| LaOBr:Tm3+ | 360, 460 | 14 | 49.3 | 38.92 | 6.3 | Tetragonal | N |
| CaF2(Eu) | 435/300 | | | | | | N |

Spectral Matching

It will be appreciated that the most efficient system will be one in which the particular photo-initiator is selected based on its absorption, its photo-catalysis sensitivity to the intensity of the incident radiation (i.e.; the efficiency of energy transfer).

The emission wavelength in many embodiments of the present invention depends on the particular downconverter material chosen to carry out the cure of the photo-catalytic reaction under consideration. Accordingly, to ensure the most efficient energy transfer from the phosphor to the photoinitiator, the phosphors are paired with the correct photoinitiators to match the emitted frequency/wavelength from the down-converter material to the peak absorption of the photo-initiator. This is referred to as a spectral match in the current invention. The spectral matching mentioned above increases the chances of successful attempts needed to overcome the activation energy barrier gating reactions. Table 3 shows the relative peak absorption of certain photo-initiators and the relative peak emissions of certain phosphors. The pairing of photo-initiators and phosphors was done accordingly to the table and successfully demonstrated as illustrated in the examples.

TABLE 3

| Photoinitiator | Absorption Peaks | Peak Absorption |
|---|---|---|
| IRGACUR 784 | 398, 470 | 398 |
| DAROCUR 4265 | 240, 272, 380 | 380 |
| IRGACUR 2100 | 275, 370 | 370 |
| IRGACUR 2022 | 246, 282, 370 | 370 |
| IRGACUR 819DW | 295, 370 | 370 |
| IRGACUR 819 | 295, 370 | 370 |
| DAROCUR TPO | 295, 368, 380, 393 | 368 |
| IRGACURE 651 | 250, 340 | 340 |
| IRGACURE 184 | 246, 280, 333 | 333 |
| IRGACURE 500 | 250, 332 | 332 |
| DAROCUR 1173 | 245, 280, 331 | 331 |
| IRGACURE 754 | 255, 325 | 325 |
| DAROCUR MBF | 255, 325 | 325 |
| IRGACURE 369 | 233, 324 | 324 |
| IRGACURE 1300 | 251, 323 | 323 |
| IRGACURE 907 | 230, 304 | 304 |
| IRGACURE 2959 | 276 | 270 |
| Phosphor | | Peak Emission |
| LaOBr:Tm3+ (coated) | | 360, 460 |
| CWO4:Pb | | 425 |
| YTaO4:Nb (*) | | 410 |

TABLE 3-continued

| Y2SiO5:Ce | 410 |
|---|---|
| BaSO4–:Eu2+ (coated) | 390 |
| SrB6O10:Pb | 360 |
| BaSi2O5:Pb2+ | 350 |
| CsI:Na (Coated) | 338 |
| YTaO4 | 337 |

Optimization Of Distance

Furthermore, the distance between a phosphor particle and a photo-initiator influences the efficiency of energy transfer. The shorter the distance between the photo-initiators and the phosphors the better chances of energy transfer leading to successful reactions will take place. Inside a mixture of a curable system there are many particles and a relatively elevated concentration of photo-initiators. As a result, there is more than one distance between particles and photo-initiators. In these cases we refer to the average distance between phosphor particles and photo-initiators.

The photo-initiators can be adhered onto the surface of phosphor particles using tethering of adsorption techniques among others. In the case of tethering, a high vs. low molecular weight would be an effective way to change the distance between the photo-initiators and the particles respective surfaces. In the case of deposition through adsorption, the distance between the surface of the phosphors and the photo-initiators can be altered by innerlayering a coating that is transparent to the radiation emitted by the phosphors. $SiO_2$ is an example of such inner layer since it is transparent to UV.

Packing factor and average distance between the phosphors and the photo-initiators can be impacted using a surface coating. The packing factor of a phosphor having innate surface chemistry would therefore be different than that for a phosphor having a relatively thick coating.

The combination of the spectral match defined above, the average distance between the photo-initiators and the phosphors, the intensity of radiation generated by the phosphor particles under an initiation radiation, the particle size distribution constitutes the most efficient embodiment of the present invention.

In regards to the packing factor of the phosphors, a large enough silica coating deposited on the surfaces of particles would change the effective packing factor of effective density of the powder (i.e.; mass per unit volume of powder). Similarly, a phosphor coated with a coating having an irregular shape can further influence the mass per unit volume. As an example a powder of an average particle size of 5 microns can be coated with a enough silica to obtain an average size of 15 microns.

Figure 7:
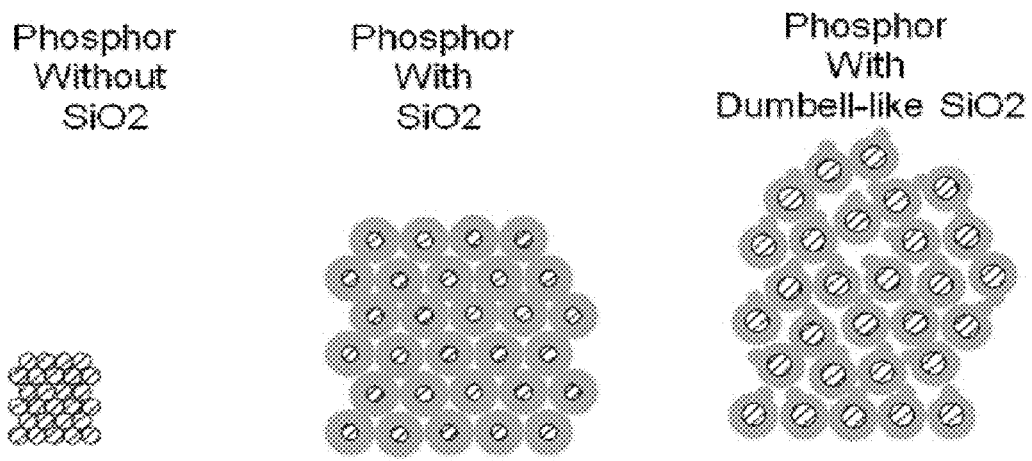
FIG. 7 provides a representation of the effects of a large coating thickness or coating shape on packing factor of a phosphor.

The phosphor itself becomes more or less responsive to the incident X-ray beam as a result of the coating that can alter its effective density of the mass of the powder per unit volume. The probability of interaction between the X-ray energy and the phosphors decreases with increasing coating wall thickness. An illustration is provided in FIG. 7 where the same amount of phosphor (i.e.; the X-ray coupling agent) can occupy a larger thickness.

Figure 8:
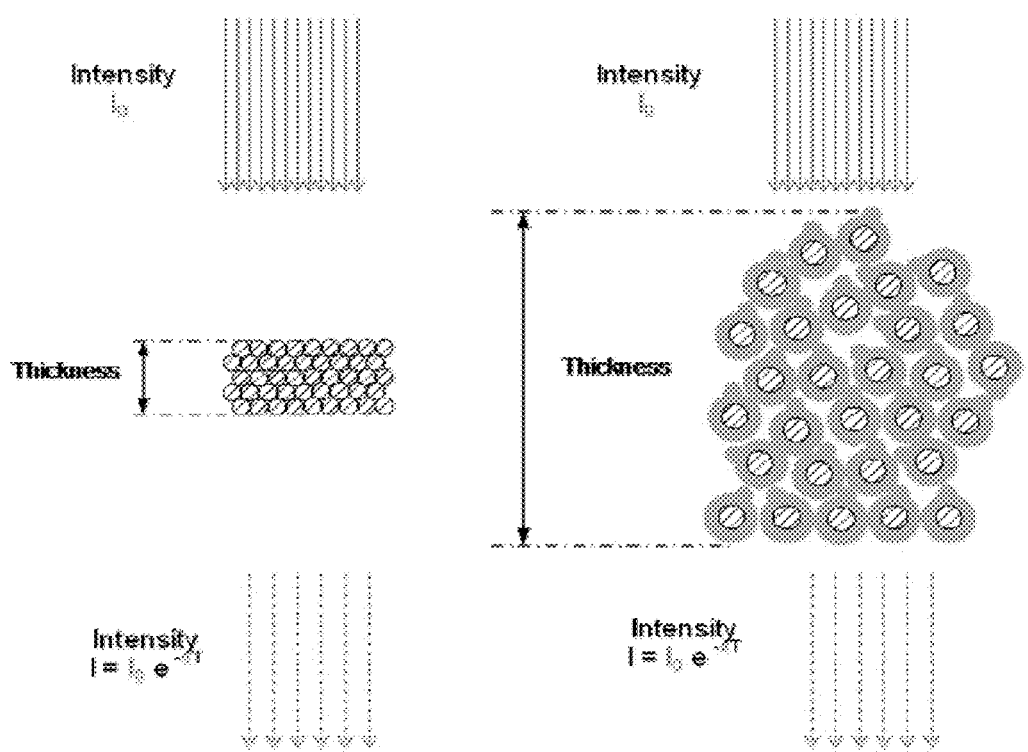
FIG. 8 provides the changes in attenuation of intensity of X-ray between a phosphor that has a coating and an innate phosphor surface.

By virtue of changing the concentration of phosphor or by changing the effective packing factor of the phosphor we can influence the probability of interaction of the X-ray energy with the phosphor filled resin. The intensity of X-ray can be attenuated differently between a phosphor that has a coating and an innate phosphor surface (see FIG. 8).

The coated phosphors can be used as the filler in the resin system. The widely used filler in the industry is silica. In some cases alumina and boron-nitride are used. The silicate fillers are used to substitute some of the resin volume without degrading the properties of curable material. The filling of silica powder leads to cost savings. Filled systems are typically more mechanically stable and more cost effective than the unfilled systems.

Cure Categorization:

The UV curing materials can be diverse; but, as a general categorization, the following materials sets are outlined by specific resin families, associated initiators, cure mechanism and appropriate application. This is by no means an inclusive list but just a general categorization to further illustration. The current invention is compatible with each of these categories including radical cross-linking or polymerization, cationic crosslinking, base catalyzed crosslinking.

Radical Crosslinking:

Radical cross-linking or polymerization utilizes resin systems such as acrylates, maleates, styrenes. The initiators used in these cases include aromatic ketones such as phenyl-glyoxylates, phenyl-glyoxylates, alpha-amino ketones, benzildimethyl ketal, bisacylphosphine oxides, monoacylphosphine oxides, benzophenones.

The photoiniators for free-radical polymerization can generate reactive chemical intermediates such as those that occur in homolytic bond cleavage, hydrogen abstraction, photo-charge transfer. The addition of phosphors is compatible with the photo-reactive species and does not interfere with the basis of free radical polymerization including the 2-photons based processes.

By way of illustration, a two-photon photoleachable photoinitiator such as bisacylphosphine oxides may absorb a first photon of a given wavelength range (for example below 430 nm) to split into another photo-initiator type such as monoacylphosphine oxides that in turn can be activated using another photon of another wavelength range (below 415 nm) and lead to further radical species able to promote the formation of high molecular weight polymers.

The application of free radical cure encompasses a broad set of applications including coatings, electronic materials, and adhesives. The novel method described in the present invention extends the use of such free-radical cure into no line of site applications that cannot be accomplished otherwise and renders the use of deeply penetrating initiating radiation the source of energy that indirectly triggers the cure.

Cationic Crosslinking

Cationic crosslinking utilizes resin systems such as epoxides, vinyl ethers, oxetanes. The initiators used in these cases include diaryl iodonium salts, triaryl sulfonium salts and onium salts to name a few. The applications of such cationic crosslinking are found in electronic materials, inks and adhesives. The addition to these special salts triggers curing by proton generation which leads to cationic polymerization. The phosphors described in the current invention are applicable to cationic curing materials and their applications.

As an example of a curing with a photochemical initiators, a compound such as bisazide 4,4'-diazidodibenzalacetone-2,2'-disulfonic acid disodium salt can be added to a mix. This compound initiates the crosslinking upon irradiation at a wavelength of 360-370 nm which is a readily available wavelength. Another example include benzophenone can be used as a photo initiator in UV-curing applications such as inks.

Base Catalyzed Crosslinking

Base catalyzed crosslinking utilizes resin systems such as epoxy, polyol/isocyanate, and Michael addition. The mechanism of curing is based on Lewis base generators. Applications of the base catalyzed crosslinking extend to coatings and adhesives.

Direct X-Ray Cure:

Direct curing with x-ray energy (with or without the use of phosphors) is also possible in the present invention. For example, one can add a chemical compound that has the capability of being activated directly under x-ray energy, such as methyl ethyl ketone peroxide (MEKP), which is an organic peroxide, to assist in initiating the polymerization. Also, benzoyl peroxide, another compound in the in the peroxide family that has two benzoyl groups bridged by a peroxide link, can be used to assist in the initiation of the polymerization under x-ray. The effect of phosphors and these peroxide based chemicals can be additive.

Co-Curing

Figure 9:
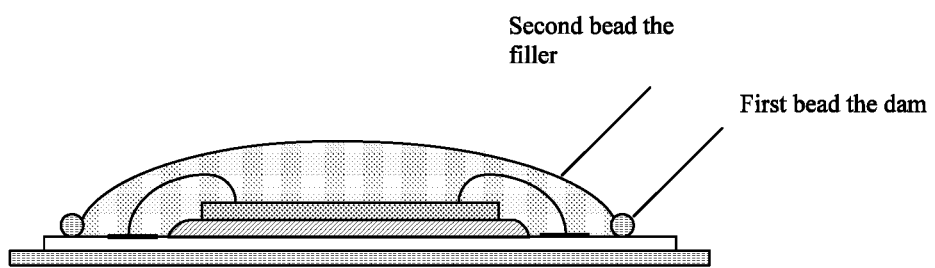
FIG. 9 provides a representation of an embodiment of a dam-and-fill application of the present invention.

In some applications it is useful to have 2 adhesive beads. One adhesive bead is filled with a phosphor having a high effective packing density and another adhesive bead having a lower packing density. In this case, under the same X-ray energy intensity, one bead would cure faster than the other. In some dam and fill applications, such as in RF-ID, one could apply a dam, cure it, and then fill and cure the fill. (See FIG. 9) However, one could co-cure the 2 adhesive beads using the method described in the current invention by the ability to couple more initiation energy into the containment bead as compared with the filler. These methods allow the curing of the containment bead and the filler material at the same time (co-curing) or curing one after the other (sequential curing). The same base adhesive can be used for both cases (possibly the same chemical formulation) with the containment bead having a phosphor of a different conversion efficiency than that of the filler material. This can be readily done by proper choice of the phosphor, or content of the phosphor. In a way the adhesive beads can be cured effectively at the same time but one sees more UV intensity than the other and cure faster than the other under the same X-ray beam.

Figure 10:
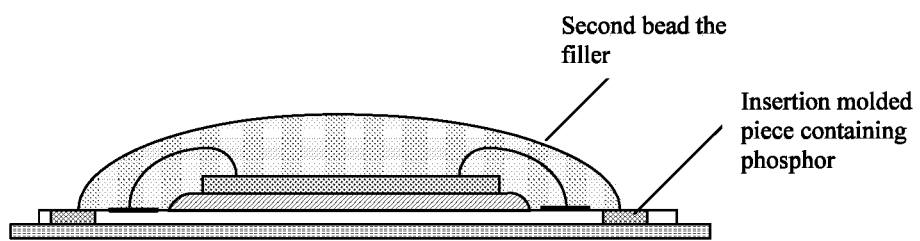
FIG. 10 provides a representation of an embodiment of the present invention using an insertion molded piece placed in the substrate to intensify the UV output.

Yet in another embodiment of the present invention, an insertion molded piece of plastic containing the appropriate amount of phosphor is added as part of the material to be cured. (See FIG. 10) As a molded frame this acts as the source of UV under X-ray energy. In this case the inserted molded piece gives extra UV energy to the dam (or perimeter area) and leads to faster curing. This allows the materials to cure more selectively at the borders. This example describes the usefulness of insertion molding as described in FIG. 10.

Additionally photo-sensitizing chemistries can be used to enhance the photo-catalytic based reactions.

Sol Gel Coating Surface Modification for Special Phosphors.

Synthesizing phosphors in the micron and nanometer particle sizes can be done using various methods. Also various phosphors may have different surface chemistries. Some phosphors could be potentially hygroscopic or toxic in high doses. One way to enable the use of hygroscopic or potentially toxic phosphors is to form a containing barrier layer around phosphor particles. This has the double benefit of standardizing different phosphor chemistries to have the same common surface chemistry with predictable behavior as well as shield the phosphor inside a barrier layer. A sol-gel derived silicate coating is one method by which this can be achieved. Silica happens to be UV transparent and is congruent with most oxides and most phosphors that are not hygroscopic (as listed in the phosphor table).

The protective coating can be silica or can be diamond or diamond-like carbon. Silica can be formed using sol-gel derived techniques. Diamond and diamond-like carbon can be derived from CVD based on hydrogen-methane gas mixtures. These are but representative examples of the methods that are possible.

Dispersion:

The uniformity of dispersion of phosphors inside a resin is quite important. A uniform distribution of phosphors inside a curable system influences the homogeneity of the curable material and therefore the mechanical and optical properties of the curable material. The mixing uniformity and the particles size distribution have an influence on the curing system response in terms of cure extent as a function of time under the initiation energy. The uniformity of the dispersion can be short lived if the phosphors have a high specific density leading to settling in the resin. For this reason some surface modification techniques can be desirable to maintain the phosphors in suspension.

Dispersants

The surface of the phosphors can be modified for 2 general purposes. One method leads to tethering or adsorbing the photo-initiators onto the surface of the phosphors. The other method is to add dispersant chemistries to the surface of phosphors to enable the phosphors to remain in suspension after the adhesive is formulated and the ingredients have been mixed together. In general phosphors are preferred to be in powder form with minimal aggregation between particles. The dispersion of phosphor powder in a resin system can be achieved using various methods. These dispersion methods keep the phosphors in suspension by limiting or preventing the potential re-flocculation caused by the particles' Brownian motion at room temperature or at temperatures above room temperatures by 20° C. to 30° C. These slightly elevated above room temperature are useful in dispensing the adhesives through a needle using a piston or an auger pump.

The surface modification of the phosphors to maintain a uniform dispersion after mixing is important. Various organic polymer agents can be used to increase the wetting characteristics of the phosphors into the resin chemistry. Similarly, various dispersing agents can be added to maintain the phosphor particles in suspension inside the mix. The dispersing agents are built from polyurethane or polyacrylate polymeric structures having high molecular weight (3000-50000). Various dispersing agent are available in the market. The dispersants can be anchored onto inorganic surface by virtue of surface charge (the electrostatic attraction of oppositely charged surfaces) and can be anchored or adsorbed to the organic substances like the chains in the resin by virtue of dipolar interactions, hydrogen bonding and London/van-der-Waals forces. Once anchored in place the high molecular weight dispersants increase the steric hindrance for particles to diffuse too close to one another hence preventing agglomeration of phosphors.

Tethering

The downconverting particles and photo-initiators used in the present invention can be added as separate components to the curable adhesive formulation, or can be tethered to one another to provide increased likelihood of activation of the photoinitiator upon emission from the downconverting particles. Tethering of photoinitiators to the downconverting particles can be done by any conventional chemistry, so long as it does not interfere with the emission characterstics of the downconverting particles (other than potential slight movement of the peak emission in the red or blue direction), and so long as it does not interfere with the ability of the photoinitiator to initiate polymerization of the curable adhesive composition. One may also use combinations of two or more phosphors, two or more photoinitiators, or both, to achieve more complex curing kinetics. Further, one can use organic downconverters, such as anthracene, rather than the various inorganic downconverters noted above. With the organic downconverters, there are additional possibilities including, but not limited to, use of the organic downconverter material as a separate component in the curable adhesive composition, tethering the organic downconverter to the photoinitiator, as described for the inorganic downconverter particles above, or even incorporation of the organic downconverter groups into one or more of the monomer components of the curable adhesive composition.

Figure 61:
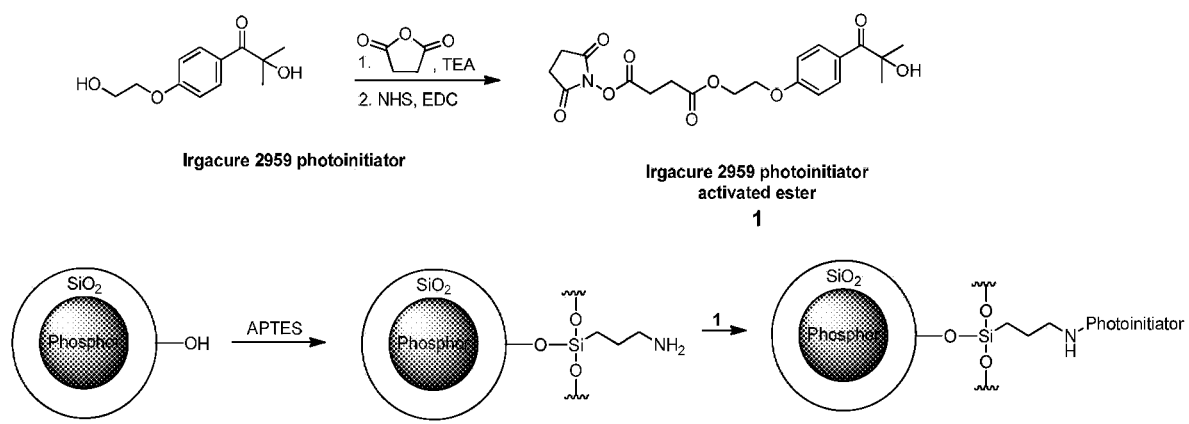
FIG. 61 depicts one suitable chemistry for tethering inorganic downconverter particles to the photoinitiator whereby a silica coated phosphor is reacted with aminopropyltriethoxysilane (APTES), then the modified photoinitiator is bound to the pendant aminopropyl group.

One suitable chemistry for tethering inorganic downconverter particles to the photoinitiator is shown in FIG. 61, whereby a silica coated phosphor is reacted with aminopropyltriethoxysilane (APTES), then the modified photoinitiator is bound to the pendant aminopropyl group.

Other possible modifications include, but are not limited to, the following:

a. Modification of existing Adhesives by adding special downconverting particles from X-ray to UV in the range of susceptibility of a Photoinitiator Rheology & Cost of Phosphors Because the surface area (and hence the overall surface energy) of the nano-sized particles is very high, the viscosity rises quickly with the addition of a small amount of nano size powders. This limits the amount of filler that can be added. On one hand this limits the UV intensity that can be emitted by the phosphors under X-ray energy. On the other hand the limited filler loading that can be achieved is not economically favorable since fillers are typically less expensive than the base resins and catalysts. Furthermore, the viscosity increase with the addition of nano-size particles becomes excessive which limits the use of the adhesive to certain application categories but not others. In most adhesive application it is favorable to use micron size particles when possible. Though as stated earlier, the best mode calls for a bi-modal particle size distribution consisting of mixture of nano and micron size particles.

In general $SiO_2$ is more cost effective compared to phosphors. This is not always the case. One method by which enough UV light output is achieved while safeguarding a favorable economic phosphors-utilization is to build a composite particle based on $SiO_2$ as the core particle and decorated with the appropriate phosphors in terms of type and concentration necessary to achieve the targeted photo-catalytic reactions (i.e.; the right wavelength output and luminosity or intensity output).

Building Composited Particles

In applications that require the use of micron level particles that are cost effective down converters, the surface of a carrier particle made of silica can be decorated with desirable phosphors with nanometer particle size. The phosphors are chosen for the right emission UV wavelength and intensity under X-ray.

The downconverting particle comprises a composite of nanoparticles and a silicate carrier particle. The silicate carrier particle has the same surface characteristics as a particle typically used as a filler (including silica). In this case the down converting particles are bonded to the surface of the base carrier particle followed by a coating as shown in FIGS. 11A and 11B.

By way of illustration the construction of such a composite particle is hereby provided. This description is non-inclusive of all the possibilities but provides one viable synthesis method.

The core or carrier particle can be made of glass, such as $SiO_2$ or alkali-lead-silicate and have a diameter of about 2 microns. Nanometer-scale downconverting particles are applied to the surface of the core particle, and subsequently made to adhere or bond to the surface of the core particle (see FIG. 11B). Some of the methods enabling this bonding process include precipitation techniques from a solution. Another method is based on condensation by heating the downconverting particles to much elevated temperatures compared to the core particles while maintaining the silicate based particles above their softening point. At the correct respective ranges of temperature, which are readily determined by one of ordinary skill in the art based on the compositions of the core particle and downconverting particle chosen, the downconverting particles and the carrier particles are forced into contact, leading to condensation, thus allowing surface deposition to take place. The downconverting particles can be any of the phosphors listed in the table.

Quantum Dots and Alloyed Derivatives—

Figure 12:
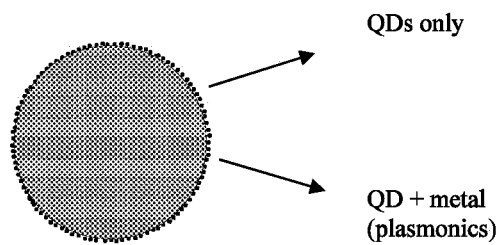
FIG. 12 provides a representation of a silica carrier particle coated with quantum dots or alloyed quantum dots or metal alloys exhibiting plasmonic behavior under X-ray.

The downconverting particles, for example, can be quantum dots with the suitable range of downconversion from X-ray to UV. The quantum dots and/or oxides used for the downconversion process can further comprise elements, or alloys of compounds or elements tuned for plasmonic activity (see FIG. 12). In a preferred embodiment, the quantum dots preferably comprise a mixture of zinc sulfide and zinc selenide, more preferably in a ratio within a compositional window of 60% zinc sulfide, 40% zinc selenide to 70% zinc sulfide, 30% zinc selenide. The metal alloys used for plasmonics comprise silver/gold mixtures, more preferably within the compositional window of 60% silver and 40% gold, to 70% silver and 30% gold.

Figure 13:
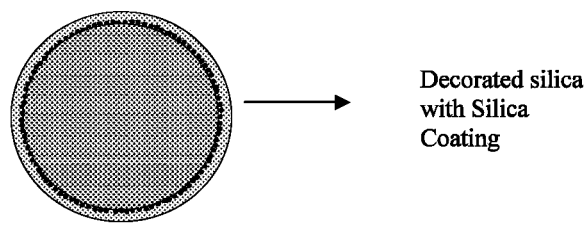
FIG. 13 provides a representation of a silica carrier particle decorated with nano-sized downconverters and then coated with silica.

After the carrier core particle is decorated with the down converting particles, coating the outer layer is desirable to encapsulate and protect the down converting particles as well as modify the surface. The outer layer coating can be accomplished using sol-gel processing followed by heat treatment. This leads to the formation of a composited particle consisting of a core particle with down-converting particles on the surface and the whole is coated with a silicate coating. (see FIG. 13). This special filler particle is used to replace an existing filler material.

Tethering to Composite Particles

Figure 14:
FIG. 14 provides a representation of a photoinitiator tethered or adsorbed on the surface of a nano-sized phosphor particle.

The present invention includes special provisions for a modified use of existing photoinitiators by tethering the photoinitiator to nanoparticles having downconverting properties. This close proximity of nanoparticle to photoinitiator maximizes the chance for photoinitiation or photo-catalysis, and can achieve improved cure efficiencies. (see FIG. 14)

Figure 15A:
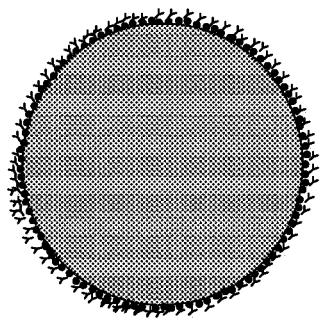
FIGS. 15A and 15B provide representations of a silica micro particle decorated with nano-size phosphor particles having photoinitiators tethered or adsorbed on the surfaces thereof and photoinitiators tethered directly on a silica coating around a particle that is decorated with nano-sized phosphors, respectively.
Figure 15B:
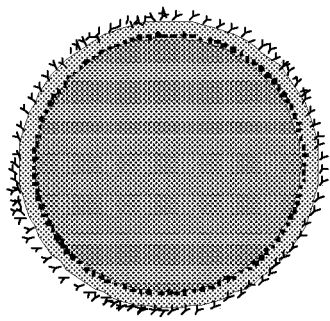

In the tethered case, the downconverting particles are added during mixing an adhesive preparation using tethered particles on a carrier particle and mixing into the adhesive. As an alternative embodiment, the tethered photoinitiator and downconverting particles can be positioned on the surfaces of micron level carrier particles. (See FIGS. 15A and 15B) The carrier particles are then used as filler. This time no surface coating is necessary and the photoinitiator is in direct contact with the resin. (FIG. 15A). Alternatively, this arrangement can also use a coating of $SiO_2$, on which are tethered the photoinitiators. (FIG. 15B).

Since in this particular embodiment, micron size particles (large particles) are added to the mix, the impact on adhesive rheology is minimized compared to adding nano-size particles. This method can thus present added advantages, including the ability to use the micron size particles as a filler to otherwise alter the cured adhesive or polymer properties.

Brighter Composite Particles

Figure 16A:
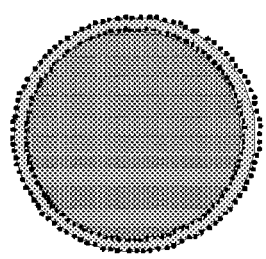
FIGS. 16A and 16B provide representations of a double layered decoration that is non-tethered with photoinitiators and a double layered decoration with tethered photoinitiators, respectively.
Figure 16B:
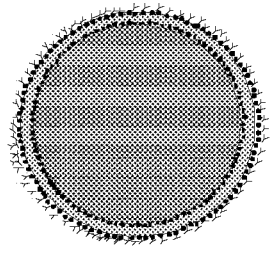

Achieving brighter particles can be done by having the carrier particle decorated with 2 layers of phosphors. First the carrier particle is decorated with nano-sized phosphors (FIG. 16A), then coated using sol gel derived silica and lastly decorated a second time with phosphors of the correct size (FIG. 16B). This technique can be repeated to obtain more phosphors or down conversion particles at the outer-layers of the carrier particles.

Surface Preparation:

Adhesion develops through various factors including mechanical interlocking, adsorption, electrostatic, diffusion, weak boundary layer, acid base, chemical (covalent bonding), etc. In general, the greater the surface irregularities and porosity at a joint area, the greater the joint strength. The greater the compatibility of the size of the adhesives and the interstices in the adherend, the greater the bond strength can be. Roughness of the surfaces can increase or decrease the joint strength.

The factors affecting joint strength include: surface energetics (wetting), intrinsic stresses and stress concentrations, mechanical response of various bulk phases and inter-phases involved, geometrical considerations, mode of applying external stresses, mode of fracture or separation, visco-elastic behavior.

The wetting and the setting of the adhesive bead is important for a good bond formation. The spreading co-efficient of an adhesive depends on the various surfaces and associated surface tensions involved. The surface tensions are referred to here as the energetic requirements. The substrate (solid), the adhesive (liquid) and the vapor (open air in most cases) all play a role. Wetting of the surface depends on the surface energy between the solid and the liquid, the liquid to vapor surface tension and between solid to vapor surface tension. Substrates such as Teflon, PET, Nylon, PE, and PS have low energy. Substrates such as metals, metal oxides, and ceramics have high energy.

The adhesive chemistry (the liquid in this example) can be tailored to adjust the energetic requirements at the various surfaces. But that is not sufficient. For example, most RTV silicone resins fulfill the energetic requirements but give negligible adhesion unless primers are used. Adhesive joints can be made stronger by surface treatments of the surfaces to be joined. Also inter-phases can be made between the adherend and the adhesive.

For the above considerations (surface energetic requirements and primers treatments) many surface modification techniques are used to achieve the goal of strong and durable adhesion at joints. The treatment of polymer surfaces is used for various reasons including one or more of the following list extending to making the polymers more adhesionable, increase their printability, make them more wettable, provide an enclosing layer, improve tribological behavior, potentially prepare them for metal plating, improve their flame resistance, provide antistatic properties, control permeation.

Dry surface modification includes, but is not limited to, a surface plasma ionized through RF or microwave, flame, UV, UV sensitized, ozone, UV/ozone, X-ray, LASER, electron beam, ion bombardment, and friction against other materials.

Wet surface modification encompasses chemical reactions such as oxidation, sulfonation, ozonation, phosphatization, chromate conversion, amination, grafting, selective etching, deposition of coupling layers (silanes), surfactant adsorption, photochemical compounds, solvent (surface swelling), prevention of diffusion of low molecular weight materials to the surface, and others.

Method of Use

Figure 62:
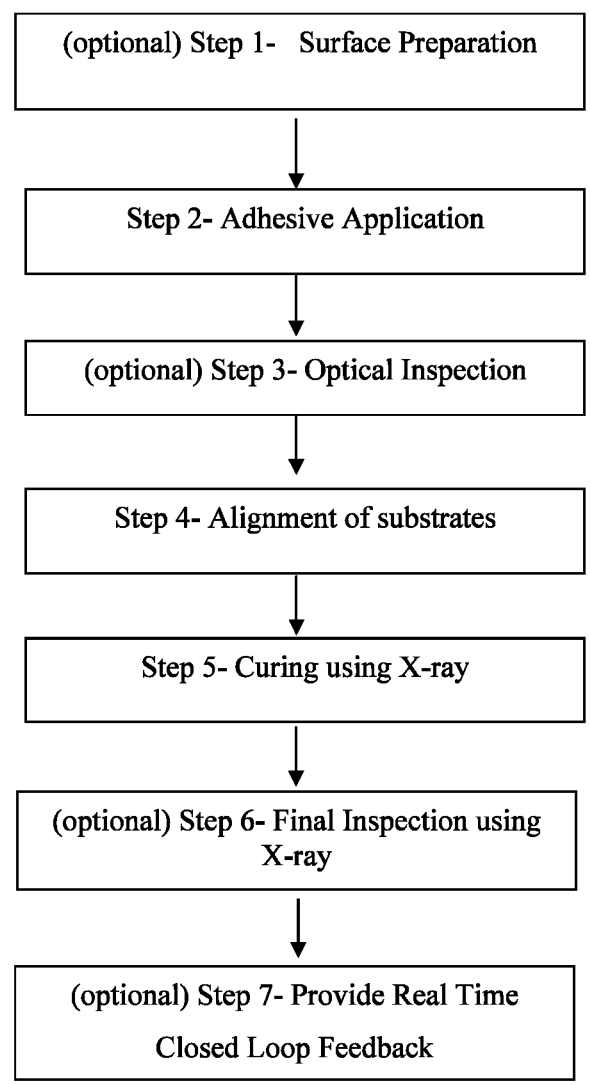
FIG. 62 provides a block flow diagram of one embodiment of a typical method of use in the present invention.

One embodiment of a typical method of use in the present invention can be summarized in FIG. 62.

APPLICATIONS AND EXAMPLES

List of Numbered Items in Figures

10: Anisotropic Conductive Polymer Sphere
10': Anisotropic Conductive Polymer Sphere—Partially Flattened
11: Anisotropic Conductive, UV or Visible Light Emitting, Polymer Sphere
11': Anisotropic Conductive, UV or Visible Light Emitting, Polymer Sphere—Partially Flattened
20: Polymer Core
20': Polymer Core—Partially Flattened
22: Nickel Plating
22': Nickel Plating—Partially Flattened
24: Gold Plating
24': Gold Plating—Partially Flattened
26: Down-Converting Photon Emitter Coating
26': Fractured Down-Converting Photon Emitter Coating
28: Flip Chip Device
30: Substrate
32: Flip Chip Device Bumps
32': Substrate Solder Bumps
34: Matrix Epoxy Resin
35: X-ray activated, UV or Visible Light curable, Anisotropic Conductive Adhesive (ACA) epoxy
36: Polymer Coating
36': Fractured Polymer Coating
38: Down-Converting Photon Emitters
39: Wafer Aligner and Bonder
40: Top Integrated Circuit (IC) Wafer
41: Bottom Integrated Circuit (IC) Wafer
42: Thru Silicon Via (TSV) Contacts
44: Vacuum Plate
46: Split field prism and lens device
47: Fixed lens-pair
48: Applied Force
49: Top wafer alignment fiducial
49': Bottom wafer alignment fiducial
50: X-ray Exposure Device
51: Superimposed alignment fiducials
52: X-ray Imaging Detector
60 Adhesive material
60-1 Liquid Encapsulant (Underfill)
60-2 Liquid Encapsulant (No Flow Underfill)
60-3 Liquid Encapsulant (Glob Top)
60-4 Liquid Encapsulant (Dam)
60-5 Liquid Encapsulant (Molding)
60-6 Thermally conductive Adhesive
60-7 film adhesive with proper resin and the proper phosphors and photo-initiators
60' adhesive bead with modified rheology for screen printing
60" adhesive fillet
70 adhesive dispenser
72 Substrate
72' PCB
72" High Density Circuit
73 UV source
74 Spacer element
75 Computer Control
76 Mechanical Drive
77 Mechanical arm
78 Mechanical Coupling
79 Platen
79' Vacuum ports
79" Thermode
80 Composite substrate
81 PET component
82 X-ray source
130 Pick & Place
131 Vacuum
132 contact pads
132' Wire Bond
133 metallic lid
133' glass lid
134 Flexible Circuit
140*a* plastic with injection molded features
140*b* plastic with mirror image injection molded features
140*c* bonded plastics
150 PET plastic with well
150' Liquid Crystal Polymer
100 Well joint features
101 protrusion piece
102 fluidic channels in PET
102' fluidic channel in LCP An example of an application and how these steps are used is provided in the following paragraphs. One preferred embodiment involves the bonding of a silicon integrated circuit, either to a substrate or to another integrated circuit (to make a multilayer stack). The penetrating power of X-rays will be such that the X-rays can pass through the uppermost layer of silicon and reach the bond layer, in which the downconverting particles will become stimulated and emit the desired wavelength of light (which may be UV or visible, depending on the particular photoinitiator being used).

Optional steps may include, without limitation: dispensing the adhesive in a pattern that will allow the adhesive to flow under a component through capillary action (e.g., "die underfill" processes); photo-patterning the adhesive; and applying pressure to the adhesive bond before and/or during the curing process.

Other applications will involve the following steps as shown in FIG. 62:

1. (optional) surface prep—the surface must be placed in a state in which the adhesive to be formed can bond to the surface. This prep can include a variety of different methods, including but not limited to, alcohol swabbing, plasma treatment, acid or base treatment, physical abrasion or roughening, a detailed overview of surface preparation was provided.

2. applying adhesive to the substrate—the adhesive can be applied using any desired method, depending on the viscosity of the pre-cured adhesive composition.

3. (optional) optically inspecting the applied adhesive for dispensing quality—this is to ensure that the adhesive has been applied properly, whether evenly coated, applied in drops or lines, etc. This step preferably requires that there be a visual contrast between the adhesive and the substrate to which it is applied. Such a contrast can be provided through the addition of one or more conventional coloring agents to the adhesive, or through the use of color-changing adhesives that change color upon curing.

4. placement of the substrate for cure—this ensures that the pieces to be adhered together are in proper alignment.

5. Curing using X-rays and performing final inspection 6. (optional) Providing real-time closed loop feedback in an automation line (via reel to reel or islands of automation) This permits defects to be detected much earlier in mass production, thus minimizing waste due to misalignment of pieces or incomplete cure Conductive Fillers Optional components may include various organic or inorganic materials and additives to perform desired functions, such as modifying the electrical conductivity and dielectric properties of the cured polymer. Many of these components are well known to those skilled in the art.

Conductive fillers may include finely divided particles of metals including gold, silver, nickel, copper, and alloys such as Au—Pd, Ag—Pd, etc. Other conductive phases that may be used with the invention include $LaB_6$ as well as various conductive oxides and carbon. The conductive filler particles may alternatively be made from small polymer beads or spheres having a conductive coating thereon, such as a thin gold film. The polymer particles may be fairly rigid or they may have some degree of flexibility or compressibility in order to make the final bond more compliant. Plasticizers and flexiblizers can be added Isotropic conductivity may be achieved by using small particles ("small" meaning particles with an average diameter much less than the final bond or film thickness) loaded to a volume fraction that exceeds the percolation threshold so that the resulting polymer composite material exhibits substantial electrical conductivity in every direction. Conversely, the invention may also be used for anisotropic conductive materials, in which a film or sheet contains a monolayer of large individual spherical conductor particles ("large" meaning particles whose diameter is comparable to the final bond or film thickness) loaded to a volume fraction below the percolation threshold so that the resulting material is substantially conductive through the film thickness but is not conductive parallel to the plane of the film.

Other suitable filler materials include various dielectric materials such as metal titanates and zirconates, titanium oxide, etc., that may be added to tailor the dielectric properties of the film. Other inorganic additives may include boron nitride for applications where it is desired to have a bond that is electrically insulating yet thermally conductive.

Organic additives may include several classes of agents familiar in the art. These include, without limitation: plasticizers to modify the mechanical properties of the cured polymer; surfactants and dispersants to modify the rheology of the uncured material to make it easier to dispense as well as to allow any particulate fillers to be adequately dispersed; and solvents and comonomers.

Figure 17:
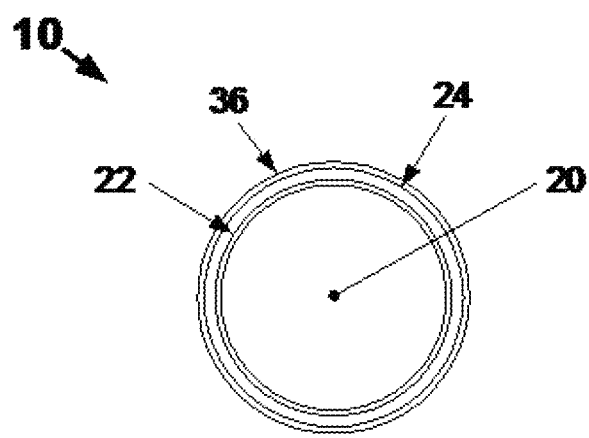
FIG. 17 provides a representation of an embodiment of an anisotropic conductive polymer sphere of the present invention.

Conductive Polymer Spheres:

One example of an anisotropic conductive polymer sphere is generally represented at 10 of FIG. 17. In this example, the sphere consists of an elastic polymer core 20 that is surrounded with a thin layer of plated nickel 22 under plated gold 24 and an outer layer of another, more brittle, thin polymer coating 36. As is well known within the art, Anisotropic Conductive Adhesives (ACA) can be manufactured from rapid (snap-cure) thermo-setting epoxy resins filled with approximately 4% of conductive polymer spheres which have a nominal diameter of 5-microns. The polymer spheres are designed to deform elastically when compressed, exposing the outer gold plated surface, which is then able to establish electrical continuity across the narrow gap between aligned contact pads of stacked IC chips, wafers or other substrates.

Figure 18:
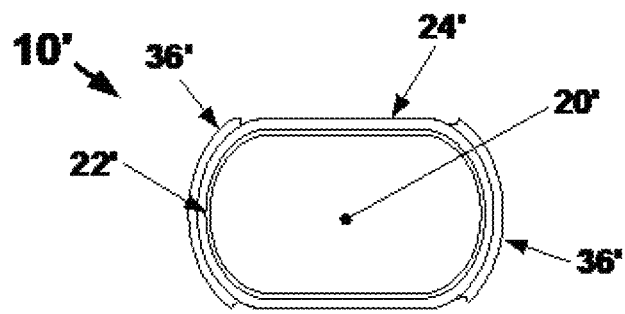
FIG. 18 provides a representation of an embodiment of an anisotropic conductive polymer sphere of the present invention after compression and flattening.

When compressed and deformed the polymer sphere 20' becomes partially flattened, as generally illustrated at 10' of FIG. 18. As the diameter expands under compression the brittle outer polymer coating becomes fractured 36' at the top and bottom contact surfaces and exposes the malleable and partially flattened gold plating 24'. The gold plating still adheres to the partially flattened polymer sphere 20' by means of the plated nickel layer 22', which is also malleable and becomes partially flattened. As the plated gold metal becomes exposed under compression it establishes a metal-to-metal electrical contact with the metal pads disposed directly above and below the partially flattened polymer sphere. Electrical continuity is then achieved across the gap between top and bottom pads around the circumference of each polymer sphere thru the plated nickel and gold layers. This process is further described and illustrated in FIG. 19.

The first essential step of the inventive method is to place a polymerizable adhesive composition, including a photoinitiator and downconverting phosphor, in contact with two or more components to be bonded to form an assembly. As noted above, the viscosity of the adhesive may be varied over a significant range by the choice of monomer(s), the possible use of solvents, the loading of filler particles, etc., as is well understood by skilled artisans.

Many of the inventive compositions will be thixotropic, enabling them to be conveniently dispensed using standard processes familiar in the field of adhesives. In particular, for microelectronics assembly, the compositions may be applied to selected areas using automated needle-type applicators in conjunction with pick-and-place methods. Alternatively, they may be applied in various patterns using printing through screens or masks. Low-viscosity systems, which would typically contain solvents and a minimal amount of inorganic fillers, may be distributed in selected patterns by ink-jet printing.

In order to form an aniostropically conductive bond, the inventive material may be formed into a sheet having conductive balls of the appropriate diameter, cut or diced to a desired size, and placed between the two components to be bonded. It will be understood that in some cases, this process may be repeated in order to make a multilayer stack of any desired number of components.

The second essential step of the inventive method is to irradiate the assembly with radiation at a first wavelength, capable of downconversion by the downconverter to a second wavelength capable of activating the photoinitiator, thus initiating the polymerization of the adhesive.

Applicants contemplate that in a most preferred embodiment, the radiation applied to the assembly after the bond material has been placed will be X-rays. Many industrial X-ray generators are available commercially from a number of suppliers, and the skilled artisan may easily select an appropriate X-ray source based upon routine engineering considerations.

Thermo-Set Adhesive:

With the surfaces held in compression, using an externally applied force, the thermo-set epoxy is rapidly cured in order to maintain the conductive polymer spheres in a state of compression after the external force is removed. A thermo-set epoxy may be rapidly cured by means of an appropriate heat source such as a cartridge heater, microwave or ultrasonic generator, IR heat lamp, laser beam, or various other means to apply heat to the surfaces being bonded. However, the heat must generally be fairly high (>250° C.) in order to achieve rapid curing of the epoxy and often requires that the heat be conducted through the surfaces used for achieving the applied force as well as the chip and/or substrate being bonded together. If the materials being electrically and mechanically bonded exhibit a significant difference in their characteristic coefficient of thermal expansion (CTE), a high state of shear stress may exist between these surfaces after the epoxy is cured and the materials return to room temperature. This shear stress is undesirable, as it may lead to a premature failure of electrical continuity between the aligned contact pads. This problem is more pronounced when there is a large difference in relative size between the materials being bonded.

Several significant advantages may therefore be realized if the epoxy can be cured without the necessity for using high heat. For example, if the epoxy can be cured at room temperature the materials may be joined without any residual shear stress thereby improving reliability. And if the fixtures used for aligning the parts and applying a compressive force between surfaces remain at room temperature, the time required for assembly may be substantially reduced.

UV or Light-Cured Adhesive:

One possible solution for rapid adhesive curing at room temperature is the substitution of a ultraviolet (UV) curable or visible light curable adhesive for manufacturing the ACA adhesives described above. Some literature has been written on this subject, but a fundamental problem arises when attempting to expose the adhesive to sufficient (curing) UV or light energy through optically opaque surfaces that are commonly encountered in microelectronic assembly. Without adequate UV or visible light illumination the epoxy may not fully polymerize. Some manufacturers attempt to remedy this situation by combining properties within the epoxy that allow it to be partially cured with UV-energy followed by a final thermal cure. However, an ideal UV or light-curable epoxy for ACA applications would be realized if it can be fully cured without necessity of an external UV or visible light source or additional thermal-cure steps.

As noted above, various photoinitiator compounds and downconverting materials exist that can convert absorbed higher-energy (X-ray) photons to lower-energy photons (UV or visible light). If an adhesive epoxy is custom engineered to be sensitive (i.e. polymerize) when exposed to the spectral wavelength and energy level of one or more types of these "down-converting" lower-energy photon emitters, included as a "filler" within the epoxy, then the epoxy can be fully cured, even through optically opaque materials, by exposing it to an X-ray source. An added benefit is that the same X-ray energy may simultaneously be detected and converted into an image for quality control purposes.

Figure 19:
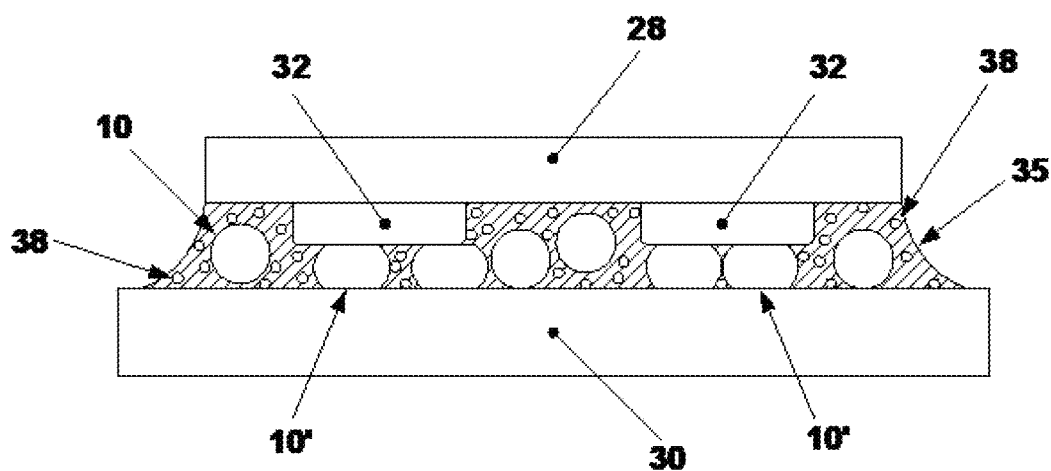
FIG. 19 provides a representation of an embodiment of the present invention using anisotropic conductive polymer spheres in an integrated circuit application, wherein the representation has features exaggerated for emphasis.

An example of an X-ray activated, UV or visible light curable, anisotropic conductive adhesive (ACA) (35) is shown in FIG. 19. Features of the figure are exaggerated to illustrate how an integrated chip (IC) can be assembled as a flip chip device (28) and electrically interconnected to a substrate (30). The bumps (32) on the bottom surface of the flip chip device are raised above the otherwise planar surface of the IC chip. The raised bumps are typically fashioned using either electro-plated or electro-less plating methods and may consist of metals such as nickel-gold, copper-nickel-gold, titanium-tungsten/copper/nickel/gold and other various metals and/or alloy combinations. The raised bumps typically range in height from 5-10 microns above the planar surface of the IC. The raised bumps are typically formed on the chips while they are still part of the whole wafer. However, the substrate will typically not include raised bumps. When assembled in a face-down (flip chip) configuration, the raised bumps on the IC form a difference in thickness of the gap between the surfaces. And when properly filled with a sufficient amount and diameter of ACA polymer spheres (approximately 4% of 5 micron diameter spheres) there is a high probability that one or more spheres will be captured between the flip chip device bumps and the substrate pads (not shown) and partially flattened (10') when a proper amount of external normal force is applied. The "proper" amount of force required is determined experimentally depending on the variable geometries and materials that are being assembled. The remaining AC polymer spheres (10) that fall between adjacent bumps will remain uncompressed and will not generally conduct electricity, since the brittle polymer coating (36) is unbroken.

In the example illustrated in FIG. 19, the X-ray activated adhesive (35) is also filled with small down-converting photon emitters (38) which are engineered to emit lower-energy photons in the UV or visible light spectrum. The amount and size of these down-converting photon emitters would also be experimentally determined, depending on the material properties. In practice, the down-converting photon emitter particles would be smaller than the AC polymer spheres (10 or 10') and would be evenly distributed within the epoxy resin (35).

Figure 20:
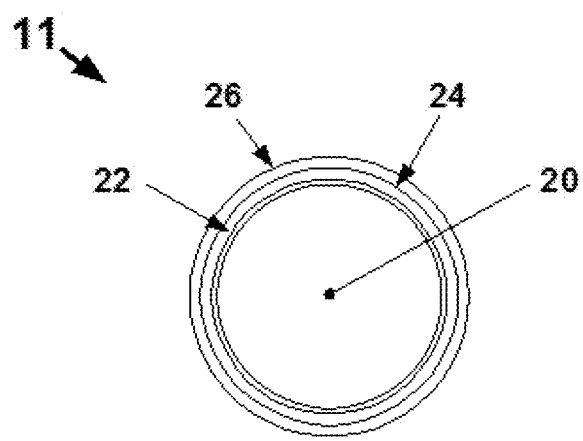
FIG. 20 provides a representation of a further embodiment of an anisotropic conductive UV emitting polymer sphere of the present invention.
Figure 21:
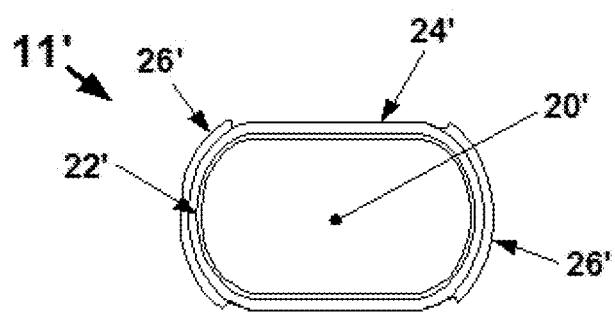
FIG. 21 provides a representation of an embodiment of the anisotropic conductive UV emitting polymer sphere of FIG. 20 after compression and flattening.

Adding the down-converting photon emitters as separate "filler" may adversely effect the viscosity and thixotropic characteristics of the UV adhesive. Therefore, an alternative and better practice would be to substitute the polymer coating (36) of the ACA polymer spheres (10) with a coating (26) consisting of the down-converting photon emitter material(s), to form a new type of anisotropic conductive, UV emitting, polymer sphere (11) as illustrated in FIG. 20. In this example the down-converting photon emitter coating is both electrically non-conductive and brittle in nature, so as to fracture when partially flattened (26') and thereby expose the gold coating (24') underneath, as illustrated in FIG. 21.

Figure 22:
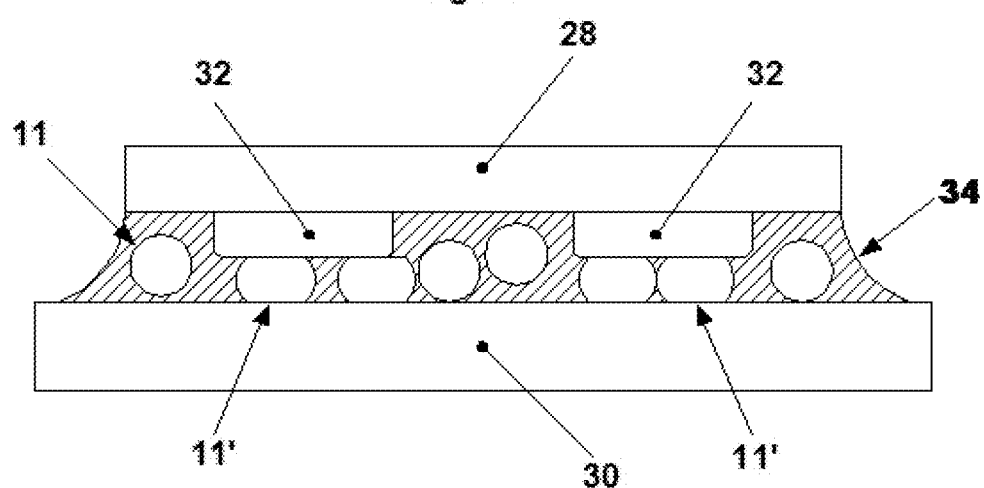
FIG. 22 provides a representation of an embodiment of the present invention using anisotropic conductive UV emitting polymer spheres in an integrated circuit application, wherein the representation has features exaggerated for emphasis.

FIG. 22 is similar to FIG. 19, but illustrates the absence of the down-converting photon emitter "filler" particles (38) and substitution of anisotropic conductive, UV emitting, polymer spheres (11 and 11'), as previously described. These polymer spheres would be similar in size and volume to existing ACA adhesive formulations and therefore would be expected to perform in a similar manner.

Figure 23:
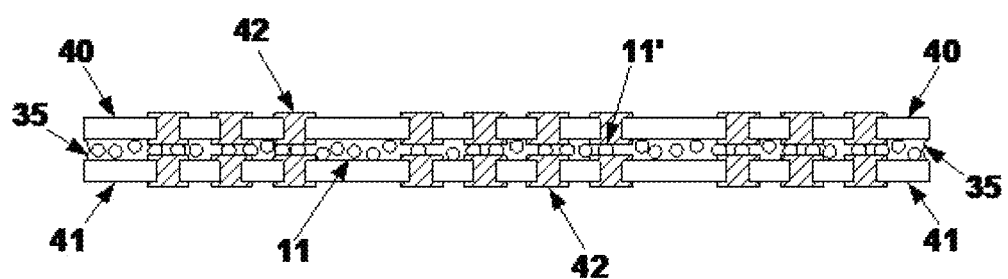
FIG. 23 provides a representation of a further embodiment of the present invention using anisotropic conductive UV emitting polymer spheres.

Another example of an assembly using anisotropic conductive, UV emitting, polymer spheres (11 and 11') is shown in FIG. 23. This illustration shows two similar IC wafers, such as memory chip wafers, stacked one above the other and electrically and mechanically joined together. Both the top IC wafer (40) and bottom IC wafer (41) include "Through Silicon Via" (TSV) contacts (42) that provide a means for routing circuit interconnections from the top (active) surface of the wafer to pads arrayed across the bottom surface of the wafer. In this manner electrical functions that are present at a pad on the top (active) side of the wafer may also be present on the opposite or bottom (non-active) surface of the wafer; much like a thru-hole connection enables signals to be routed through a printed wiring board (PWB). The TSV contacts include small, raised, annular or square pads on the top and bottom surfaces that form contact surfaces for electrical connection through the partially flattened polymer spheres (11'). When the wafers are properly aligned and compressed the X-ray activated, UV or visible light curable, ACA epoxy (35) is cured by exposing the assembly to an X-ray source.

X-ray Aligner and Bonder Description:

To commercially implement the UV adhesive bonding technology described above, it is deemed desirable to have equipment engineered to safely provide the correct X-ray exposure dosage in order to activate (in situ) the UV or visible light curable adhesive, and to simultaneously image and record the resulting cured bondline using the same X-ray energy. Some examples of suitable X-ray aligner and bonders are partially illustrated in FIGS. 24A-C, 25A-C and 26A-C.

Figure 24A:
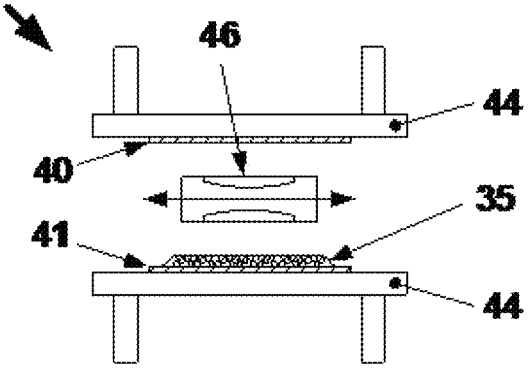
FIGS. 24A-C provide representations of an embodiment of an X-ray aligner and bonder according to the present invention.
Figure 24B:
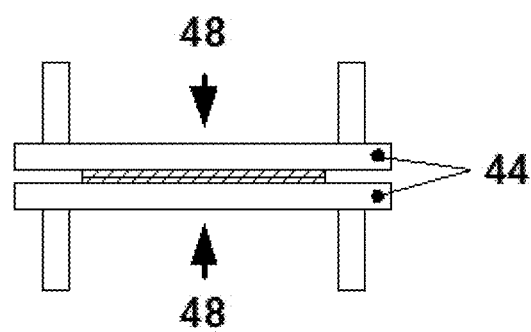
Figure 24C:
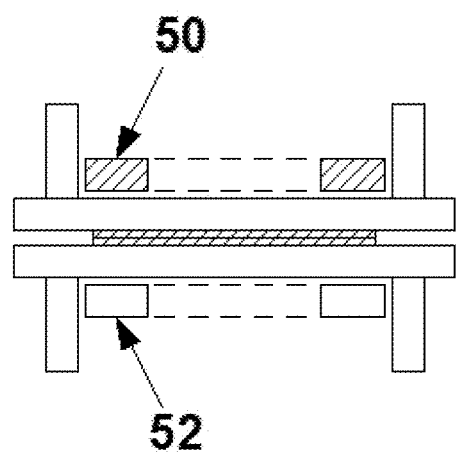

An X-ray wafer aligner and bonder (39) of FIG. 24A is designed to enable wafer-to-wafer alignment and bonding using an X-ray activated, UV or visible light curable, ACA epoxy (35) without need for applying external heat to the wafer surfaces being joined. The bonder includes two vacuum plates (44), of sufficient size to hold a top IC wafer (40) and bottom IC-wafer (41), that are spaced apart sufficient to enable a split field prism and lens device (46) to be temporarily inserted and scanned between the surfaces, as shown. The prism device is used to precisely align the wafer surfaces with respect to one another, either manually or by automated means, prior to the wafer surfaces being compressed together. The prism device provides a means to view and superimpose fiducial images from multiple locations on the bottom surface of the upper wafer with similar fiducial images on a top view of the lower wafer. Once these fiducial images are superimposed and accurately aligned, the split field prism and lens device are removed and the wafers are brought together under an applied force (48) as shown in FIG. 24B. The applied force compresses and partially flattens the anisotropic conductive polymer spheres (10' or 11') trapped between the aligned flip chip device bumps (32) and/or Thru Silicon Via (TSV) contacts (42) of each IC on the two wafers, as previously described and shown in FIGS. 19, 22 and 23. Once the wafers are under an applied force, sufficient to enable the ACA polymer spheres to partially flatten and establish electrical conductivity across the juxtaposed bumps or contacts, an X-ray Exposure Device (50) and X-ray imaging device (52) are brought into position, as shown in FIG. 24C. X-ray exposure device (50) is used to generate a field of high energy photons that stimulate the fluorescent coating of the down-converting spheres which then spontaneously emit UV light of the correct wavelength and luminosity to cause the UV resin to rapidly cure by photo initiation. As the high energy photons pass through the materials they may also advantageously be detected on the surface of an X-ray imaging detector (52), positioned directly across from the X-ray exposure device and on the opposite side of the wafer vacuum plates. The X-ray imaging detector is designed to produce high resolution X-ray images of the bonded surfaces using analog and/or digital circuitry that is immune to damage from the X-ray source. Data from the X-ray imaging detector is collected and processed into high-resolution digital images, as either individual photos and/or continuous video, for data (archival) storage and/or image processing to provide a means for process and quality control.

Figure 25A:
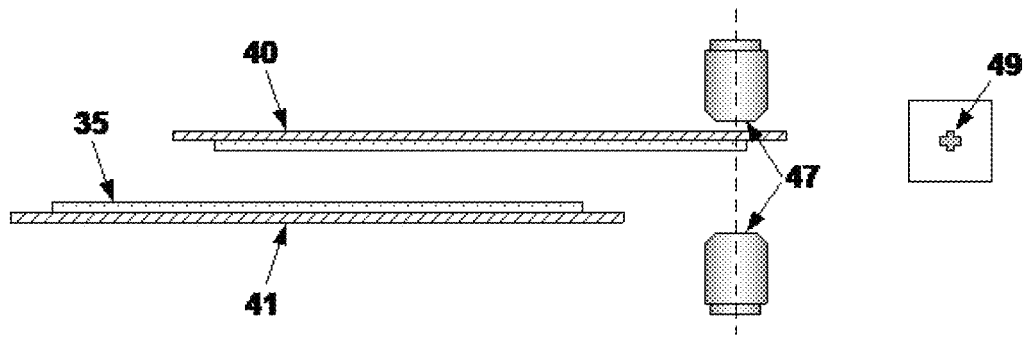
FIGS. 25A-C provide representations of a further embodiment of an X-ray aligner and bonder according to the present invention.
Figure 25B:
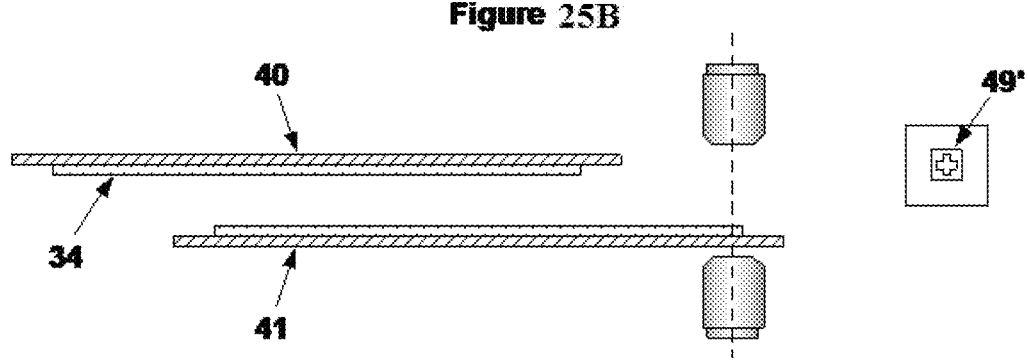
Figure 25C:
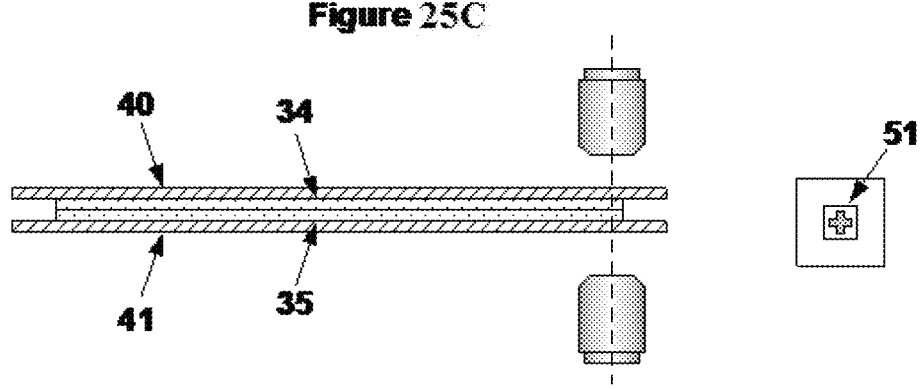

An alternative technique to achieve wafer-to-wafer alignment is illustrated in FIGS. 25A-C. In these illustrations, the movable split field prism and lens devices (46) are replaced by a pair of fixed lens (47) that remain stationary as the wafers are individually moved over or under the field of view of the lens-pair to locate alignment fiducials (49 and 49') disposed at multiple locations near the edges of both top and bottom IC-wafers. Alignment fiducials for the top IC-wafer (49) differ from the bottom IC-wafer (49') and are designed to be superimposed over each other to provide an optical reference for precise alignment in the x-axis, y-axis and theta-angle. When properly aligned, the fiducial images (49 and 49') as shown in FIGS. 25A and 25B would be superimposed, as illustrated at 51 of FIG. 25C.

Disposed on the top and/or bottom IC-wafers (40 and 41) are coatings of a UV-curable, ACA filled epoxy (35) and/or compatible matrix epoxy resin (34). In some applications it may be desirable to apply epoxy coatings on both top and bottom 1C-wafers with differing compositions and viscosities to enhance the bonding process. For instance, the bottom epoxy coating may include ACA conductive spheres (10 or 11) within a high-viscosity resin matrix, whereas the top IC-wafer may be coated with a compatible resin that has a lower viscosity and does not contain any ACA conductive spheres. The differing compositions and viscosities of the coatings allow for a reduction in the amount of ACA spheres required to achieve reliable interconnect between stacked chips or wafers, enables better retention of individual ACA spheres where required on the bumped pads during application of the compressive force during bonding, and helps to reduce formation of voids within the cured epoxy.

As described earlier, once the top and bottom wafers are optically aligned with respect to one another, the surfaces are brought together and compressed under an applied force to enable the ACA polymer spheres to deform and establish electrical continuity between juxtaposed pads of the individuals IC devices on the wafers; thereby establishing a 3-D interconnect between surfaces. Since the pads that are to be joined may not have identical coefficient of thermal expansion (CTE) values, the polymer spheres provide a compliant interface that helps to absorb expansion mismatch during thermal cycling, thereby maintaining proper electrical continuity.

The resin and the photo-initiator materials were obtained from BASF. The materials were weighted in the proper ratios using a balance having +/0.1 grams measurement accuracy.

The materials were mixed in a laboratory environment with DCA (a class 10,000 clean room). All materials handling was done in a fume-hood. The laboratory had a fluorescent light source to light the room while the fume hood had a controlled light (no UV component to it).

The substrates used to demonstrate bonding included glass, polycarbonates, poly ethylene terephthalate, polyimides, cellulose (or paper), cross-ply carbon-prepreg composites, PEC, ABS, Mylar, intrinsic silicon, doped silicon, silicon based integrated circuits.

In some cases, the materials were mixed in the proper ratios then they were transferred to syringes and subsequently centrifuged to remove air-bubbles. In other cases, the materials were placed in syringes but not centrifuged. Yet in another case the materials were enclosed inside of the mixing cups. Depending on the specific density of the materials, a high level or a low level of sedimentation was observed.

The materials preparation further included the addition of dispersants in an attempt to control sedimentation. In these cases the surface of the phosphors was modified to enable the attachment of dispersants. The materials were then mixed inside resin materials and photo-initiators under heat. The materials were hand mixed using a stainless steel spatula that did not react or contaminate the raw materials. No materials contaminations were at play for the most part. The temperature used for mixing varied from room temperature to 80° C. The mixing was better when conducted at elevated temperatures.

Raw Materials Sources

The sequence of mixing was investigated. Various mixing sequences may work. However, a preferred embodiment of preparation is obtained by heating the resin materials to 80° C. followed by adding the photo-initiators and mixing. The mixing and heating of the resin and photo-initiators is continued until a clear (air bubble free) solution is obtained. Mixing is done gently to avoid shearing the resins and the photo-initiators. Heating was found to have a significant impact in this step. The phosphors are added third followed by mixing. In this case the mixing is continued until the phosphors are well dispersed inside the solution before adding a filler material. Phosphor materials having particle size distributions in the micron scale are best. The filler materials are added last. In the best mode the filler material is $Y_2O_3$:Gd nano-particles and a fractional amount of Aerosil (or active silica). Filler materials in the nanoscale particle size worked best. It is of interest to note that in this case the $Y_2O_3$:Gd consists of 5 to 60 nm particles and that the Aerosil material has fibrous like morphology. It is also of interest to note that the $Y_2O_3$:Gd particles can agglomerate and could form micron level aggregates. The resolution as what these aggregates could help is not clear.

The original intent was to determine the proper UV response and the adhesion between substrates at room temperature and with no other UV light source except from the conversion of X-ray into UV. However, the mixing of raw materials was performed with the fluorescent room light on. It was discovered that the elapsed time under room fluorescent light influenced the outcome of the cure extent. In essence, the UV light from the room assisted in photo-initiating the chemical reaction. The longer the elapsed time for mixing under uncontrolled light, the more cure extent was achieved under X-ray energy. A controlled photo-catalysis initiation was performed to take advantage of this discovery. This was called flashing the material with a UV light prior to curing under X-ray.

The initiation of the photo-catalytic reactions in adhesive materials was achieved through UV-flashing by the following sequence in the preparation. The raw materials were prepared under controlled light only. The photo-catalysis initiation was performed using a set time exposure to UV light soon after the dispensing/application of the adhesive or during the dispensing/application of the adhesive prior to the placement of the top substrate. The sandwiched part was then placed under X-ray energy and cured farther. The materials that were subjected to flashing cured faster than those that were not subjected to flashing. Based on cure hardness the flashing of select chemistries was done in less than (7.5 min) while the same select chemistries took longer (12.5 minutes) when no flashing was applied.

Figure 26A:
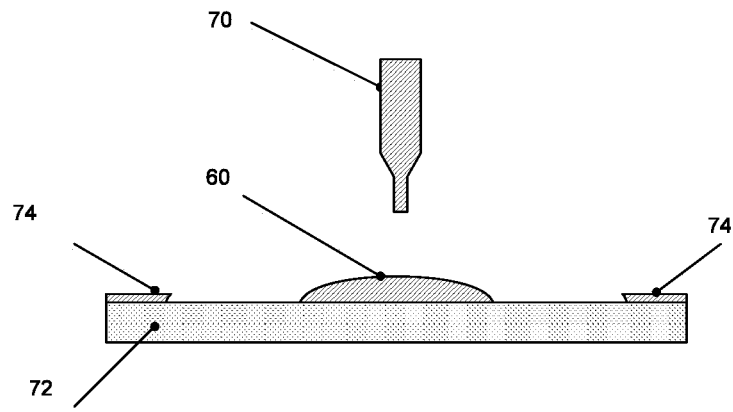
FIGS. 26A-C provide representations of another embodiment of an X-ray aligner and bonder according to the present invention.
Figure 26B:
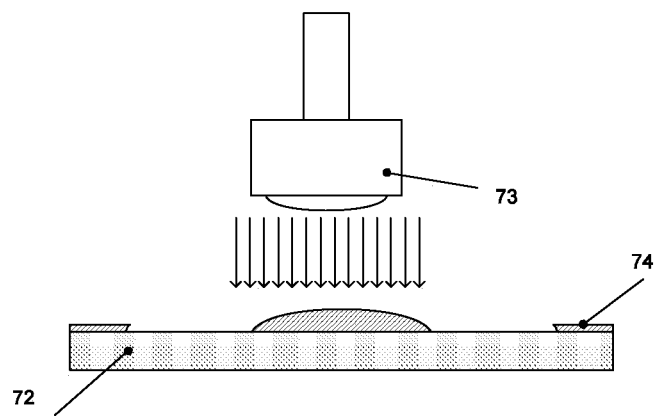
Figure 26C:
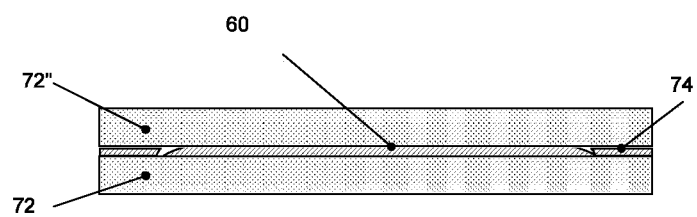

The flashing is further exemplified in the following FIGS. 26A-C. A hand held or automatic piston pump dispenser 70 was used in this case. The adhesive bead 60 was dispensed on substrate element 72 illustrated in FIG. 26A. The substrate in this case was polycarbonate. However it can be appreciated that the inventive method is applicable to other substrate materials including composites and PET among others. The dispenser applied the bead using a needle gauge 22. No phosphor segregation was observable using a piston pump of the appropriate gauge. FIG. 26B. The bottom substrate 72 had a spacer element 74 made of Kapton and having a thickness of 90 microns.

Figure 27:
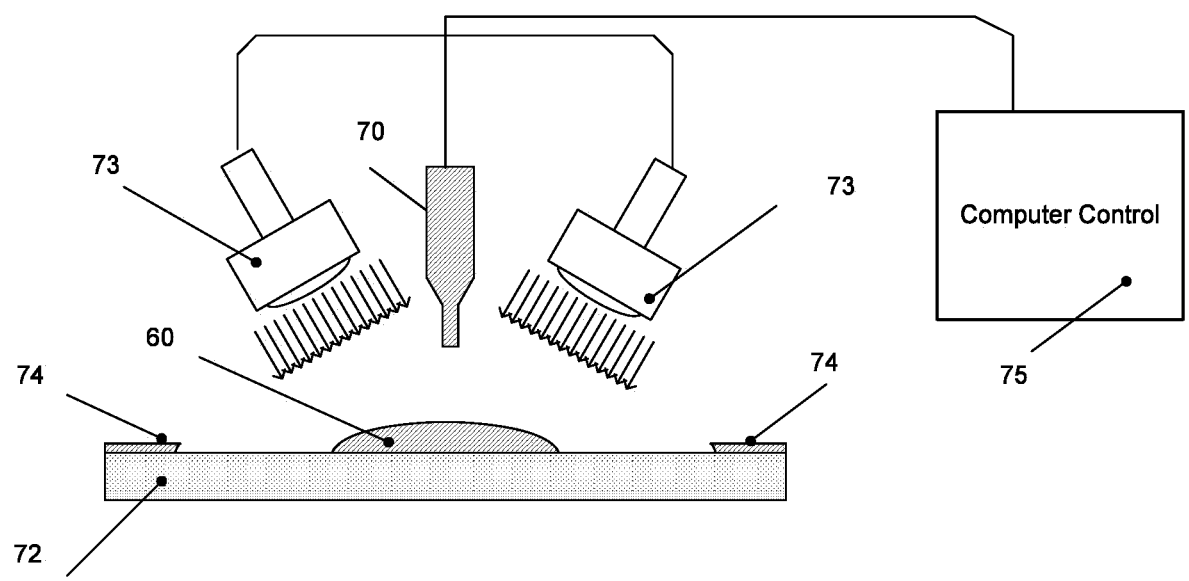
FIG. 27 provides a representation of an embodiment of a stationary dispense system having computer control and the ability to program UV intensity and UV source with ON/OFF time.

A UV source 73 was used to apply energy from within UVA range centered around 365 nm see FIG. 27. After 15 seconds to 25 seconds of UVA exposure another substrate element 72" was applied on top. The assembly hence formed was taken to the X-ray system for curing. It is recognized that the UV flashing can be done for longer times as needed; however, there a practical limitation to UV flashing.

Figure 28:
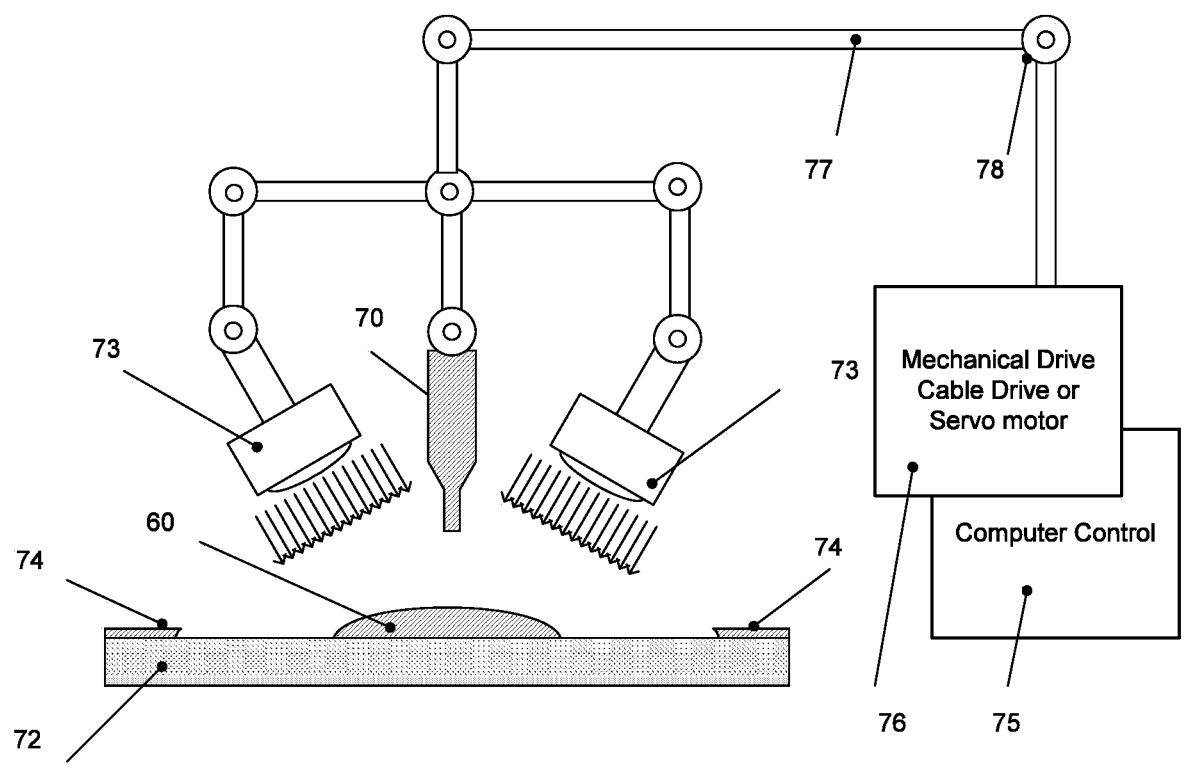
FIG. 28 provides a representation of a further embodiment of an automatic dispenser having a mechanical drive system and computer control, particularly useful for UV flashing.

Combining a UV light with the dispensing step is possible (FIG. 28). By adding at least one UV light source to an automatic dispenser and by adding the necessary control logic 75 to turn on the UV light in a controlled manner (UV intensity and UV elapsed time) at the end-of or during the adhesive dispense, this UV flashing can be easily be scaled to high volume manufacturing.

The UV flashing is an effective method that allows the reaction to be boosted from a cost effective source. Subsequently to the flashing and almost immediately, the substrates to be joined need to be placed against one another. The adhesive bead is then placed inside an X-ray system. The X-ray energy can effectively complete the reaction of an adhesive bead that is inside a no line of sight region of an assembly.

The ability to dispense and flash the adhesive can be done with a high degree of repeatability using an automatic dispenser having a mechanical drive consisting of a servo motor or a cable drive. In this case the robotic system is equipped with mechanical coupling mechanisms (or articulations) 78 and a mechanical arm 77 to enable the placement of the adhesive dispense needle in a precise manner over a large area. The mechanical system further comprises a drive system 76 based on a servo motor or simply a cable drive.

Figure 29:
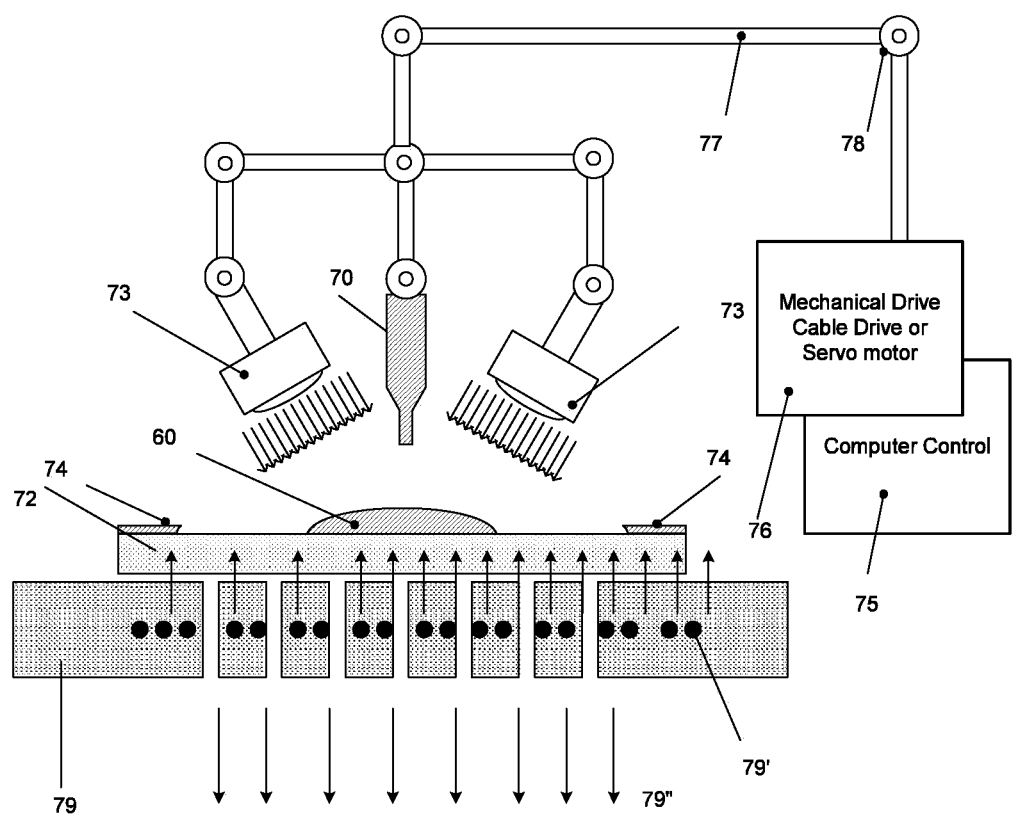
FIG. 29 provides a representation of another embodiment of an automatic dispenser having a mechanical drive system with computer control and a heated platen with vacuum apertures.

The system can further comprise a platen 79 that is equipped with vacuum ports 79' and a source of heat 79" such as a thermode (refer to FIG. 29). The vacuum helps secure the substrates in place. The thermode increases temperature of the substrate. Adhesives at slightly elevated temperature can flow much more readily than at room temperature. The viscosity of adhesives is typically lowered at elevated temperatures until curing starts taking place in which case the viscosity starts increasing. their viscosity, this is beneficial in specific applications but not others. Some applications require the wicking of adhesives through capillary forces underneath substrates or into porous materials.

In most applications the adhesion is promoted by having elevating the temperature. To avoid running into the coefficient of thermal expansion mismatch between two substrates, the upper most temperature to which the substrate can be heated should be below its glass transition temperature (Tg). Below Tg the substrate expands at one coefficient of thermal expansion and above its Tg the substrate's at a higher coefficient of thermal expansion. As long as the temperature remains below Tg the adhesion could be promoted.

The UV flashing is accompanied by the curing of the outer layer (or the formation of a skin). This outer layer or skin reaches higher cure extent than the inside portion of the bead. Upon the formation of this skin, the bead becomes unpractical because of the hardened outer layer becomes an impediment to the controlled placement of the top substrate. The formation of an adhesive bond line through the juxta-position of 2 substrates becomes hard to do.

In other examples, the steps described above were repeated without any UV flashing. So that the adhesive bead was prepared under controlled light inside the fume-hood and kept shielded from light exposure until we exposed to the adhesive bead to X-ray energy. In this case the adhesive curing was conducted for 12.5 minutes to reach adequate mechanical bonding.

The flashing can be beneficial for other applications described in the following example and illustrated in FIGS. 30A-D. A screen printer can be used instead of an adhesive dispenser. The substrate element 72 is positioned under the screen 90. A screen aperture 90' can be positioned above the substrate 72 but not contacting it. A blade 91 is passed with an adequate pressure to force the adhesive through the screen aperture. The screen is subsequently removed. The dispensed adhesive 60' is exposed to UV energy for a controlled time (between 15 and 25 seconds). The top substrate is then positioned on top of the adhesive. The sandwiched bead can be cured in X-ray for 7.5 min and successfully bond the 2 substrates.

In one case the substrate was cross-ply carbon composite 80 in FIG. 31A-C. The adhesive 60 was applied to the adhesive. Subsequently a component made of PET 81 was placed on the uncured adhesive bead. The assembly hence formed was turned around and placed under an X-ray source for curing. No flashing was used in this case. The adhesive bead cured in 15 minutes.

The X-ray curing system can have an additional source of radiation, namely UV. The UV radiation from the UV source 73 can be used in conjunction with the X-ray radiation from X-ray source 82. This enables the cure of adhesive beads that have a portion that is exposed to the outside world and a portion that has no line of sight. An example is described in FIG. 32 where a fillet 60" has direct line of sight and can be cured using radiation.

The fillet 60" plays in an important role in flip chip applications where stresses are maximal at the corner of the IC chips. The curing of the fillet 60" can be done using an adequate recipe to minimize stresses. This would imply that the curing using UV radiation can be done simultaneously, before or after the X_Ray radiation whichever minimizes the inherent stresses.

In some cases dispensing 2 adhesive beads can be desirable. A dispenser 70 contains adhesive 60 while dispenser 70" contains adhesive 61. The 2 beads are dispensed sequentially. A novel adhesive applicator is conceived. The novel dispenser 64 has 2 chambers and 2 coaxial needles as illustrated in FIG. 33A-C. The inside container 62 contains adhesive 61 while the external container 63 contains adhesive 63. Furthermore, the novel dispenser has a coaxial needle containing needle 64' and 64" through which adhesives 61 and 60 flow respectively.

The adhesives were applied to the substrates using various methods from simple to more complex. In the simplest form the adhesive formulations were scooped from the mixing cup using a spatula and deposited on the top surface of one substrate. In other cases the adhesives were placed in syringes and hand pressed through a needle with an 18 to 22 gauge. In other cases the materials were dispensed through the needle of EDF air piston pump (also using 18 to 22 gauge needles). In some cases the substrates had a spacer element sandwiched between the substrates to keep the materials from being squeezed out from between the substrates. The adhesive cure was demonstrated for adhesive bead thicknesses from 60 microns to 1000 microns.

|  | Resin percent in Adhesive | 2100 percent in adhesive | 184 Weight percent in adhesive | Ratio of Adhesive % | Phosphor % by Weight | Phosphor Type | Cure Hardness |
|---|---|---|---|---|---|---|---|
| Around 100 microns | 0.94 | 0.02 | 0.04 | 0.75 | 0.25 | CaWO$_4$ | Yes |
| Between Glass Slides | 0.94 | 0.02 | 0.04 | 0.6 | 0.4 | CaWO$_4$ | Yes |
|  | 0.88 | 0.04 | 0.08 | 0.75 | 0.25 | CaWO$_4$ | Yes |
| Around 250 microns | 0.94 | 0.02 | 0.04 | 0.75 | 0.25 | CaWO$_4$ | No |
| Between Glass Slides | 0.94 | 0.02 | 0.04 | 0.6 | 0.4 | CaWO$_4$ | No |
|  | 0.88 | 0.04 | 0.08 | 0.75 | 0.25 | CaWO$_4$ | Yes |

In some cases this was achieved using a polyimide film, while in other cases the spacer elements were glass beads. The curing of the adhesive thickness of the adhesive beads was successfully demonstrated at 60 microns to 250 microns. These thicknesses represent adhesive beads that would be compatible with applications such as B-staged films and chip on board applications. In other cases the adhesive bead was between 500 microns to 1000 microns. These thicknesses represent adhesive beads that would be compatible with applications such as hermetic sealing applications.

The control over the rheology and thickness of the adhesive beads was achieved using filler elements such as AEROSIL and nanoparticles of doped $Y_2O_3$. Gadolinium was found to be the preferred doping elements in these cases. In order to achieve thicknesses of 500 microns and above the adhesive formulations had between 0.5% and 5% of filler.

In some cases, the adhesive bead was applied between 2 polycarbonate substrates and kept in this configuration for 24 hours. No-flow or displacement was observable. The adhesive bead was therefore made to provide the end-user with enough work and pot life after dispense and to tolerate interruptions of the work in process during manufacturing. This is significant because no scarping of the work in process after dispense is required.

| Formulations | 1 | 2 | 3 | 4 | 5 | 6 |
|---|---|---|---|---|---|---|
| Resin | 5 | 5 | 5 | 5 | — | — |
| Resin (shadow cure) | — | — | — | — | 5 | 5 |
| PI (369) | 1.3 | 1.3 | 1.3 | 1.3 | — | — |
| PI (2959) | — | — | — | — | 0.5 | 0.5 |
| LaOB:Tm | 1.5 | 2.5 | 3.5 | 2.5 | 2.5 | 2.5 |
| $Y_2O_3$ | — | — | — | 0.3 | — | — |

-continued

| Formulations | 1 | 2 | 3 | 4 | 5 | 6 |
|---|---|---|---|---|---|---|
| AEROSIL | 0.2 | 0.2 | 0.2 | 0.2 | 0.2 | 0.2 |
| CABOSIL | — | — | — | — | — | — |
| MEKP | — | — | — | 0 | 0.1 | — |

It was found that recipe number 2, 3 and 4 cured faster than other formulations. However adhesion was compromised when excess photo-initiator was used. For this reason recipe 4 worked best. It cured faster that recipe 2 and had better adhesion than recipe 3.

It was discovered that the uniformity of dispersion can be important to the process. The more uniform the dispersion the better results in terms of adhesion. When clusters of phosphor rich and or phosphor poor areas were noticeable, the cure was localized and the overall adhesion over a surface area was not good. When the photo-initiator is saturating the mix (excessive amount of photoinitiator), the adhesion at surfaces is compromised as there is a migration of un-reacted photo-initiator at the surfaces.

Materials Information.

The first substrate is positioned in place. The location of the substrate and the mechanical registration is recorded. The adhesive is then applied to the first substrate. The adhesive may contain a contrast agent to resolute a bead pattern on top of the first substrate. In such case a first substrate that is black should not have an adhesive color that is black. A white or off-white colored bead would be more suitable. A whitening agent like $TiO_2$ can be used as the contrasting agent. In this case the color of the substrate is irrelevant, since the inspection can be performed using X-ray radiation, the inspection of the bead can simply be done regardless of the visible color contrast.

Figure 34:
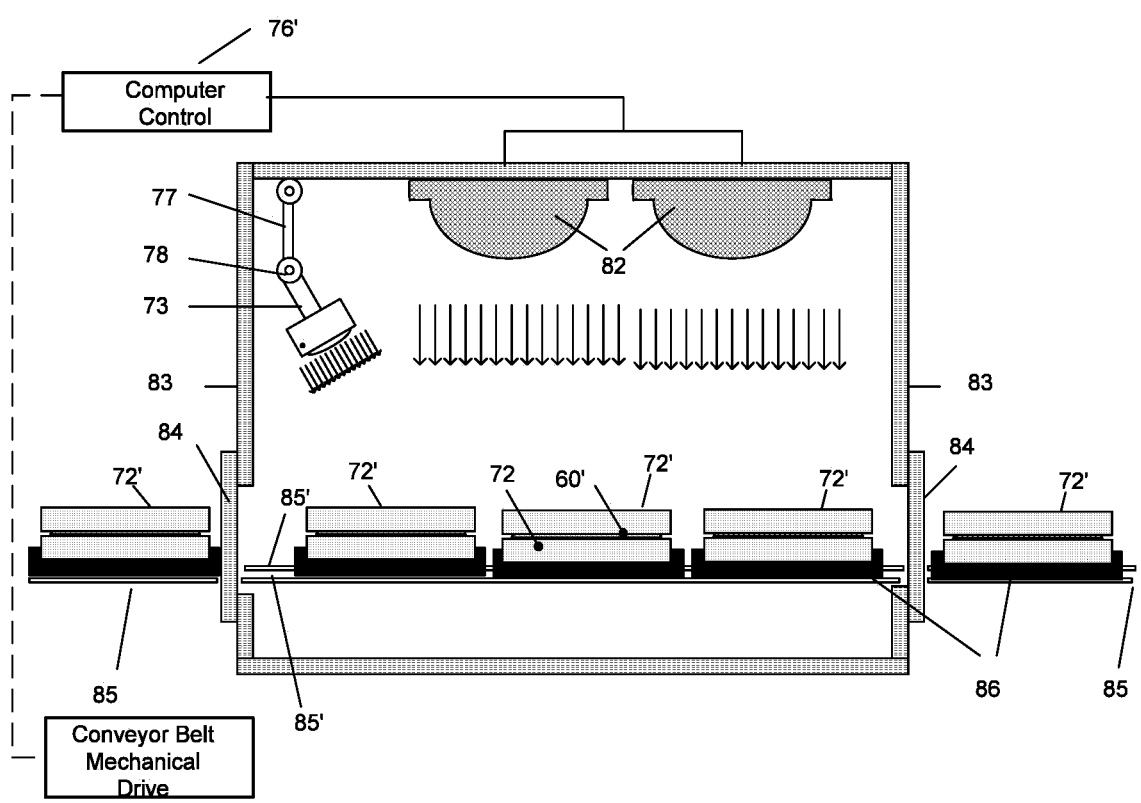
FIG. 34 provides a representation of one embodiment of X-ray system for use in the present invention having automated doors and an internal UV lamp.

The second substrate is then positioned in place on top of the adhesive bead and the first substrate. The assembly is transported under the X-ray system that would perform a combination of X-ray based steps namely inspection and cure or one step consisting of curing. The X-ray system comprises various elements that can be automated to satisfy manufacturing requirements. FIG. 34 illustrates some of these elements that form the X-ray curing system intended by the invention.

The step of X-ray radiation is preferably done in an enclosure 83 that stops the radiation from leaking to the outside world. The enclosure 83 can be made of various materials that include heavy metals such as lead. A single assembly 72' can be held static or can be moved during cure inside the enclosure. Such movement could include a rotation movement that can be achieved using a turn table. Such movement could also include a translational movement that can be achieved using an external conveyor belt 85 and an internal conveyor 85'. Both the internal and the external conveyor belts work in synch to shuttle parts in and out of the X-ray enclosure. The door 84 can open up and close down to shuttle assemblies 72' in and out of the X-ray radiation chamber. When the door is open (or up position) the X-ray energy is off to adhere to safety measures. The X-ray enclosure can have automated doors with sensors linked to a controller 76'. The enclosure can have doors that open up and down to shuttle at least one assembly in and out of the X-ray enclosure for irradiation leading to curing. Furthermore, the assembly to be cured can be positioned inside a process fixture 86. The process fixture carries with it the assemblies 72'.

More than one assembly can be placed inside the X-ray machine. The configuration having multiple assemblies can vary to maximize the loading of parts inside the X-ray curing system. As illustrated in FIGS. 35A and 35B, 2 conveyors are juxtaposed one next to the other to increase the packing factor (number of assemblies) inside the X-ray system within plane. Because of the depth of penetration at the correct levels, conveyors can be disposed within planes (FIG. 35A) and across planes (FIG. 35B) inside the X-ray curing system.

An additional advantage of X-ray curing resides in its ability to cure various size adhesive beads residing within different products using the same curing parameters. As an alternative embodiment, the X-ray machine can have more than one source, permitting curing of different assemblies at the same time (see FIG. 36). This presents an advantage and enables the manufacturer to cure different product mix inside the X-ray curing system. Assemblies 160 and 160' can be cured at the same time. This means that a product change over is easier and that the system is flexible in meeting cure requirements.

X-ray systems with the capability of programming recipes including pulsing up to 30 times per sec can be done. A level of control over the kvp as well as amperage can be done to exert control over output power as well as photon energy which in turns means control over depth of penetration.

Additionally, curing time and efficiency can be adjusted as desired by adjustment of various parameters, including, but not limited to, temperature, radiation source intensity, distance of the radiation source from the adhesive composition to be cured, and photon flux generated by the radiation source.

X-ray delivery head is on one side of the assembly, either above the adhesive bead or below the adhesive bead which can be described (though not exact) that the adhesive bead is generally perpendicular to the direction of propagation. In some cases the adhesive bead is generally parallel to the X-ray radiation path. It is recognized however that the X-ray radiation is emitted in a flood beam have multiple directions around one predominant direction of propagation.

Metals and metallic coatings limit the penetration of X-ray radiation. For this reason, X-rays need to be oriented appropriately when curing integrated circuits having metallic traces and coatings. In these case scenarios the preferred orientation of the bead is parallel to the X-ray direction of propagation. As illustrated in FIGS. 37A-C, two configurations are possible. In one case FIG. 37A, the assemblies are oriented vertically to achieve the preferred orientation, in the other case FIG. 37B, the X-ray source(s) is mounted in the appropriated orientation to achieve the desirable alignment between bead and direction of propagation. FIG. 37C provides a different view of the alignment between assembly 160 and the X-ray.

Wafer Bonding

After the wafer alignment is completed (using the method described in FIGS. 24A and 24B), the wafers are clamped together using a clamping fixture 88. The clamping fixture allows the wafers to remain aligned during transport. The clamping fixture contacts the wafers on the wafer back side with a depth typically within the exclusion zone of the wafers. The wafers can be placed on a rotating table 89 with a rotating arm 87 as illustrated in FIG. 38A and FIG. 38B. The rotating table is capable of taking withstanding pressure up to 40 kN. The pressure can be applied using 2 mirror image rotating tables. The clamping fixture 88 can be removed once the 2 rotating table have been engaged.

Since X-ray curing is done at room temperature or done at below the glass transition of the polymers used for bonding, not much pressure is required after the placement of the wafers on top of one another. Similarly, when a die is placed on a wafer surface, not much pressure is required.

The die on wafer application could use the same wafer set up described in FIG. 39. However in the die on wafer bonding application the X-ray is aligned at an angle which leads to more depth of penetration over the area array of the ICs 40' disposed on top of the bottom wafer 41. The plane of the bond line in this case is at 45 degrees vis-à-vis the direction of propagation of the X-ray.

Safe Designs Of X-Ray Systems (See FIGS. 40A-C)
Contact-Less Design for Clean Rooms (See FIGS. 41-42)

Containers that can be raised up and down to gate the assemblies 160 that enters the processing chamber. Part of the cavity 90' can be raised to enable batching of assemblies 160.

Chamber 120 is fixed in place. The bottom of the cavity of chamber 122 can be raised up and down to enable positioning wafers 41 that enter the processing station. The movable bottom does not touch the upper processing chamber (no contact between 120 and 122.

Bonding Fasteners on Composites (See FIGS. 43A-B)

A composite panel 80 is dispensed with adhesive 60. The metallic fastener 110 is placed on top of the substrate 80 using a pick and place system that is pneumatically driven (112). Both the pick and place 112 and the adhesive dispenser 111 are mounted on KUKA robot 113. The X-ray sources 82 are placed at a slight angle to couple to the bottom of the bolt 110.

More Specific Applications:

The following figures show various applications in semiconductors pertaining to packaging and encapsulation. These include: glob top, dam and fill, molding (PMC, insertion molding) and flip chip underfill.

Figure 44:
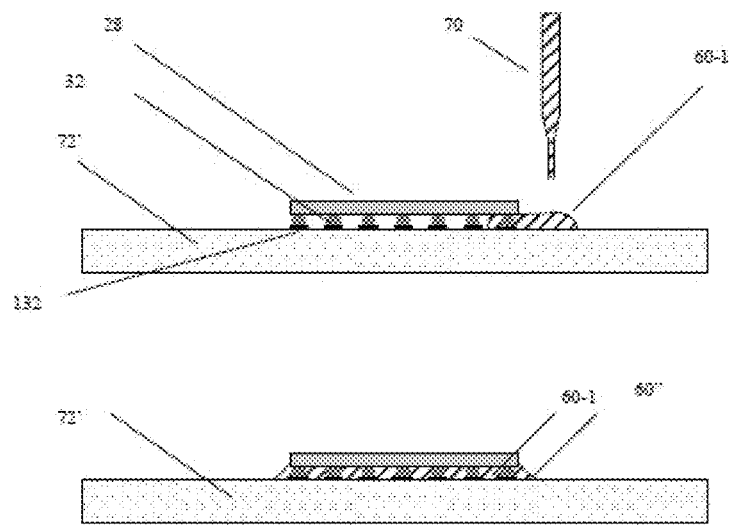
FIG. 44 provides a representation of use of an embodiment of the present invention for production of an underfill assembly.

Underfill Under a Flip Chip:

An IC 28 is soldered in place in such manner that bumps 32 enter into electrical contacts with electrical pads 132. A desirable adhesive 60-1 is applied by dispensing system 70 (see FIG. 44). If the substrate is heated to 20° C. above room temperature the adhesive wicks under the chip by virtue of the capillary forces set between the chip and the substrate 72. Once the adhesive is dispensed and wicked under the IC, the adhesive is ready for curing and optionally an inspection is performed prior to curing. The standard method is to inspect the adhesive using optical means. However, since the adhesive 60-1 is loaded with phosphors that have absorption characteristics in the X-ray regime, the inspection can be performed using X-ray radiation. The inspection using X-ray can reveal any striations that may exist under the IC 28. The uniformity of the adhesive can be determined to see if the adhesive has separated into resin rich or resin poor regions. The adhesive can be subsequently cured with X-ray.

The curing in this case can be done at room temperature and the X-ray is best coupled from the lateral side of the IC. In this case the direction of propagation is parallel to the plane of the adhesive bead.

Underfill for a High Density Circuit

Figure 45:
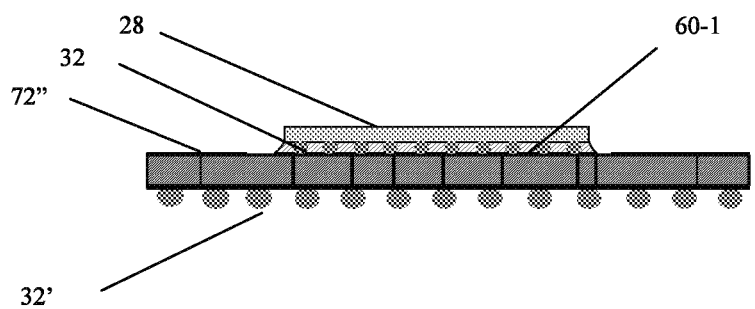
FIG. 45 provides a representation of use of an embodiment of the present invention for production of an underfill on a high density circuit.

A similar process can be applied if the substrate is a high density circuit (72"). Once the assembly is formed, the assembly can be placed on the mother board of a PC or a server using solder bumps (32'). This process is similar to the one used for mounting logic assemblies (e.g.; microprocessors and high density interconnect devices). FIG. 45 illustrates the various elements.

Figure 46:
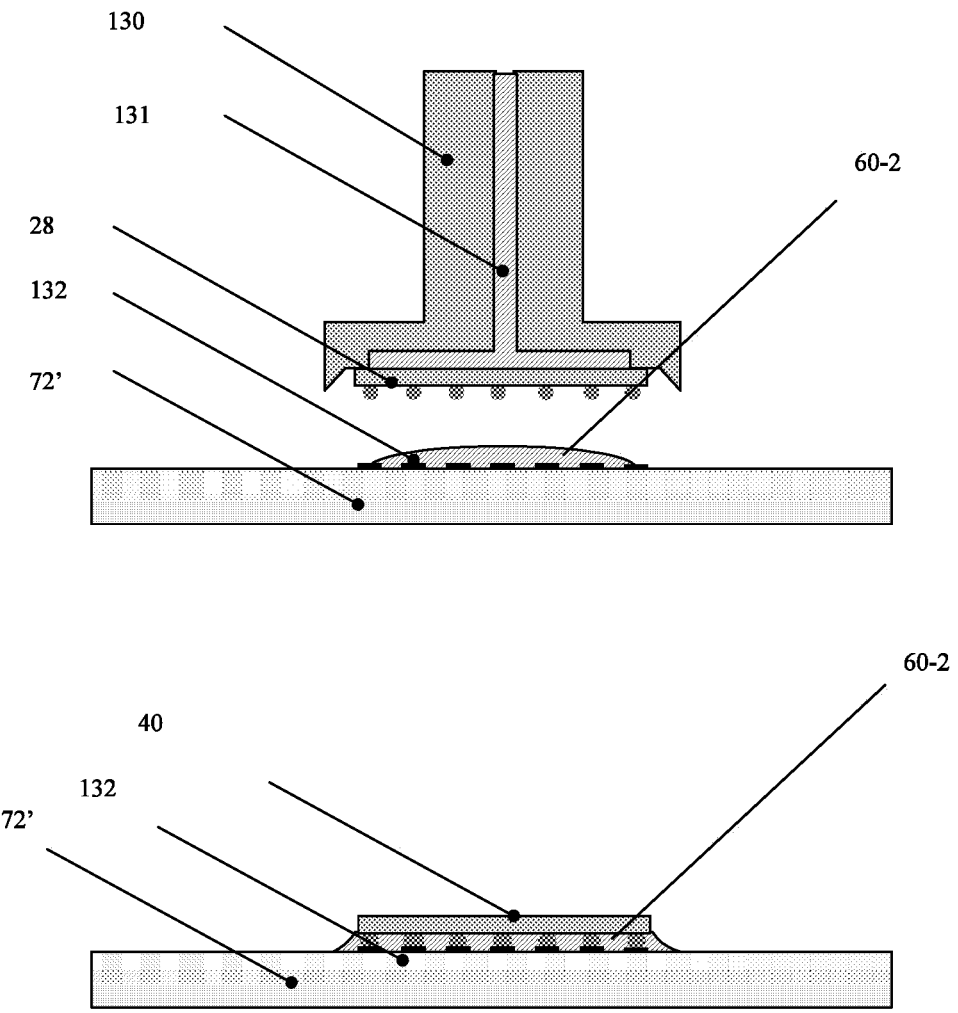
FIG. 46 provides a representation of use of an embodiment of the present invention for production of a no-flow underfill assembly.

No Flow Underfill:

To avoid the combination of time delay that takes place during adhesive wicking and the soldering process to connect the IC (28) onto substrate (72'), an encapsulant (60-2) can be dispensed on top of a substrate (72') above the area array of contact pads (132). See FIG. 46. An optical inspection is performed. A chip is picked using a programmable "Pick & Place" (130) having provisions for vacuum (131). An active alignment is performed before the chip is placed onto a PCB (72') in such manner that the IC bumps (32) enter into electrical contacts with PCB electrical pads (132). The no-flow adhesive can be inspected and cured using X-ray.

Figure 47:
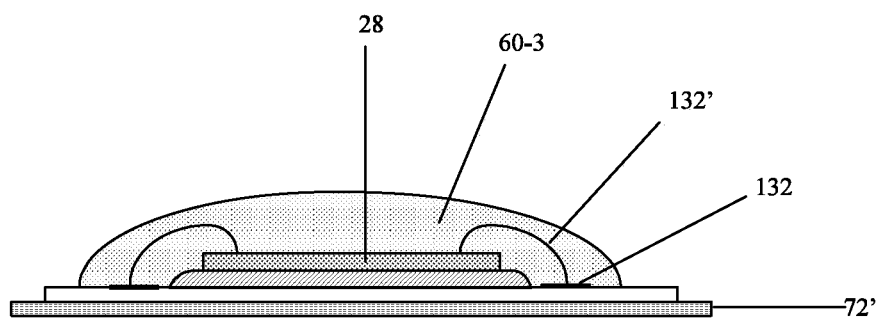
FIG. 47 provides a representation of use of an embodiment of the present invention for glob top encapsulation.

Glob Top Application:

The glob top applications comprise dispensing an electronic polymer on top of an IC (28) that has been die attached onto a PCB (72') and wire bonded to establish electrical contacts between the active area of IC (28) and the electrical pads (132) disposed on the PCB board (72') See FIG. 47. The special adhesive (60-3) containing the appropriate phosphors and photo-initiators can be applied to the IC (28) and enough time is allowed for the electronic polymer to flow and to cover the IC (28) and wire bonds (132'). The assembly is then inspected using X-ray radiation and cured using an X-ray radiation treatment or recipe. The X-ray treatment can consist of pulses of controllable duration appropriate to harden the adhesive without inducing any damage to the assembly.

Dam and Fill

Figure 48:
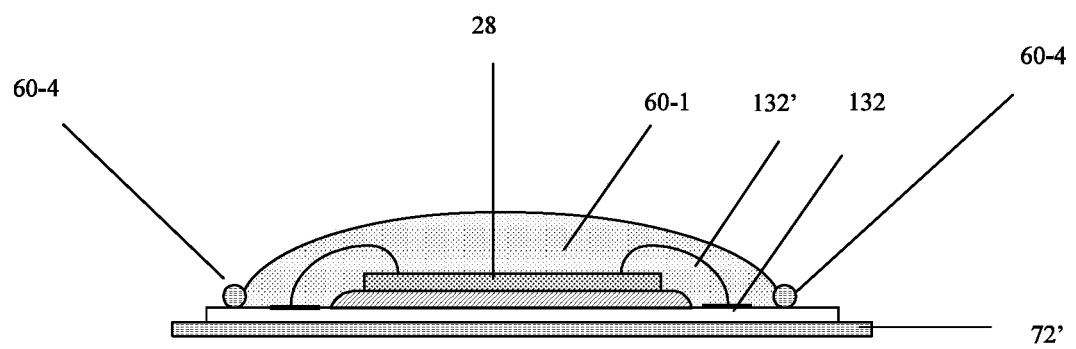
FIG. 48 provides a representation of use of an embodiment of the present invention as a dam-and-fill adhesive.

In some applications it is advantageous to apply a dam (60-4) or the first adhesive bead and subsequently cure the first bead prior to dispensing an encapsulant (60-1) containing the appropriate phosphors and photo-initiators required for X-ray curing. The current technology allows co-curing of both 60-1 and 60-4 using X-ray radiation. See FIG. 48. The amount of phosphors loaded in formulation 60-4 can be deliberately high to cure faster than 60-1.

Molding/Post Mold Curing

Figure 49:
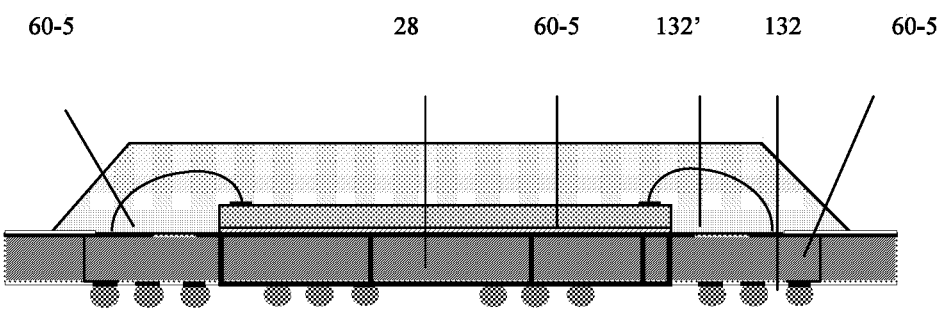
FIG. 49 provides a representation of use of an embodiment of the present invention in encapsulation through molding.

Another standardized way of applying the encapsulation is through injection molding. The resin is applied at the mold level. In this case the IC (28) is attached to the substrate (72") and then inserted into a mold. The mold is then clamped at high pressure and a liquid resin at high temperature is injected at high pressures to fill the spaces between the wire bonds (132') and the IC (28) See FIG. 49. The injection molding step is then accompanied by an elongated heat treatment. The present invention is enabled through the use of a low-viscosity resin (60-5) that contains the appropriate phosphors and photo-initiators. After the injection molding at low temperature is performed, the X-ray inspection and X-ray curing can take place. The benefits of using the present invention are various but the most pronounced benefit to release all the stresses that can be established post molding. This eliminates most thermal annealing steps required for stress release. These stress release steps can take up to 4 hours which increases the Work-In-Process and does not lead to favorable economics.

Lid Sealing for MEMS and Miroprocessors

Figure 50A:
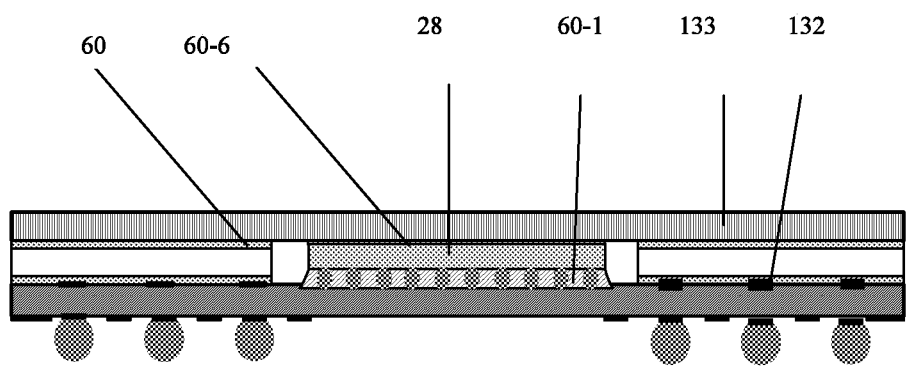
FIGS. 50A and 50B provide representations of use of embodiments of the present invention for lid sealing of logic devices and MEMS devices, respectively.
Figure 50B:
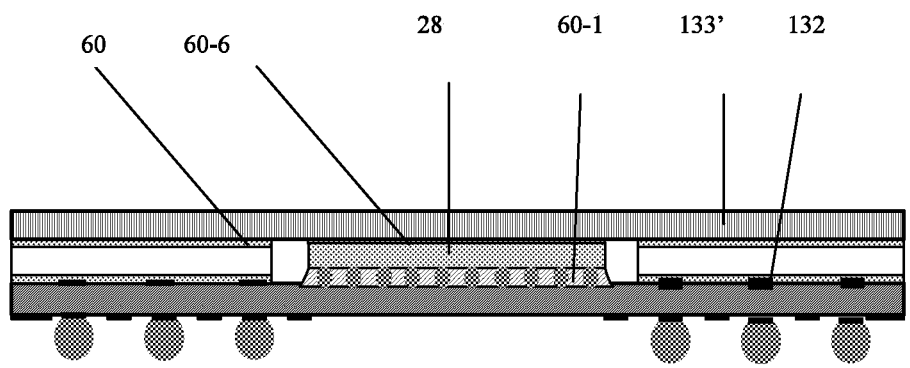

Another application that pertains to semiconductors and MEMS is lid sealing See FIGS. 50A and 50B. In this application three different adhesives can be used. The combination of 3 different adhesives can be used: 1—An adhesive bead (60), 2—an underfill adhesive (60-1), and 3—thermal conductive adhesive (60-6) that connects IC 28 with a lid 133. For semiconductors the lid 133 is typically metallic. For MEMS applications the lid 133' could be glass.

Micro-BGA Fill Encapsulation

Figure 51:
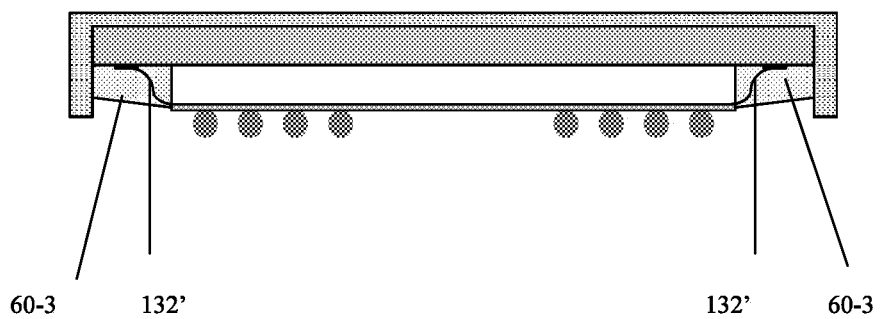
FIG. 51 provides a representation of use of an embodiment of the present invention in glob top encapsulation of a micro ball grid array.

A micro-ball-grid-array can be encapsulated in much the same way that was described for the glob top encapsulation. The configuration of the assembly is different than a chip on board application but the encapsulation of the wire bonds 132' remains the same. (see FIG. 51) An appropriate encapsulation 60-3 with the proper viscosity is prepared to contain the amount of photo-initiators and phosphors to cure under X-ray.

Figure 52:
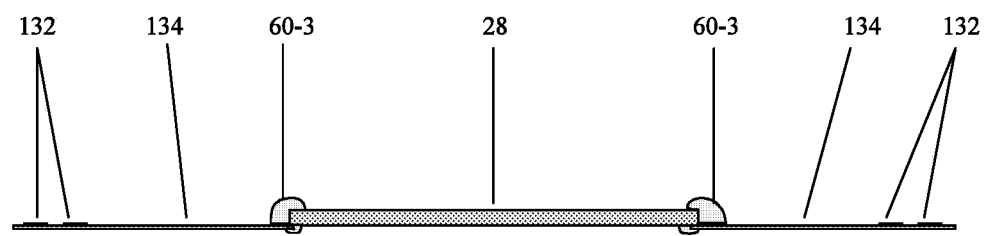
FIG. 52 provides a representation of use of an embodiment of the present invention in encapsulation of TAB bond areas between a flex circuit and an integrated circuit (IC).

Tab Bonding:

Tape automatic bonding (TAB) technique can be enhanced by the current application. TAB is used to electrically connect a flexible circuit 134 with a semiconductor IC (28) see FIG. 52. The flexible circuit contains electrical pads 132. The encapsulant 60-3 can be disposed on the TAB area. The application of the encapsulant is then followed by X-ray inspection and cure.

MicroFluidics

Figure 53:
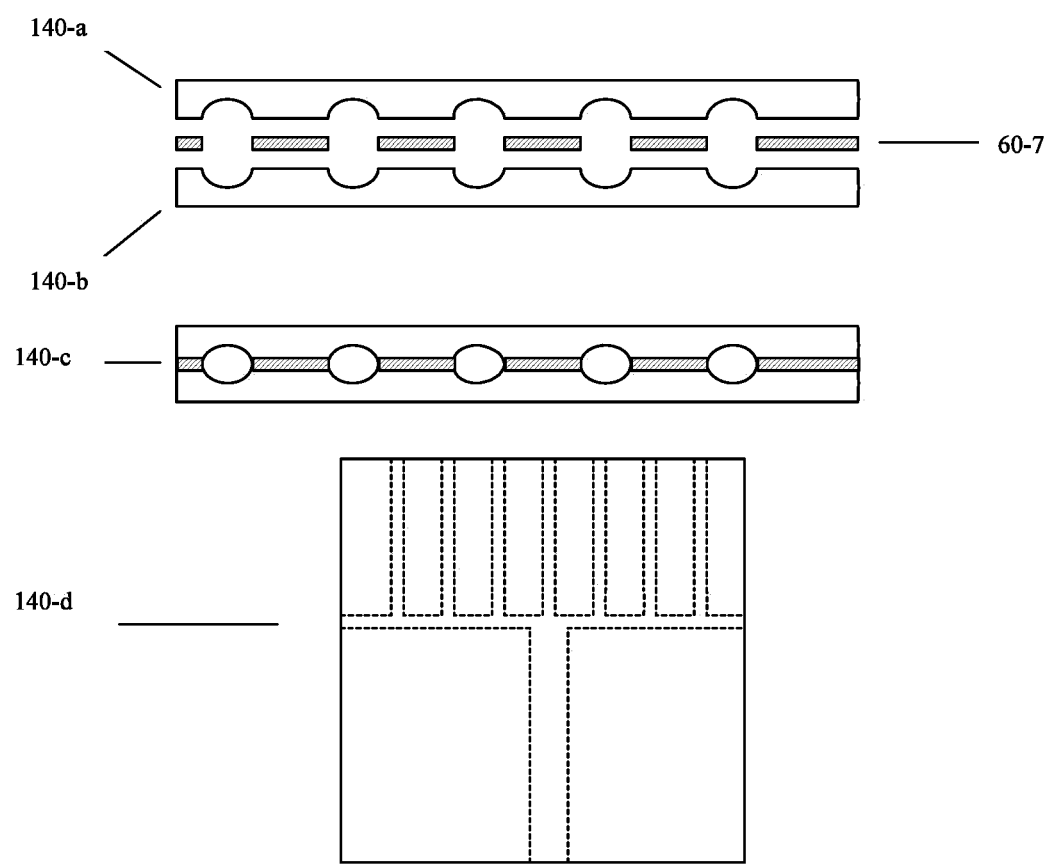
FIG. 53 provides a representation of use of an embodiment of the present invention in bonding of plastic devices having mirror image features using a film adhesive.

The joining of plastic 140-a to plastic parts 140-b that has mirror image features can be used to build functional plastic containers that house fluids and that have usable fluidic channels that can channel fluids from one side of the container to the other. The 2 pieces of plastics having mate-able features are joined together using a film adhesive 60-7 to form piece 140c. (illustrating a cross sectional view). The film 60-7 has the proper resin and the proper phosphors and photo-initiators. The plastic housing formed is illustrated as part 140d (top view). See FIG. 53.

Figure 54A:
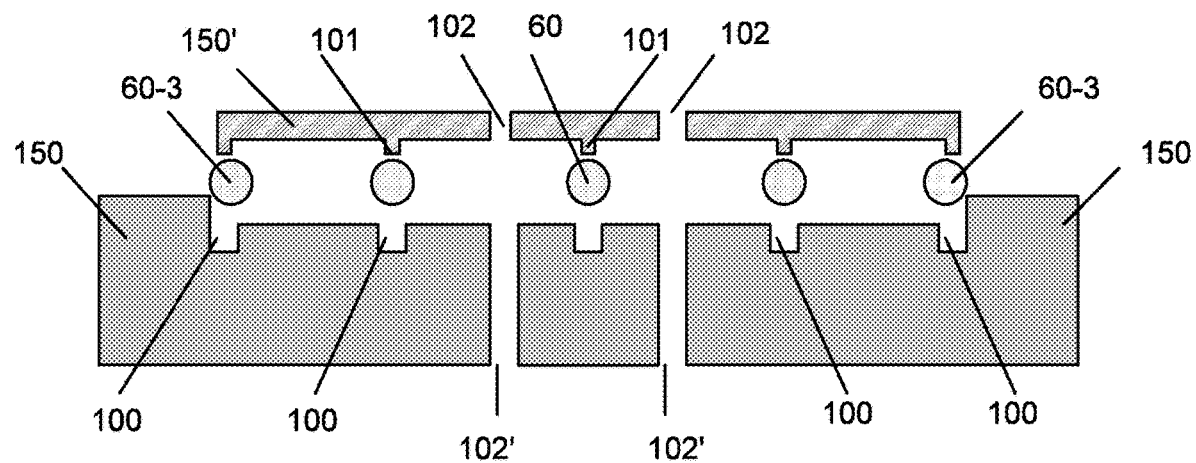
FIGS. 54A and 54B provide representations of use of an embodiment of the present invention in formation of sub-assemblies having fluidic channels.
Figure 54B:
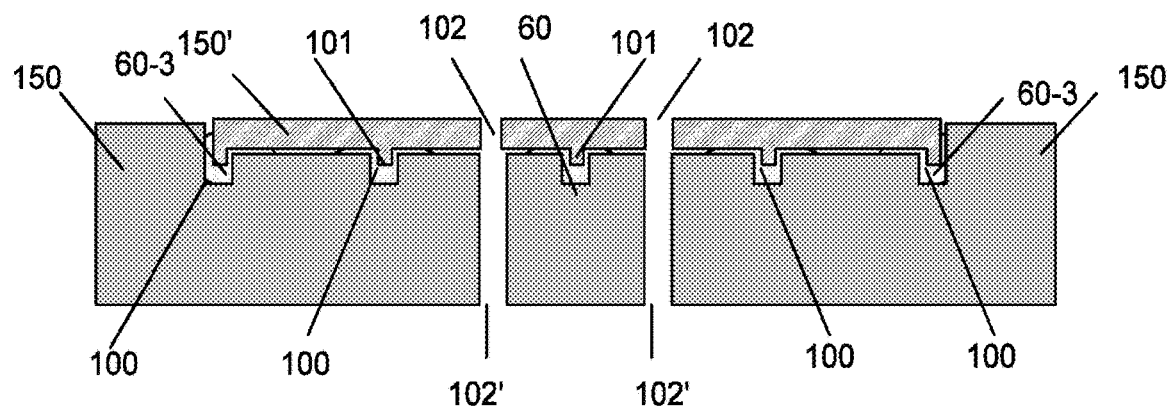

The fluidic channels can be formed using multiple pieces of plastics. The cross section of a PET plastic is shown in 150. The PET has well joints as shown by groves 100. The fluidic channels 102' are aligned with the fluidic channels 102 present on another plastic such as Liquid Crystal Polymer 150' In turn the sub-assemblies hence formed can be used to form fluidic devices. An example of such subassemblies is provided. Each part of the subassembly can have conduits and interlocking features to allow apertures to be aligned. The adhesive bead 60-3 is dispensed and allowed to cure using X-ray. See FIGS. 54A and 54B.

The subassemblies are collapsed controllably. The protruding features 101 enter into the well joint 100. These features enable the obtainment of a hermetic seal since a fluid (liquid of gas) has to travel through the split well that is formed when the protruding feature 101 is engaged inside the well joint 100. The travel distance increases and the hermetic seal is enhanced.

Yet another example includes when a flexible circuit 134 having contact pads 132. The flex 134 is TAB bonded to IC 150 using adhesive 60-3. The IC 150 has a resistive heating network that can increase the temperature around fluidic channels or apertures 102. The fluidic channels 102 are aligned with apertures or fluidic channels 102' that exist on plastic parts 145-d. The IC 150 is bonded using adhesive 60. The fluidic channels 102' connect with fluidic reservoirs 152. These reservoirs can contain Ink or insulin. See FIGS. 55A and 55B. When the flex assembly is wrapped around the housing 145-d the adhesive film 60-7 is activated to bond the outer walls of 145d with the flex 134.

The plastic joining does not have to use mirror image plastics nor does it have to use similar materials. In fact dissimilar materials can be used to form plastic housing for insulin pumps or inkjet containers.

Formation of Ink Jet Cartridges

Ink jet cartridges are typically made of a plastic housing made of a thermoplastic moldable resin, such as polyethylene terephthalate (PET), polyethylene, or polysulfone for example, as the base material. Polysulfone describes a family of thermoplastic polymers that have toughness, mechanical stability and ink resistance.

Typically, a print head made of silicon, has numerous nozzles that are used as ink outlets. The nozzle array on the silicon and the ink reservoirs are connected through a manifold structure having fluidic channels. The fluidic channels are employed to direct the inks of different colors from the primary reservoirs to appropriate printhead nozzle arrays.

Multicolor cartridges have a plurality of ink reservoirs, often three ink reservoirs. In such three ink cartridges, each of the reservoirs contains a primary color. These reservoirs need to be isolated from one another. The separation between the compartments has to be hermetic to avoid ink mixing between the various compartments. A plastic piece is adhesively bonded to seal the separate reservoirs.

The joint of interest that seals or separates the various reservoirs must be made to withstand the prolonged contact with inks. Inks happen to be aggressive from a chemical stand point. Furthermore, the sealing joint needs to be able to overcome the mechanical stresses that may exist over the product's functional life and the pressure differential that needs to be regulated between atmospheric pressure and the internal pressure in the reservoir.

The ink reservoirs and the ink channels, the plastic structures and manifolds necessary to form the multicolor cartridge can be assembled from multiple injection molded plastic parts. The most economical way is to injection mold as one part all of these parts. However, the lid seal and the tri-chamber separation cannot be injection molded as a unitary body, since it is required to have accessibility to the reservoirs. Regardless, whether the cartridge is formed from three pieces, or more than three pieces, two process methods are typically used to bond plastics: Ultrasonic energy welding and thermally curable adhesives.

The problem with ultrasonic welding is that it does not work with dissimilar materials. The other method consists of using adhesive materials to bond the various parts together. The various plastics parts in this case can be of similar or dissimilar materials provided the adhesive is subjected to enough thermal energy.

The application of thermal energy necessary to cure the adhesives leads to thermal expansion of the plastic parts. The thermal expansion mismatch between different materials results in thermally induced stresses locked at the interface of the various materials.

The print head is connected to a flexible circuit using a TAB bonding method. The print head rests on an adhesive bead that bonds the print head to the manifold containing fluidic channels. The print head contains nozzles that can be fired by the electrical signal that feed a resistive network built on the silicon. The electrical signals that are selectively applied to specific nozzles results in the heating of the select nozzles and therefore leads to the controllable ejection or squirting of ink droplets. The ink droplets are directed to the print media like paper to form patterns leading to words, images and the like.

The present invention adhesive composition can be used in the formation of inkjet cartridges, such as those described above or in formation of inkjet cartridges according to the conventional art, such as U.S. Pat. Nos. 7,832,839; 7,547,098; or 7,815,300, for example, the contents of each of which are hereby incorporated by reference.

Figure 56A:
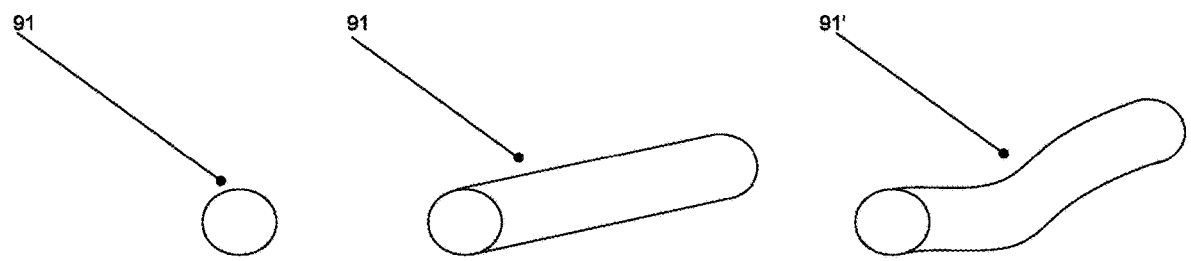
FIGS. 56A and 56B provide representations of leaky optical fiber elements that can be used for curing in the present invention FIGS. 57A and 57B provide representations of an embodiment of the present invention using leaky optical fiber elements.
Figure 56B:
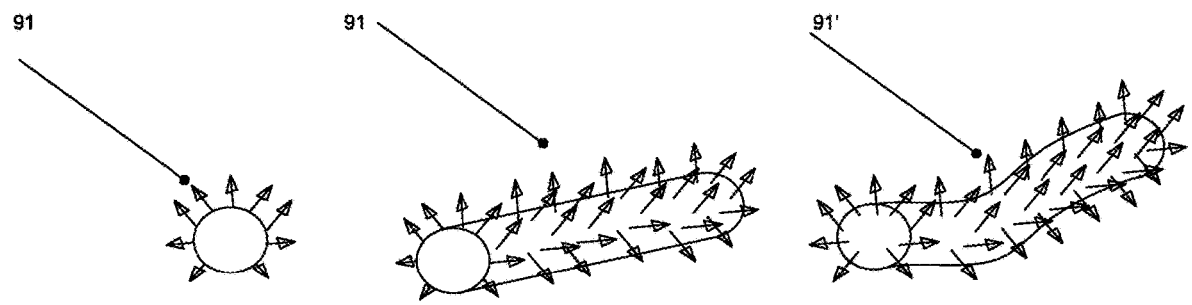

Leaky Optical Fiber Element:

Fiber element 91 can be straight or can be flexible to adopt various shapes. The fiber element leaks UV energy around its core and along the direction of propagation of the UV light. When light is coupled from its ends the light propagate along the fiber and leaks UV lights to its environment. (see FIGS. 56A and 56B).

Figure 57A:
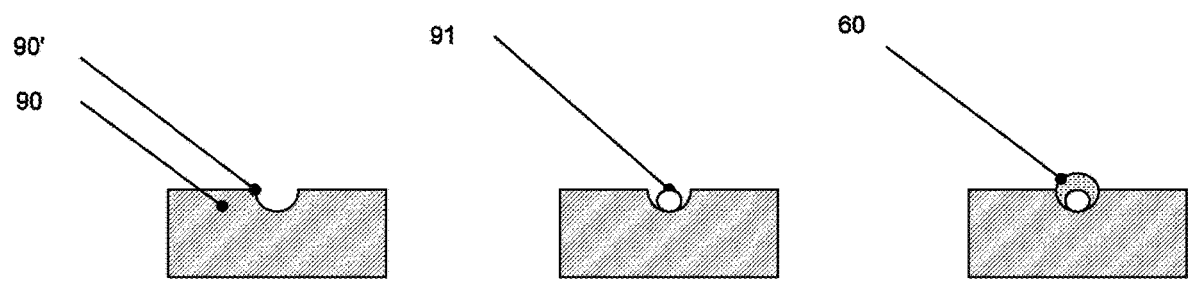
Figure 57B:
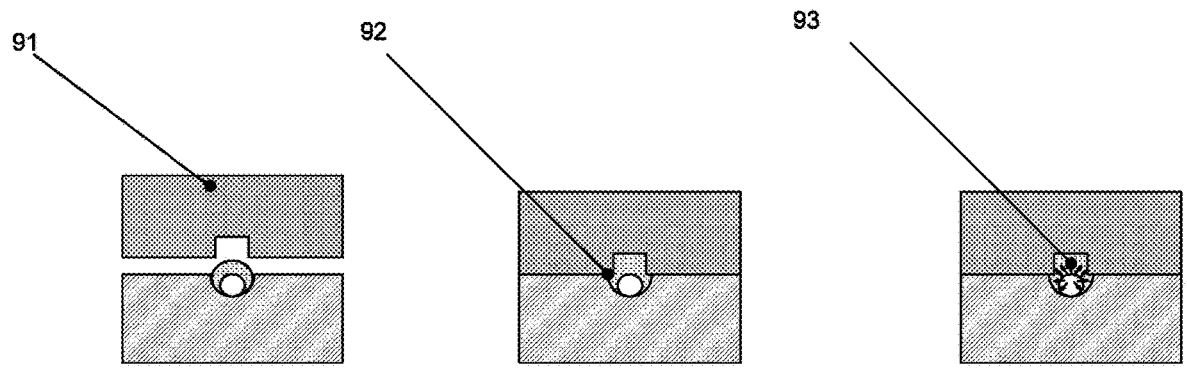

The fiber element is inserted in a joint between 2 plastics. An adhesive is dispensed around the fiber and the assemblies are collapsed together. The curing can therefore be achieved by coupling UV to the external sides of the fiber element to distribute UV light to the inside of the assembly. (See FIGS. 57A and 57B)

UV Ink for Digital Printing Presses

The $CaWO_4$ phosphors and $CaWO_4$:Pb emits in the visible and UVA under x-ray energy. Both these phosphors have a notoriously slow decay time. This phosphor keeps on emitting visible and UV light even after the initiating energy has stopped. The emission remains strong for 60 to 100 seconds after x-ray energy irradiation has stopped.

For this reason, the $CaWO_4$ as well as the $CaWO_4$:Pb can be applied for a delayed curing application such as UV inks. The UV ink offers the possibility of rapid cure under UV light. The inclusion of nano-particle size phosphors that have light modulating capability from x-ray and extreme UV to a desirable UVA and visible range are particularly preferred. The initiating radiation can flash (short burst exposure) the ink and the included phosphors with delay decay time can keep on emitting UV radiation that can cure the ink.

These special inks can be used in digital presses equipped with EUV or x-ray sources to flash activate the phosphors with slow decay times. The web-speed can therefore be accelerated from 400 feet per minute to over 900 feet per minute by virtue of the sustainable UV emissions that can keep on curing the inks from within the thickness of the ink itself.

This is especially useful when using glossy paper. The glossy paper offers limited porosity if any. For this reason, inks wetting the surface remain in wet form and do not dry quickly. Thermal energy can be imparted to the surface of the web to assist in removing the solvents used in the inks. The solvents have a slow drying rates and cannot be easily removed which slows down the web speed.

The combination of thermal energy and an initiation radiation can be used in the present invention.

Figure 58:
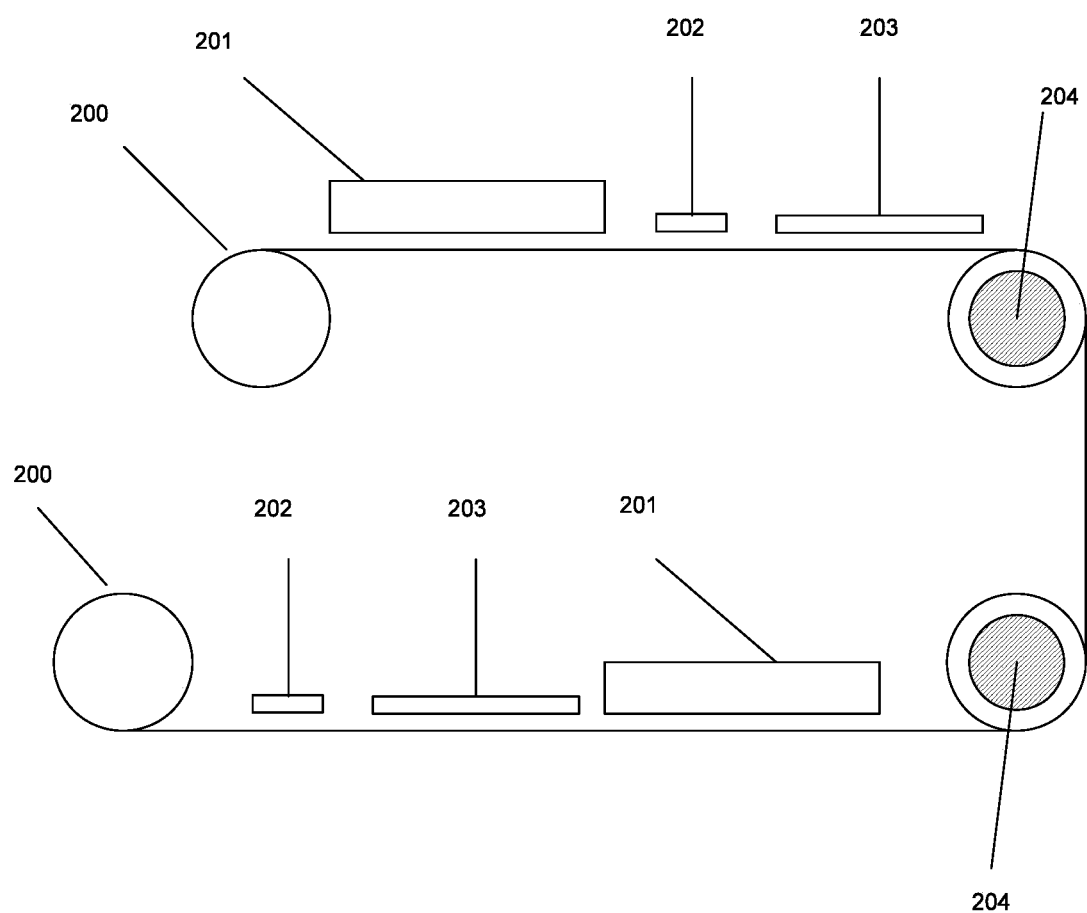
FIG. 58 provides a schematic representation of a digital printing press.

A reel of glossy paper (200) feeds a portion of the digital printing press described in FIG. 58. The paper is imparted with ink though an ink dispensing station (201). The source of an initiation radiation (202) flashes the ink with x-ray or EUV. The phosphors embedded within the ink and having a slow decay time are activated with the x-ray or EUV. The paper moves to the thermal station (203). The paper is then turned around a first pulley (204) and a second pulley (204). The back side of the paper is now ready for printing using a ink dispensing station (201). The thermal treatment as well as the UV flashing is imparted on the ink using station 203 and 202. The paper is then moved to another portion of the digital printing press.

Various other embodiments are possible.

Figure 59A:
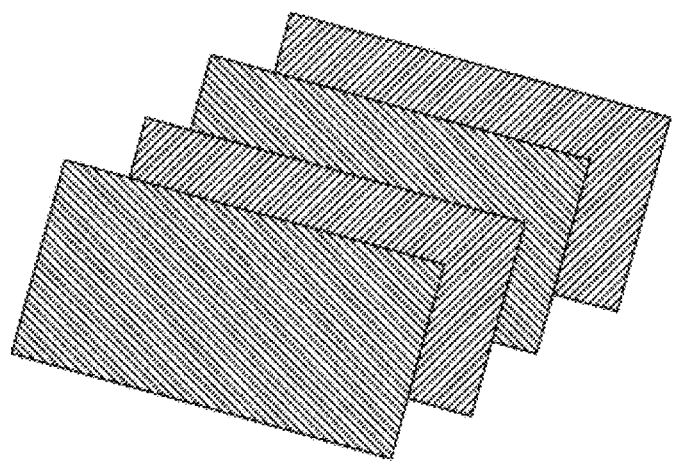
FIGS. 59A and 59B provide representations of an embodiment of the present invention for forming −45+45 composite ply assemblies.
Figure 59B:
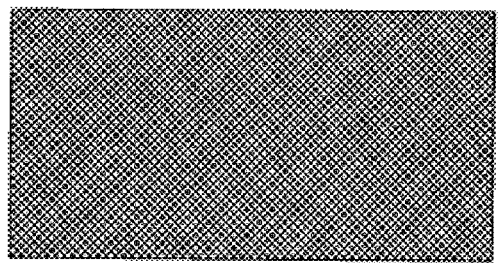
Figure 60A:
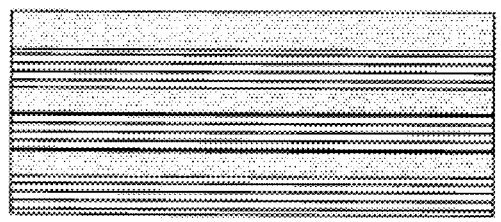
FIGS. 60A and 60B provide representations of an embodiment of the present invention for forming 0+90 composite ply assemblies.
Figure 60B:
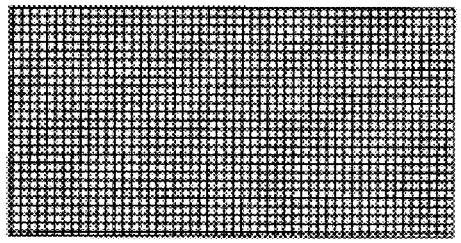

Composites:

The present invention adhesives can also be used in the formation of composites, by the adhesion of two or more plies, which are the fundamental building blocks of layered composites. The composites can be built by layering the plies, with the plies adhered one to the other using the adhesive composition of the present invention. Any conventional ply can be prepared, such as −45+45 assemblies (See FIGS. 59A and B), 0+90 composites (see FIGS. 60A and B).

The composite is preferably formed by preparation of a prepreg material formed of the plurality of plies, with each ply placed in the desired configuration with respect to the other plies, and having the curable adhesive composition of the present invention between respective layers of the plies. Once the prepreg is assembled, and the layers aligned as desired, the curable adhesive can be cured by application of the desired ionizing radiation, such as X-rays, thereby adhering the plies together to form the composite.

Front End Semiconductor Photo-Lithography

The adhesive composition of the present invention can alternatively be used in photolithography as a curable resin to accomplish either negative or positive photo-resist development. By the use of heavy metal masking elements, it is possible to get selective curing of the present invention composition to form desired patterns or semiconductor elements. If the element is desired to be electrically conductive, the adhesive composition can be doped with electroconductive fillers, as desired.

While many of the above described embodiments use downconverting particles that are dispersed throughout the curable adhesive composition, many other configurations are available for use with the present invention. For example, the downconverting particles can be adhered to a thin film (preferably to both sides of the thin film) which can be placed between two surfaces, each of which is coated with the curable adhesive monomer and photoinitiator formulation. Upon irradiation, the downconverting particles emit energy at the desired wavelength, activating the photoinitiator, and initiating curing of both layers of adhesive, thus bonding each of the surfaces to an opposite side of the thin film having the downconverting particles. One of ordinary skill, upon reviewing the present invention, would readily understand a wide variety of configurations that could be used to create novel adhered structures.

EXAMPLES

Having generally described this invention, a further understanding can be obtained by reference to certain specific examples which are provided herein for purposes of illustration only and are not intended to be limiting unless otherwise specified.

The materials chemistries were prepared by first weighing the key chemical ingredients and mixing these chemical ingredients under heat. A functionalized Acrylate resin was obtained from BASF. The resin was made from a mixture of 4 commercially available products including Laromer LR 9023, Laromer PO 94F, Laromer TPGDA, Laromer LR 9004.

The photoinitiators were also obtained from BASF and consisted of IRGACURE 369 and IRGACURE 2529. The phosphors were obtained from Phosphor Technologies. The LaOBr:$Tb^{3+}$ phosphor as well as the $YTaO_4$ were used in the preparation of the curing formulations. The third phosphor was $Y_2O_3$ doped with Gadolinium ($Y_2O_3$:Gd). This third phosphor was synthesized in nano-particle size. It was used both as a phosphor and as a thickening agent.

The temperature that was used during all the mixing steps was 80° C. The sequence of adding the various chemicals was as follows: 1—resin, 2—photoinitiator, 3—phosphor and 4—thickening agent. In one case the thickening agent was the $Y_2O_3$:Gd. The mixtures stirred every 10 minutes for one hour to two hours. This ensured the obtainment of a homogenous mixture.

In one case MEKP was added to an adhesive formulation to assess the effectiveness of X-Ray curing on coupling energy to MEKP and enhancing the cure kinetics. It was found that recipe or formulation number 2, 3 and 4 cured faster than other formulations. However adhesion was compromised when excess photo-initiator was used. For this reason recipe 4 worked best. It cured faster that recipe 2 and had better adhesion than recipe 3.

It was discovered that the uniformity of dispersion was critical to the process. The more uniform the dispersion the better results in terms of adhesion. When clusters of phosphor rich and or phosphor poor areas were noticeable, the cure was localized and the overall adhesion over a surface area was not good. When the photo-initiator is saturating the mix (excessive amount of photoinitiator), the adhesion at surfaces is compromised as there was a migration of un-reacted photo-initiator at the surfaces.

Curing of the various formulations was done on PET, glass, polycarbonate, polyimide, polysulfone, a carbon prepreg, a FR4 PCB. The adhesive bead was sandwiched between two similar substrates and cured while in between the substrates. No temperature was increased while in the x-ray. The temperature was measured using a hand-held IR thermometer. The only time a noticeable temperature increase of up to 10° C. was observed is in the case of the formulation containing MEKP.

| Formulations | 1 | 2 | 3 | 4 | 5 | 6 |
|---|---|---|---|---|---|---|
| Resin | 5 | 5 | 5 | 5 | — | — |
| Resin (shadow cure) | — | — | — | — | 5 | 5 |
| IRGACURE (369) | 1.3 | 1.3 | 1.3 | 1.3 | — | — |
| IRGACURE (2959) | — | — | — | — | 0.5 | 0.5 |
| LaOBr:Tb | 1.5 | 2.5 | 3.5 | 2.5 | 2.5 | 2.5 |
| $Y_2O_3$ | — | — | — | 0.3 | — | — |
| AEROSIL | 0.2 | 0.2 | 0.2 | 0.2 | 0.2 | 0.2 |
| CABOSIL | — | — | — | — | — | — |
| MEKP | — | — | — | 0 | 0.1 | — |

Additional formulations were cured. The elapsed time under X-Ray was 10 min, 12.5 min, 15 min, 17.5 min and 20 min. The formulations that were made using the LaOBr:$Tb^{3+}$ phosphor cured between 10 min and 12.5 min. The formulations that were made using the phosphor $YTaO_4$ cured between 12.5 min and 15 min. The formulations using the third phosphor was $Y_2O_3$ doped with Gadolinium ($Y_2O_3$:Gd) cured in 17.5 minutes. However when the LaOBr:$Tb^{3+}$ mixed with $Y_2O_3$:Gd were added to the adhesive formulations, the cure was accomplished in 10 min.

| Formulations | 1 | 2 | 3 | 4 | 5 | 6 |
|---|---|---|---|---|---|---|
| Resin 1 | 6 | 6 | 6 | 6 | 6 | 6 |
| Resin 2 (shadow Cure) | 0 | 0 | 0 | 0 | 0 | 0 |
| PI (369) | 0.6 | 0.6 | 0.6 | 0.6 | 0.6 | 0.6 |
| LaOBr:Tb | 1.5 | | | 1.5 | | |
| $Y_2O_3$-Ian | | 1.5 | | | 1.5 | |
| $YTaO_4$ | | | 1.5 | | | 1.5 |
| AEROSIL | 0.3 | 0.3 | 0.3 | 0.3 | 0.3 | 0.3 |

Obviously, additional modifications and variations of the present invention are possible in light of the above teachings. It is therefore to be understood that within the scope of the appended claims, the invention may be practiced otherwise than as specifically described herein.

The invention claimed is:

1. An electronic component, comprising: a substrate and one or more electronic elements, and having a lid covering at least a portion of the substrate or a portion of the one or more electronic elements, wherein the lid is attached and sealed with a cured adhesive formed from a curable adhesive composition,
   wherein the curable adhesive composition comprises:
   an organic vehicle comprising at least one polymerizable monomer,
   at least one photo-initiator responsive to a selected wavelength of light; and
   at least one energy converting material selected to emit said wavelength of light when exposed to a selected imparted radiation, wherein the at least one energy converting material is a downconverting material.

2. The electronic component of claim 1, wherein the adhesive is an electrically conductive adhesive.

3. The electronic component of claim 1, wherein the adhesive is a thermally conductive adhesive.

4. The electronic component of claim 2, wherein the adhesive is a thermally conductive adhesive.

5. The electronic component of claim 3, wherein the thermally conductive adhesive is electrically insulating.

6. The electronic component of claim 2, wherein the electrically conductive adhesive comprises an electrically conductive filler.

7. The electronic component of claim 6, wherein the electrically conductive filler is an organic filler.

8. The electronic component of claim 6, wherein the electrically conductive filler is an inorganic filler.

9. The electronic component of claim 7, wherein the organic filler is carbon.

10. The electronic component of claim 8, wherein the inorganic filler is finely divided metal particles.

11. The electronic component of claim 10, wherein the finely divided metal particles are formed of a metal or a metal oxide.

12. The electronic component of claim 11, wherein the finely divided metal particles are formed of a metal selected from the group consisting of gold, silver, nickel, copper, and alloys containing at least these metals.

13. The electronic component of claim 7, wherein the organic filler comprises small polymer beads or spheres having a conductive coating thereon.

14. The electronic component of claim 13, wherein the conductive coating is a thin gold film.

15. The electronic component of claim 1, wherein the curable adhesive composition further comprises a dielectric material.

16. The electronic component of claim 15, wherein the dielectric material is a member selected from the group consisting of metal titanates and metal zirconates.

17. The electronic component of claim 1, wherein the electronic component is a semiconductor component.

18. The electronic component of claim 17, wherein the cured adhesive is an anisotropically conductive adhesive.

19. The electronic component of claim 1, wherein the electronic component is an optoelectronic component.

20. The electronic component of claim 1, wherein the electronic component is a multichip module.

21. The electronic component of claim 1, wherein the electronic component is an integrated circuit device.

22. The electronic component of claim 21, wherein the integrated circuit device is an integrated circuit wafer stack.

23. The electronic component of claim 1, wherein the electronic component is a high density circuit.

24. The electronic component of claim 21, wherein the integrated circuit device is a flip chip.

25. The electronic component of claim 24, wherein the at least one energy converting material is a phosphor having absorption characteristics in an X-ray regime, such that inspection of the resulting flip chip can be performed using X-rays.

26. The electronic component of claim 7, wherein the organic filler comprises anisotropic conductive polymer spheres.

27. The electronic component of claim 21, wherein the cured adhesive further comprises anisotropic conductive polymer spheres.

28. The electronic component of claim 1, wherein the at least one energy converting material comprises anisotropic conductive UV emitting polymer spheres.

29. The electronic component of claim 21, wherein the at least one energy converting material comprises anisotropic conductive UV emitting polymer spheres.

30. The electronic component of claim 1, wherein the imparted radiation is an ionizing radiation.

31. The electronic component of claim 30, wherein the ionizing radiation is X-rays.

32. The electronic component of claim 1 wherein said organic vehicle comprises a monomer forming a thermoset resin.

33. The electronic component of claim 32, wherein said thermoset resin is selected from the group consisting of: acrylics, phenolics, urethanes, epoxies, styrenes, and silicones.

34. The electronic component of claim 1, wherein said at least one photoinitiator is selected from the group consisting of: benzoin ethers, benzil ketals, α-dialkoxyacetophenones, α-aminoalkylphenones, acylphosphine oxides, benzophenones/amines, thioxanthones/amines, and titanocenes.

35. The electronic component of claim 1, wherein said wavelength of light is in the UV range and said ionizing radiation comprises X-rays.

36. The electronic component of claim 1, wherein said downconverting material comprises dispersed inorganic particulates selected from the group consisting of: metal oxides; metal sulfides; doped metal oxides; and mixed metal chalcogenides.

37. The electronic component of claim 1, wherein said curable adhesive composition further comprises inorganic particulates selected from the group consisting of: metals and metal alloys, ceramics and dielectrics, and metal-coated polymers.

38. The electronic component of claim 1, wherein said curable adhesive composition further comprises an organic component selected from the group consisting of: solvents, viscosity modifiers, surfactants, dispersants, and plasticizers.

39. The electronic component of claim 1, wherein the at least one photo-initiator and the at least one energy converting material are chemically tethered to one another.

40. The electronic component of claim 1, wherein the cured adhesive is in the form of a film.

41. The electronic component of claim 40, wherein the cured adhesive in the form of a film is partially cured.

42. The cured adhesive of claim 40, wherein the film has anisotropic properties.

43. The electronic component of claim 17, wherein the cured adhesive is an isotropically conductive adhesive.

44. A phosphor composition, comprising:
one or more phosphors having on a surface thereof a coating selected from the group consisting of silica, diamond, and diamond-like carbon, said one or more phosphors configured to emit radiation upon interaction with an initiation energy.

45. The phosphor composition of claim 44, wherein the one or more phosphors comprises one or more of visible emitting phosphors and ultraviolet emitting phosphors.

46. The phosphor composition of claim 44, wherein the one or more of phosphors comprises a mixture of the phosphors.

47. The phosphor composition of claim 44, wherein the one or more phosphors further comprises a plasmonics agent including a metallic structure.

48. The phosphor composition of claim 44, wherein the coating is a diamond-like carbon coating.

49. The phosphor composition of claim 48, wherein the diamond-like carbon coating is formed by chemical vapor deposition.

50. The phosphor composition of claim 49, wherein the diamond-like carbon coating is formed by said chemical vapor deposition using hydrogen gas and methane gas.

51. The phosphor composition of claim 44, wherein the coating is a silica coating.

52. The phosphor composition of claim 51, wherein the silica coating is formed by a sol-gel process.

53. The phosphor composition of claim 44, wherein the coating is a diamond coating.

54. The phosphor composition of claim 53, wherein the diamond coating is formed by chemical vapor deposition.

55. The phosphor composition of claim 54, wherein the diamond coating is formed by said chemical vapor deposition using hydrogen gas and methane gas.

* * * * *

UNITED STATES PATENT AND TRADEMARK OFFICE
CERTIFICATE OF CORRECTION

| | |
|---|---|
| PATENT NO. | : 10,748,868 B2 |
| APPLICATION NO. | : 16/103355 |
| DATED | : August 18, 2020 |
| INVENTOR(S) | : Zakaryae Fathi et al. |

Page 1 of 4

It is certified that error appears in the above-identified patent and that said Letters Patent is hereby corrected as shown below:

In the Drawings

In sheet 31 of 64, FIG. 30C, Lines 5-6, "X- ray" should read --X-ray--

In the Specification

Column 5, Line 50, "invention" should read --invention.--

Column 6, Line 31, "range)" should read --range).--

Column 9, Line 12, "Semiconductors" should read --Semiconductors:--

Column 10, Line 19, "fire!" should read --fire.--

Column 12, Line 44, "⌈available" should read --[available--

Column 12, Line 45, "MO.⌉" should read --MO.]--

Column 12, Line 48, "saltmonohydrate," should read --salt monohydrate,--

Column 13, Line 7, "Methybenzoylformate," should read --Methylbenzoylformate,--

Column 13, Line 27, "ethoxy⌉-" should read --ethoxy]- --

Column 13, Line 28, "2-⌈2" should read --2-[2--

Column 13, Line 28, "ethoxy⌉-" should read --ethoxy]- --

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,748,868 B2

Column 13, Line 31, "(2-" should read --2- --

Column 13, Line 33, "phenyl]" should read --phenyl]--

Column 13, Line 36, "(Diphenyl" should read --Diphenyl--

Column 13, Line 37, "alpah" should read --alpha--

Column 13, Lines 42-43, "(IRGACURE" should read --IRGACURE--

Column 13, Line 44, "Bis [2" should read --Bis [2--

Column 13, Line 46, "(4-methylphenyl)[4" should read --(4-methylphenyl) [4--

Column 15, TABLE 1, Line 5 (approx.), "$BaSO_4$-" should read --$BaSO_4^-$--

Columns 15-16, Line 11, "Hexgonal" should read --Hexagonal--

Columns 15-16, Line 12, "Hexgonal" should read --Hexagonal--

Columns 15-16, Line 13, "Hexgonal" should read --Hexagonal--

Columns 15-16, Line 14, "Hexgonal" should read --Hexagonal--

Columns 15-16, Line 15, "Hexgonal" should read --Hexagonal--

Column 17, Line 21, "antharacene" should read --anthracene--

Column 18, Line 37, "naphthaquinone," should read --naphthoquinone--

Column 18, Line 38, "fluoresceine," should read --fluorescein--

Column 18, Line 39, "dibenzantronile," should read --dibenzonitrile,--

Column 18, TABLE 2, Line 6, "Tl+" should read --TI+--

Column 18, TABLE 2, Line 8, "CsI" should read --Csi--

Column 18, TABLE 2, Line 9, "Tl+" should read --TI+--

Column 18, TABLE 2, Line 11, "CsI" should read --Csi--

Column 18, TABLE 2, Line 25, "SrMgP2O7" should read --$SrMgP_2O_7$--

Columns 19-20, TABLE 2-continued, Line 8, "Hexgonal" should read --Hexagonal--

CERTIFICATE OF CORRECTION (continued)
U.S. Pat. No. 10,748,868 B2

Columns 19-20, TABLE 2-continued, Line 11, "Hexgonal" should read --Hexagonal--

Columns 19-20, TABLE 2-continued, Line 14, "Hexgonal" should read --Hexagonal--

Columns 19-20, TABLE 2-continued, Line 15, "Hexgonal" should read --Hexagonal--

Columns 19-20, TABLE 2-continued, Line 16, "Hexgonal" should read --Hexagonal--

Column 19, Line 48, "IRGACUR" should read --IRGACURE--

Column 19, Line 50, "IRGACUR" should read --IRGACURE--

Column 19, Line 51, "IRGACUR" should read --IRGACURE--

Column 19, Line 52, "IRGACUR" should read --IRGACURE--

Column 19, Line 53, "IRGACUR" should read --IRGACURE--

Column 21, Line 45, "photoiniators" should read --photoinitiators--

Column 24, Line 18, "characterstics" should read --characteristics--

Column 24, Line 45, "Photoiniators" should read --Photoinitiators.--

Column 29, Line 25, "inspection" should read --inspection.--

Column 29, Line 30, "cure" should read --cure.--

Column 29, Line 47, "flexiblizers" should read --flexibilizers--

Column 30, Line 59, "aniostropically" should read --anisotropically--

Column 34, Line 26, "1C" should read --IC--

Column 37, Line 41, "FIG." should read --FIGS.--

Column 37, Line 60, "X_Ray" should read --X-Ray--

Column 37, Line 67, "FIG." should read --FIGS.--

Column 39, Line 17, "and or" should read --and/or--

Column 41, Line 24, "(no" should read --no--

Column 42, Line 59, "Miroprocessors" should read --Microprocessors--

CERTIFICATE OF CORRECTION (continued)
U.S. Pat. No. 10,748,868 B2

Column 43, Line 25, "140c." should read --140c--

Column 43, Line 34, "150'" should read --150'.--

Column 47, Line 7, "and or" should read --and/or--